US006316503B1

(12) United States Patent
Li et al.

(10) Patent No.: US 6,316,503 B1
(45) Date of Patent: Nov. 13, 2001

(54) LXR MODULATORS

(75) Inventors: Leping Li, Burlingame; Julio C. Medina, San Carlos; Kevin Lustig, South San Francisco; Bei Shan, Redwood City, all of CA (US); Hirohiko Hasegawa, Osaka (JP); Serena T. Cutler, Palo Alto, CA (US); Jiwen Liu; Liusheng Zhu, both of Burlingame, CA (US)

(73) Assignee: Tularik Inc., So. San Francisco, CA (US)

( * ) Notice: Subject to any disclaimer, the term of this patent is extended or adjusted under 35 U.S.C. 154(b) by 0 days.

(21) Appl. No.: 09/525,861

(22) Filed: Mar. 14, 2000

Related U.S. Application Data

(60) Provisional application No. 60/124,525, filed on Mar. 15, 1999.

(51) Int. Cl.$^7$ .................................................. A01N 41/06
(52) U.S. Cl. ........................ 514/604; 514/585; 514/596; 514/447; 514/448; 514/352; 514/354; 514/371; 514/365; 564/84; 564/92; 564/52; 564/53; 564/55; 564/26; 549/69; 549/72; 546/308; 546/310; 548/196; 548/200
(58) Field of Search ...................... 564/52, 53, 55, 564/26, 84, 92; 514/585, 596, 604, 447, 448, 352, 354, 371, 365; 549/69, 72; 546/308, 310; 548/196, 200

(56) References Cited

U.S. PATENT DOCUMENTS

| | | |
|---|---|---|
| 3,281,466 | 10/1966 | Stecker et al. . |
| 3,495,177 | 2/1970 | Jones et al. . |
| 4,093,742 | 6/1978 | Neustadt . |
| 4,107,303 | 8/1978 | Aldrich et al. . |
| 4,199,597 | 4/1980 | Neustadt et al. . |
| 4,218,448 | 8/1980 | Aldrich et al. . |
| 4,230,635 | 10/1980 | Neustadt . |
| 4,240,979 | 12/1980 | Baumann et al. . |
| 4,251,534 | 2/1981 | Aldrich et al. . |
| 4,251,659 | 2/1981 | Aldrich et al. . |
| 4,267,193 | 5/1981 | Neustadt et al. . |
| 5,883,106 | * 3/1999 | Stevens et al. ...................... 514/277 |
| 6,030,991 | * 2/2000 | Chan et al. ........................ 514/380 |
| 6,156,766 | * 12/2000 | Arita et al. ........................ 514/300 |
| 6,162,830 | * 12/2000 | Connor et al. ..................... 514/604 |
| 6,174,905 | * 1/2001 | Suzuki et al. ...................... 514/346 |
| 6,191,170 | * 2/2001 | Medina ............................. 514/604 |
| 6,197,798 | * 3/2001 | Fink et al. ........................ 514/354 |
| 6,201,013 | * 3/2001 | Bloom et al. ..................... 514/461 |
| 6,211,241 | * 4/2001 | Islam et al. ....................... 514/602 |
| 6,211,242 | * 4/2001 | Setoi et al. ........................ 514/616 |
| 6,214,880 | * 4/2001 | Houze .............................. 514/595 |
| 6,242,493 | * 6/2001 | Gareau et al. ..................... 514/569 |

FOREIGN PATENT DOCUMENTS

| | | |
|---|---|---|
| 0 193 249 A2 | 9/1986 | (EP) . |
| 0 919 542 A2 | 6/1999 | (EP) . |
| 1 507 340 | 4/1978 | (GB) . |
| 872.311 | 5/1979 | (RU) . |
| WO 00/46203 | 8/2000 | (WO) . |

OTHER PUBLICATIONS

Miryan, et al.: "Derivatives of pyridinecarboxylic acids. Synthesis and antiexudative effect of fluorinated derivatives of nicotinamide and isonicotinamide" Database Chemabs 'Online! Chemcial Abstract Service, accession No. 86:139798 XP–002151153; (1977), 11(1), 70–2 Russian Abstract.

Polishchuck, V. R., et al.: "Electron paramagnetic resonance spectra of 2–arylpolyfluoroisopropyl radicals" Database Chemabs 'Online !Chemcial Abstract Service, accession No. 91: 4737 CA XP–002151154, (1979), (3) pp 659–661, Russian Abstract.

Gilbert, et al. "Perhalo ketones—(VI) aromatic amino derivs. of the penhaloacetones" Database 'Online accession No. 16091f XP–002151155, Russian Abstract.

Chkanikov, et al. Hexafluoroacetone and Methyl Trifluoropyruvate as Precursors of Modified Esters of n–acyl–n–phenyl–α–amino acids, *Bulletin of the Russian Academy of Sciences*, 41(8) Part 2 pp 1415–1424.

\* cited by examiner

*Primary Examiner*—Deborah C. Lambkin
(74) *Attorney, Agent, or Firm*—Townsend and Townsend and Crew LLP

(57) ABSTRACT

The invention provides compounds, compositions and methods for modulating the effects of LXR in a cell. The compounds and compositions are useful both as diagnostic indicators of LXR function and as pharmacologically active agents. The compounds and compositions find particular use in the treatment of disease states associated with cholesterol metabolism, particularly atherosclerosis and hypercholesterolemia.

47 Claims, 2 Drawing Sheets

Compounds from Solid Phase Synthesis

Compounds from Solid Phase Synthesis

LXR MODULATORS

This application claims benefit of Ser. No. 60/124,525 filed Mar. 15, 1999.

FIELD OF THE INVENTION

The present invention relates to compounds and methods useful for the modulation of LXR. In view of the activity of LXR in the control of cholesterol homeostasis, the compounds described herein are useful for lowering plasma cholesterol levels.

BACKGROUND

Cholesterol is used for the synthesis of bile acids in the liver, the manufacture and repair of cell membranes, and the synthesis of steroid hormones. There are both exogenous and endogenous sources of cholesterol. The average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation). Excess accumulation of cholesterol in the arterial walls can result in atherosclerosis, which is characterized by plaque formation. The plaques inhibit blood flow, promote clot formation and can ultimately cause heart attacks, stroke and claudication. Development of therapeutic agents for the treatment of atherosclerosis and other diseases associated with cholesterol metabolism has been focused on achieving a more complete understanding of the biochemical pathways involved. Most recently, liver X receptors (LXRs) were identified as key components in cholesterol homeostasis.

The LXRs were first identified as orphan members of the nuclear receptor superfamily whose ligands and functions were unknown. Two LXR proteins ($\alpha$ and $\beta$) are known to exist in mammals. The expression of LXR$\alpha$ is restricted, with the highest levels being found in the liver, and lower levels found in kidney, intestine, spleen, and adrenals (see Willy, et al., *Genes Dev.* 9(9):1033–45 (1995)). LXR$\beta$ is rather ubiquitous, being found in nearly all tissues examined. Recent studies on the LXRs indicate that they are activated by certain naturally occurring, oxidized derivatives of cholesterol, including 22(R)-hydroxycholesterol, 24(S)-hydroxycholesterol and 24,25(S)-epoxycholesterol (see Lehmann, et al., *J. Biol. Chem.* 272(6):3137–3140 (1997)). The expression pattern of LXRs and their oxysterol ligands provided the first hint that these receptors may play a role in cholesterol metabolism (see Janowski, et al., *Nature* 383:728–731 (1996)).

As noted above, cholesterol metabolism in mammals occurs via conversion into steroid hormones or bile acids. The role of LXRs in cholesterol homeostasis was first postulated to involve the pathway of bile acid synthesis, in which cholesterol 7$\alpha$-hydroxylase (CYP7A) operates in a rate-limiting manner. Support for this proposal was provided when additional experiments found that the CYP7A promoter contained a functional LXR response element that could be activated by RXR/LXR heterodimers in an oxysterol- and retinoid-dependent manner. Confirmation of LXR function as a transcriptional control point in cholesterol metabolism was made using knockout mice, particularly those lacking the oxysterol receptor LXR$\alpha$ (see Peet, et al., *Cell* 93:693–704 (1998)).

Mice lacking the receptor LXR$\alpha$ (e.g., knockout or (–/–) mice) lost their ability to respond normally to increases in dietary cholesterol and were unable to tolerate any cholesterol in excess of that synthesized de novo. LXR$\alpha$ (–/–) mice did not induce transcription of the gene encoding CYP7A when fed diets containing additional cholesterol. This resulted in an accumulation of large amounts of cholesterol and impaired hepatic function in the livers of LXR$\alpha$ (–/–) mice. These results further established the role of LXR$\alpha$ as the essential regulatory component of cholesterol homeostasis. LXR$\alpha$ is also believed to be involved in fatty acid synthesis. Accordingly, regulation of LXR$\alpha$ (e.g., use of LXR$\alpha$ agonist or antagonists) could provide treatment for a variety of lipid disorders including obesity and diabetes.

In view of the importance of LXRs, and particularly LXR$\alpha$s to the delicate balance of cholesterol metabolism and fatty acid biosynthesis, we describe modulators of LXRs which are useful as therapeutic agents or diagnostic agents for the treatment of disorders associated with bile acid and cholesterol metabolism, including cholesterol gallstones, atherosclerosis, lipid storage diseases, obesity, and diabetes. The agents described herein are also useful for disease states associated with serum hypercholesterolemia, such as coronary heart disease.

SUMMARY OF THE INVENTION

In one aspect, the present invention provides compositions for modulation of LXR$\alpha$ function in a cell. The compositions typically comprise a pharmaceutically acceptable excipient and a compound having the formula:

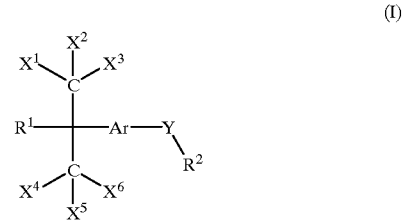

(I)

wherein Ar represents an aryl group; $R^1$ is —OH, —O—($C_1$–$C_7$)alkyl, —OC(O)—($C_1$–$C_7$)alkyl, —O—($C_1$–$C_7$)heteroalkyl, —OC(O)—($C_1$–$C_7$)heteroalkyl, —$CO_2$H, —$NH_2$, —NH($C_1$–$C_7$)alkyl, —N(($C_1$–$C_7$)alkyl)$_2$ or —NH—S(O)$_2$—($C_1$–$C_5$)alkyl; $R^2$ is ($C_1$–$C_7$)alkyl, ($C_1$–$C_7$)heteroalkyl, aryl and aryl($C_1$–$C_7$)alkyl; $X^1$, $X^2$, $X^3$, $X^4$, $X_5$ and $X^6$ are each independently H, ($C_1$–$C_5$)alkyl, ($C_1$–$C_5$)heteroalkyl, F or Cl, with the proviso that no more than three of $X^1$ through $X^6$ are H, ($C_1$–$C_5$)alkyl or ($C_1$–$C_5$)heteroalkyl; and Y is —N($R^{12}$)S(O)$_m$—, —N($R^{12}$)S(O)$_m$N($R^{13}$)—, —N($R^{12}$)C(O)—, —N($R^{12}$)C(O)N($R^{13}$)—, —N($R^{12}$)C(S)— or —N($R^{12}$)C(O)O—, wherein $R^{12}$ and $R^{13}$ are each independently hydrogen, ($C_1$–$C_7$)alkyl, ($C_1$–$C_7$)heteroalkyl, aryl and aryl($C_1$–$C_7$)alkyl, and optionally when Y is —N($R^{12}$)S(O)$_m$— or —N($R^{12}$)S(O)$_m$N($R^{13}$)—, $R^{12}$ forms a five-, six- or seven-membered ring fused to Ar or to $R^2$ through covalent attachment to Ar or $R^2$, respectively. In the above Y groups, the subscript m is an integer of from 1 to 2.

Preferred compositions are those in which the compound above binds to the ligand binding domain of LXR$\alpha$ with an affinity of at least 1 micromolar.

A number of compounds that are useful in the above-described compositions are novel. Accordingly, the present invention further provides compounds of the above formula, with the proviso that when $R^1$ is OH, and —Y—$R^2$ is —N($R^{12}$)S(O)$_m$$R^2$ or —N($R^{12}$)C(O)N($R^{13}$)—$R^2$ and is attached to a position para to the quaternary carbon attached to Ar, and when $R^2$ is phenyl, benzyl or benzoyl, then i) at least one of $R^{12}$ or $R^{13}$ is other than hydrogen and contains an electron-withdrawing substituent, or ii) $R^2$ is substituted with a moiety other than amino, acetamido, di($C_1$–$C_7$) alkylamino, ($C_1$–$C_7$)alkylamino, halogen, hydroxy, nitro, or ($C_1$–$C_7$)alkyl, or iii) the benzene ring portion of $R^2$ is trisubstituted in addition to the Y group.

In yet another aspect, the present invention provides methods for modulating LXR in a cell by administering to or contacting the cell with a composition containing a compound of Formula I above.

In still another aspect, the present invention provides methods for treating LXR-responsive diseases by administering to a subject in need of such treatment a composition containing a compound of Formula I. These methods are particularly useful for the treatment of pathology such as hypercholesterolemia, atherosclerosis, and hyperlipoproteinemia. In certain embodiments, the compound can be administered to the subject in combination with an additional anti-hypercholesterolemic agent, for example, bile acid sequestrants, nicotinic acid, fibric acid derivatives or HMG CoA reductase inhibitors.

The present compounds can exert their effects either systemically (the compounds permeate the relevant tissues, such as liver, upon entrance into the bloodstream) or locally (for example, by modulating LXR function of intestinal epithelial cells following oral administration, without necessitating the compounds' entrance into the bloodstream). In some disease states, some preferred compounds will be those with good systemic distribution, while, in other instances, preferred compounds will be those that can work locally on the intestinal track or on the skin without penetrating the bloodstream.

Certain compounds of the present invention are antiproliferative and can be used in compositions for treating diseases associated with abnormal cell proliferation (e.g., cancer). Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

DETAILED DESCRIPTION OF THE INVENTION

Definitions

Figure 1:
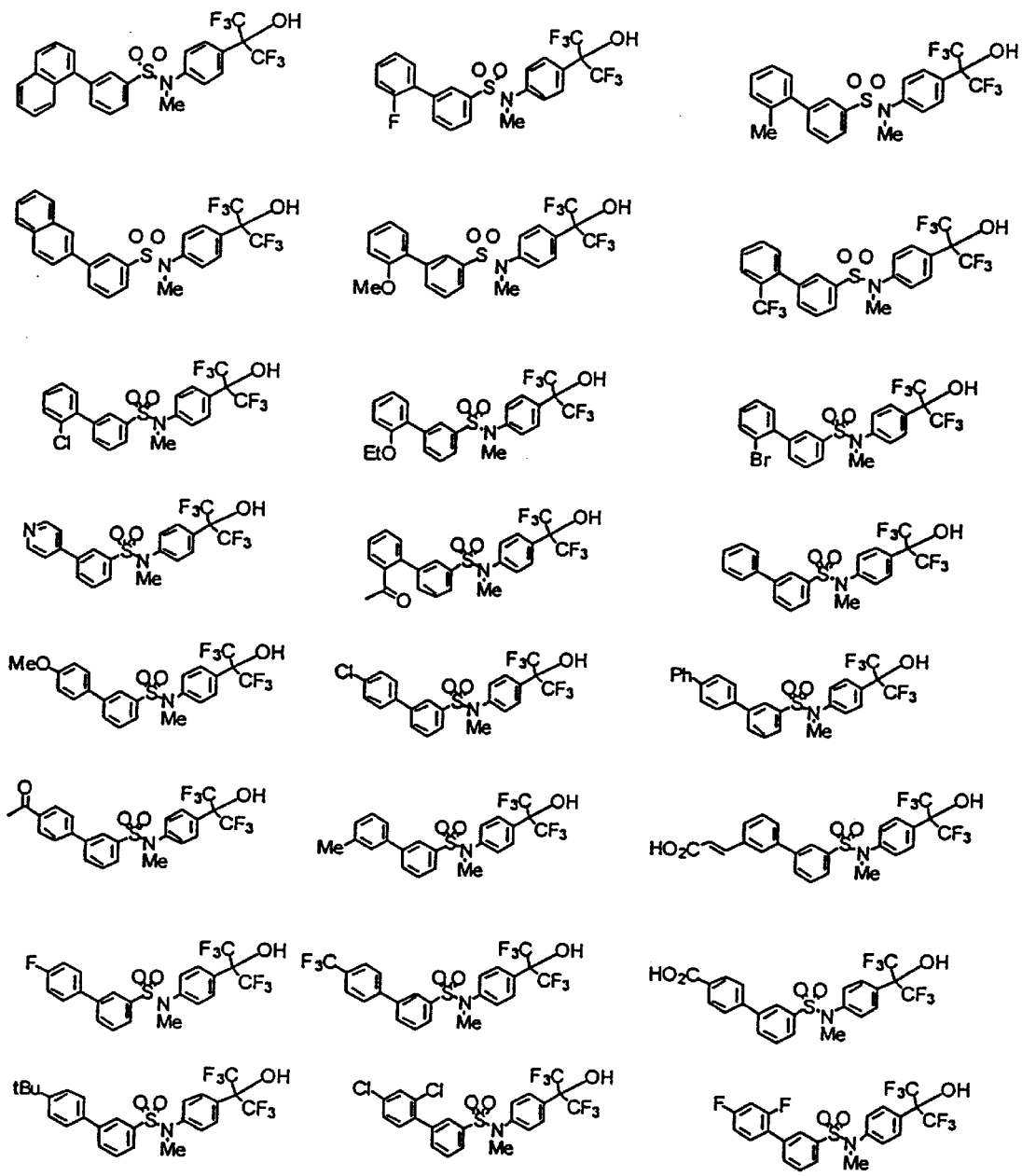
FIGS. 1 and 2 provide the structures of compounds prepared using the solid phase synthesis methodology outlined in Scheme 3.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multi-radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms, preferably four or fewer carbon atoms.

The term "alkoxy," employed alone or in combination with other terms means, unless otherwise stated, an alkyl group, as defined above, connected to the remainder of the molecule via an oxygen atom, such as, for example, methoxy, ethoxy, 1-propoxy, 2-propoxy and the higher homologs and isomers.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any position of the heteroalkyl group except for the position at which the heteroalkyl group is attached to the rest of the molecule. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, as well as all other linking groups described herein, no specific orientation of the linking group is implied.

The terms "cycloalkyl" and "heterocycloalkyl", by themselves or in combination with other terms, represent, unless otherwise stated, cyclic versions of "alkyl" and "heteroalkyl", respectively. The terms "cycloalkyl" and "heterocycloalkyl" are also meant to include bicyclic, tricyclic and polycyclic versions thereof. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, bicyclo[2.2.1]heptyl, bicyclo[2.2.2]octyl, adamantyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, 1,4-diazabicyclo[2.2.2]oct-2-yl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a carbon atom or a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-fulryl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

The terms "arylalkyl" and "arylheteroalkyl" are meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 1-naphthyloxy-3-propyl, and the like). The arylalkyl and arylheteroalkyl groups will typically contain from 1 to 3 aryl moieties attached to the alkyl or heteroalkyl portion by a covalent bond or by fusing the ring to, for example, a cycloalkyl or heterocycloalkyl group. For arylheteroalkyl groups, a heteroatom can occupy the position at which the group is attached to the remainder of the molecule. For example, the term "arylheteroalkyl" is meant to include benzyloxy, 2-phenylethoxy, phenethylamine, and the like.

Each of the above terms (e.g., "alkyl," "heteroalkyl," "aryl," etc.) are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —CO$_2$R', —CONR'R", —OC(O)NR'R", —NR"C(O)R', —NR"C(O)NR'R'", —NR"C(O)$_2$R', —NHC(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. Preferably, substituted alkyl groups will have from one to six independently selected substituents, more preferably from one to four independently selected substituents, most preferably from one to three independently selected substituents. In the substituents listed above, R', R" and R'" each independently refer to hydrogen, unsubstituted(C$_1$–C$_8$)alkyl and heteroalkyl, unsubstituted aryl, aryl substituted with 1–3 halogens, unsubstituted alkyl, alkoxy or thioalkoxy groups, or aryl-(C$_1$–C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl.

Similarly, substituents for the aryl groups are varied and are selected from: -halogen, —OR', —OC(O)R', —NR'R", —SR', —R', —CN, —NO$_2$, —CO$_2$R', —CONR'R", —OC(O)NR'R", —NR"C(O)R', —NR"C(O)$_2$R', —NR"C(O)NR'R'", —NH—C(NH$_2$)=NH, —NR'C(NH$_2$)=NH, —NH—C(NH$_2$)=NR', —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R' and R" are independently selected from hydrogen, (C$_1$–C$_8$)alkyl and heteroalkyl, unsubstituted aryl, (unsubstituted aryl)-(C$_1$–C$_4$)alkyl, and (unsubstituted aryl)oxy-(C$_1$–C$_4$)alkyl. Preferably, substituted aryl groups will have from one to four independently selected substituents, more preferably from one to three independently selected substituents, most preferably from one to two independently selected substituents.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula I. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

The present invention provides compositions, compounds and methods for modulating LXR function in a cell. The compositions which are useful for this modulation will typically be those which contain an effective amount of an LXR-modulating compound. In general, an effective amount of an LXR-modulating compound is a concentration of the compound that will produce at 50 percent increase/decrease in LXR activity in a cell-based reporter gene assay, or a biochemical peptide-sensor assay such as the assays described in co-pending applications Ser. Nos. 08/975,614 (filed Nov. 21, 1997) and 09/163,713 (filed Sep. 30, 1998).

EMBODIMENTS OF THE INVENTION

In one aspect, the present invention provides compositions for modulation of LXR function in a cell. The compositions typically comprise a pharmaceutically acceptable excipient and an LXR-modulating amount of a compound having the formula:

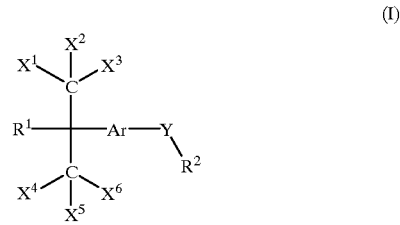

(I)

The symbol Ar represents an aryl group. A variety of aryl groups, both unsubstituted and substituted, are useful in the present invention. Preferred Ar groups are either monocyclic or fused-bicyclic aromatic rings. Particularly preferred Ar ring systems are benzene, naphthalene, pyridine, quinoline, isoquinoline, pyrrole, furan and thiophene. More preferably, Ar represents either a benzene or pyridine ring, with benzene being the most preferred.

When Ar represents a substituted aromatic ring (substituents being in addition to —Y—$R^2$ and the carbon bearing $R^1$), the substituents will typically be selected from —OH, —$NH_2$, lower alkyl (e.g., methyl, butyl, trifluoromethyl, trifluoroethyl, and the like), lower alkoxy (e.g. methoxy, ethoxy, trifluoromethoxy, butoxy, and the like), —NR'R", —SR', -halogen, —SiR'R"R'", —OC(O)R', —$CO_2$R', —CONR'R", —OC(O)NR'R", —NR"C(O)R', —NR"C(O)$_2$R', —NR"C(O)NR'R'", —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$; wherein R', R" and R'" are each independently selected from the group consisting of hydrogen and ($C_1$–$C_5$)alkyl. Preferred compounds are those in which the number of substituents on the Ar group (in addition to —Y—$R^2$ and the carbon bearing $R^1$) ranges from 0 to 2.

The groups attached to Ar can be in any spatial arrangement. When Ar is a benzene ring, the two groups shown in Formula I will preferably be attached to Ar in a 1,3-orientation (meta) or a 1,4-orientation (para). More preferably the two groups shown in Formula I will be attached to a benzene or pyridine ring in a 1,4-orientation (para).

Returning now to Formula I, $R^1$ represents —OH, —O—($C_1$–$C_7$)alkyl, —OC(O)—($C_1$–$C_7$)alkyl, —O—($C_1$–$C_7$)heteroalkyl, —OC(O)—($C_1$–$C_7$)heteroalkyl, —$CO_2$H, —$NH_2$, —NH($C_1$–$C_7$)alkyl, —N(($C_1$–$C_7$)alkyl)$_2$ or —NH—S(O)$_2$—($C_1$–$C_5$)alkyl. More preferably, $R^1$ represents —OH, —$CO_2$H, —$NH_2$, —NH($C_1$–$C_7$)alkyl, —N(($C_1$–$C_7$)alkyl)$_2$ or —NH—S(O)$_2$—($C_1$–$C_5$)alkyl. Most preferably, $R^1$ is —OH. For those embodiments in which $R^1$ is a dialkylamino group (—N(($C_1$–$C_7$)alkyl)$_2$), the alkyl groups can either be the same or different.

The symbols $X^1$, $X^2$, $X^3$, $X^4$, $X^5$ and $X^6$ each independently represent H, ($C_1$–$C_5$)alkyl, ($C_1$–$C_5$)heteroalkyl, F or Cl, with the proviso that no more than three of $X^1$ through $X^6$ are H, $(C_1-C_5)$alkyl or $(C_1-C_5)$heteroalkyl. More preferably, no more than three of $X^1$ through $X^6$ are H with the remaining being F. Most preferably, $X^1$ through $X^6$ are each F.

The symbol Y represents a linking group selected from $-N(R^{12})S(O)_m-$, $-N(R^{12})S(O)_mN(R^{13})-$, $-N(R^{12})C(O)-$, $-N(R^{12})C(O)N(R^{13})-$, $-N(R^{12})C(S)-$ or $-N(R^{12})C(O)O-$, wherein $R^{12}$ and $R^{13}$ are each independently H, $(C_1-C_7)$alkyl, $(C_1-C_7)$heteroalkyl, aryl and aryl$(C_1-C_7)$alkyl, and optionally when Y is $-N(R^{12})S(O)_m-$ or $-N(R^{12})S(O)_mN(R^{13})-$, $R^{12}$ forms a five-, six- or seven-membered ring fused to Ar or to $R^2$ through covalent attachment to Ar or to $R^2$, respectively. In the above Y groups, the subscript m is an integer of from 1 to 2. Preferably, Y is $-N(R^{12})S(O)_m-$, $-N(R^{12})S(O)_mN(R^{13})-$ or $-N(R^{12})C(O)O-$. Most preferably, Y is $-N(R^{12})S(O)_m-$.

As noted above, $R^{12}$ and $R^{13}$ represent hydrogen, $(C_1-C_7)$alkyl, $(C_1-C_7)$heteroalkyl, aryl or aryl$(C_1-C_7)$alkyl, which in the case of the latter two groups, can also be either substituted or unsubstituted. In one group of embodiments, $R^{12}$ is hydrogen or $(C_1-C_4)$alkyl, preferably fluoro$(C_1-C_4)$alkyl. A particularly preferred $R^{12}$ group is 2,2,2-trifluoroethyl. In another group of preferred embodiments, $R^{12}$ is attached to Ar to form a fused ring system, for example, indoline, tetrahydroquinoline or tetrahydroisoquinoline.

Attached to Y is $R^2$, which represents $(C_1-C_7)$alkyl, $(C_1-C_7)$heteroalkyl, aryl or aryl$(C_1-C_7)$alkyl. Each of the recited $R^2$ groups can be either substituted or unsubstituted. In preferred embodiments, $R^2$ is an aryl group. More preferably, $R^2$ is phenyl, thienyl, imidazolyl, oxazolyl or pyridyl. Most preferably, $R^2$ is phenyl or thienyl (including 2-thienyl and 3-thienyl). Preferred substituted $R^2$ groups include 3-chlorophenyl, 3-bromophenyl, 3-cyanophenyl, 3-(trifluoromethyl)phenyl, 2-chloro-3-thienyl and 2,5-dichloro-3-thienyl.

The above recitation describes a number of preferred groups for the compounds and compositions of the present invention. Additionally, certain combinations of the above groups will also be preferred. For example, in one group of embodiments, the compositions of the present invention will include a compound having a formula selected from the group consisting of

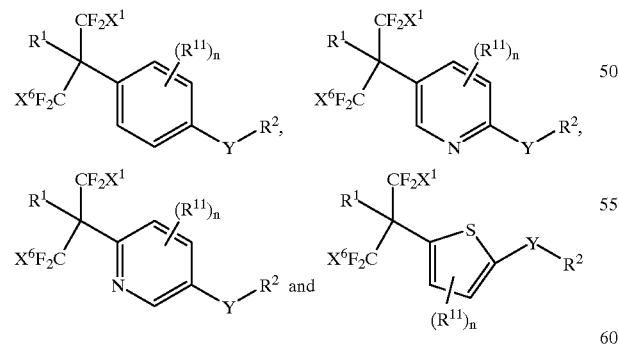

In each of the above formulae, the subscript n represents an integer of from 0 to 4; and each $R^{11}$ is independently $-OH$, $-NH_2$, lower alkyl, lower alkoxy, $-NR'R''$, $-SR'$, -halogen, $-SiR'R''R'''$, $-OC(O)R'$, $-CO_2R'$, $-CONR'R''$, $-OC(O)NR'R''$, $-NR''C(O)R'$, $-NR''C(O)_2R'$, $-NR''C(O)NR'R'''$, $-NH-C(NH_2)=NH$, $-NR'C(NH_2)=NH$, $-NH-C(NH_2)=NR'$, $-S(O)R'$, $-S(O)_2R'$, $-S(O)_2NR'R''$, $-CN$ and $-NO_2$; wherein each R', R'' and R''' is independently hydrogen or $(C_1-C_5)$alkyl. The remaining groups in the above formulae have the meanings provided for Formula I.

In a further preferred group of embodiments, the compositions will include a compound having a formula selected from the group consisting of

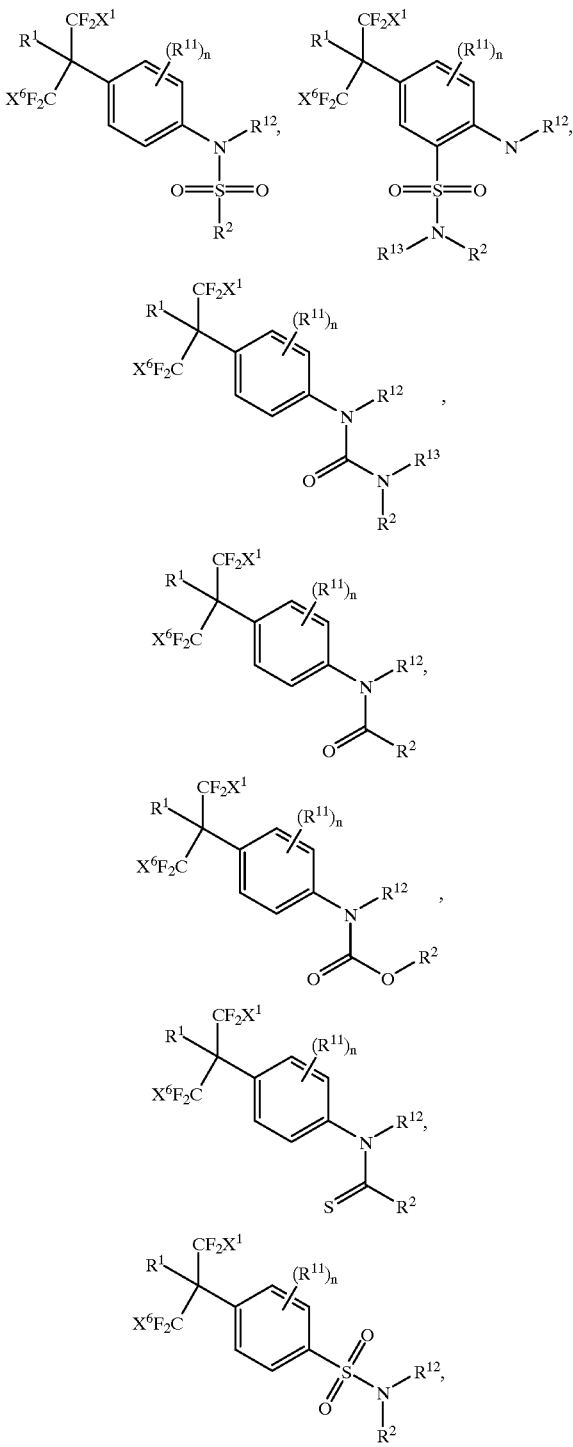

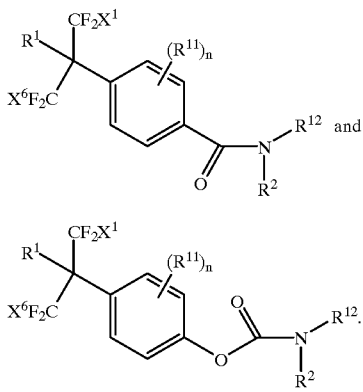

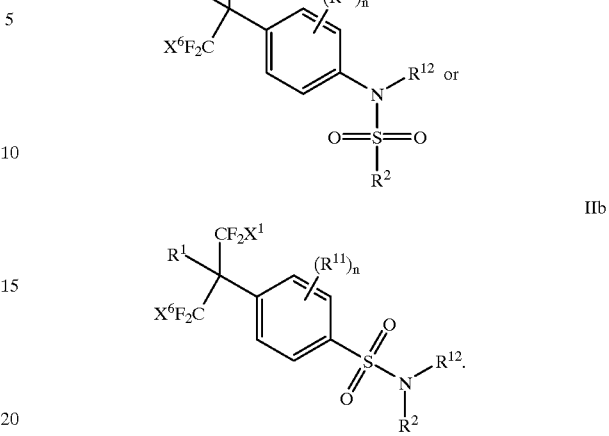

In this group of preferred embodiments, the various groups (e.g., $R^1$, $X^1$, $X^6$, $R^2$, $R^{11}$, $R^{12}$ and $R^{13}$) have the meanings indicated above with reference to Formula I. Preferably, $R^1$ is —OH or —$NH_2$, and $X^1$ and $X^6$ are each independently hydrogen or fluorine. Still further preferred within this group of embodiments are those in which $R^2$ is a substituted aryl group, more preferably a substituted phenyl or substituted thienyl group.

More preferably, the compositions will include a compound having a formula selected from the group consisting of

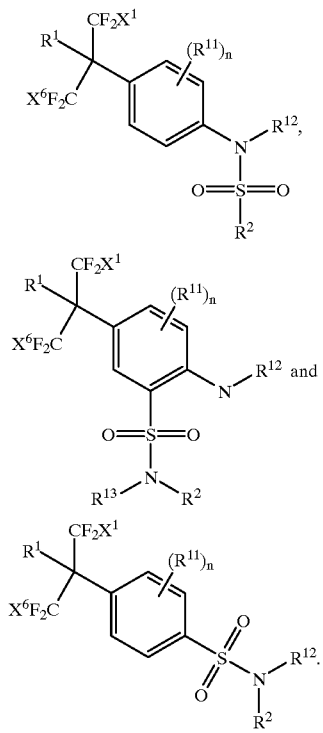

Most preferred, are those embodiments in which the compound has the formula:

Within the group of preferred compounds provided as Formulae IIa or IIb, at least three groupings of substituents are particularly preferred.

In a first group of preferred substituents, $R^1$ is —OH or —$NH_2$; $X^1$ and $X^6$ are each independently hydrogen or fluorine, $R^{12}$ is fluoro($C_1$-$C_4$)alkyl; and $R^2$ is aryl.

In a second group of preferred substituents, $R^1$ is —OH or —$NH_2$; $X^1$ and $X^6$ are each independently hydrogen or fluorine, $R^{12}$ is hydrogen or ($C_1$-$C_4$)alkyl; and $R^2$ is substituted or unsubstituted thienyl.

In a third group of preferred substituents, the compositions will include at least one compound of formula II in which $R^1$ is —OH or —$NH_2$; $X^1$ and $X^6$ are each independently hydrogen or fluorine, $R^{12}$ is ($C_1$-$C_4$)alkyl or($C_1$-$C_4$) heteroalkyl; and $R^2$ is phenyl substituted with at least one member selected from the group consisting of halogen, —CN, —$CF_3$, —O—($C_1$-$C_4$)alkyl, —C(O)—($C_1$-$C_4$)alkyl, —C(O)—O($C_1$-$C_4$)alkyl, —C(O)—NH($C_1$-$C_4$)alkyl and —C(O)N(($C_1$-$C_4$)alkyl)$_2$. Still further preferred are those embodiments in which $R^1$ is —OH; and $R^2$ is phenyl substituted with at least one member selected from —CN, —$CF_3$ and —O—($C_1$-$C_4$)alkyl.

Still other preferred embodiments have a formula selected from:

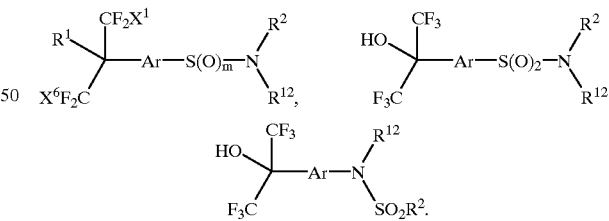

In each of the formula above, the groups Ar, $R^2$, $R^{12}$, and the subscript m have the meanings provided above with reference to formula I.

Further preferred compositions are those in which the compound above binds to the ligand binding domain of an LXR receptor, more preferably LXRα, with an affinity of at least 1 micromolar.

A number of the compounds used in the present compositions are novel. Accordingly, the present invention provides, in another aspect, compounds of Formula I, above, (wherein each of the recited substituents has the meaning provided above) with the proviso that when —Y—R² is —N(R¹²)S(O)ₘR² or —N(R¹²)C(O)N(R¹³)—R² and is attached to a position para to the quaternary carbon attached to Ar, and when R² is substituted or unsubstituted phenyl, benzyl or benzoyl, then i) at least one of R¹² or R¹³ is other than hydrogen or unsubstituted alkyl, or ii) R² is substituted with a moiety other than amino, acetamido, di(C₁–C₇)alkylamino, (C₁–C₇)alkylamino, halogen, hydroxy, nitro, or (C₁–C₇)alkyl, or iii) the R² phenyl group is trisubstituted in addition to the Y group.

Some of the compounds of Formula I may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of the invention may be labeled in a variety of ways. For example, the compounds may contain radioactive isotopes such as, for example, ³H (tritium) and ¹⁴C (carbon-14). Similarly, the compounds may be advantageously joined, covalently or noncovalently, directly or through a linker molecule, to a wide variety of other compounds, which may provide pro-drugs or function as carriers, labels, adjuvents, coactivators, stabilizers, etc. Such labeled and joined compounds are contemplated within the present invention.

In yet another aspect, the present invention provides a method for modulating the action of an LXR receptor, preferably LXRα, in a cell. According to this method, the cell is contacted with a sufficient concentration of a composition containing a compound of formula I for either an agonistic or antagonistic effect to be detected. In preferred embodiments, the composition contains an amount of the compound which has been determined to provide a desired therapeutic or prophylactic effect for a given LXR-mediated condition.

In still another aspect, the present invention provides methods for the treatment of pathology such as hypercholesterolemia, atherosclerosis, and hyperlipoproteinemia using pharmaceutical compositions containing compounds of the foregoing description of the general Formula I. Briefly, this aspect of the invention involves administering to a patient an effective formulation of one or more of the subject compositions. In other embodiments, the compound of Formula I can be administered in combination with other anti-hypercholesterolemic agents (e.g., a bile acid sequestrant, nicotinic acid, fabric acid derivatives or HMG CoA reductase inhibitors), or in combination with other agents that affect cholesterol or lipid metabolism.

Synthesis

Compounds of the present invention can be prepared using readily available starting materials or known intermediates. Scheme 1 provides a variety of synthesis avenues for the production of the subject compounds. One of skill in the art will understand that additional methods are also useful.

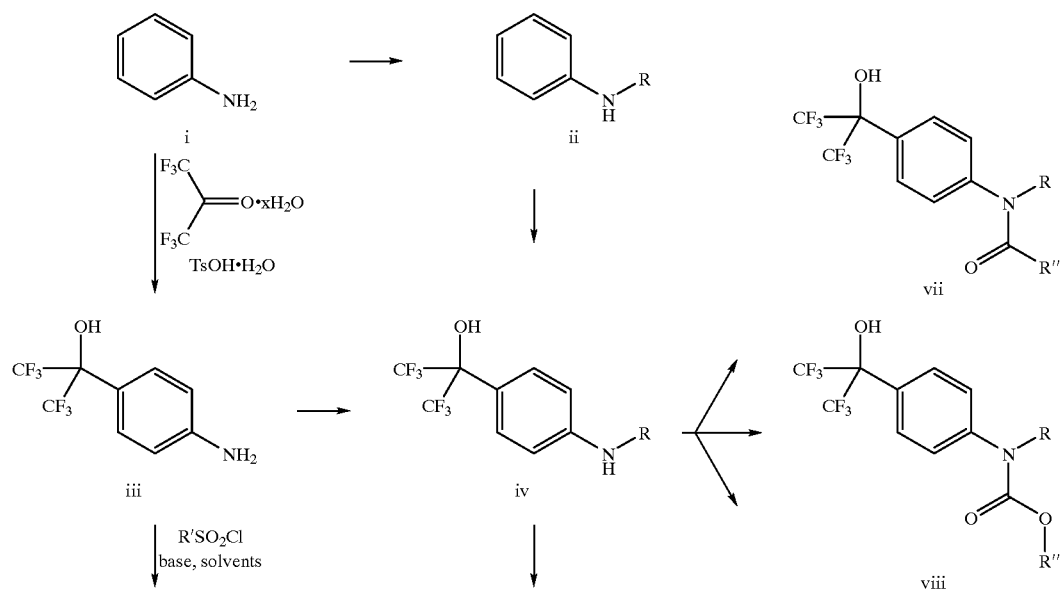

SCHEME 1

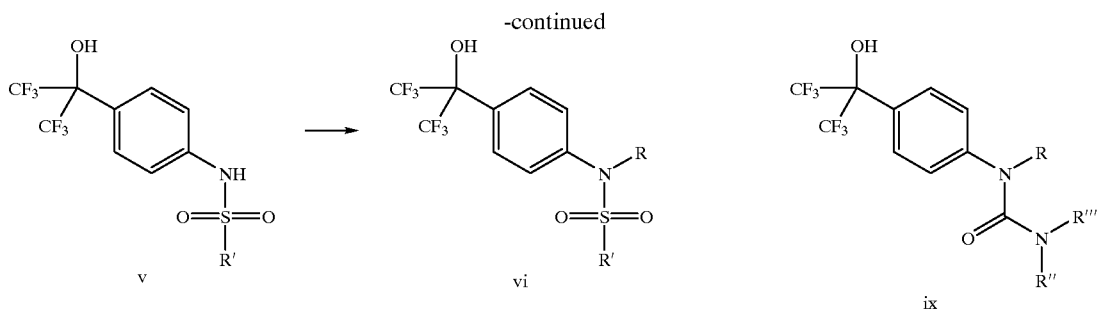

-continued v  vi  ix

As shown in Scheme 1, aniline i (as representative of substituted anilines and other arylamnines) can either be alkylated, acylated or arylated (general addition of R group) to form ii, or the aromatic ring can derivatized with, for example, hexafluoroacetone to form iii. Treatment of iii with an appropriate alkylating group, acylating group or arylating group provides iv, which can be sulfonylated with, for example, an appropriate sulfonyl halide to form vi. Alternatively, the aniline derivative iii can be sulfonylated to form v, which can then be alkylated or acylated to form compounds of formula vi.

Other compounds of the present invention can be formed by treating the substituted aniline iv (or, alternatively, iii), with reagents suitable for the formation of amides vii, carbarnates viii, and ureas ix. A variety of reagents are usefull in the above scheme and can be found in, for example, March, *Advanced Organic Chemistry* 4th Ed., John Wiley & Sons, New York, N.Y. (1992). Preferred reagents and conditions are also found in the Examples below.

Methods for the preparation of compounds in which a sulfonamide linkage has the reverse orientation are provided in Scheme 2. According to Scheme 2, a substituted benzenesulfonamide x (prepared from a substituted benzenesulfonyl chloride and an amine or an aniline) can be converted to the desired alcohol xi upon treatment with $CF_3$-TMS in the presence of tetrabutylammnonium fluoride in tetrahydrofiuran. Alternatively, a halo-substituted benzenesulfonamide xii (similarly prepared from a halo-substituted benzenesulfonyl chloride and an amine or an aniline) can be coverted to the trifluoromethylketone xiii upon treatment with n-butyllithium followed by methyl trifluoroacetate at $-78°$ C. Subsequent treatment of xiii with $CF_3$-TMS in the presence of tetrabutylammonium fluoride in tetrahydrofuiran provides compounds of formula xi.

SCHEME 2

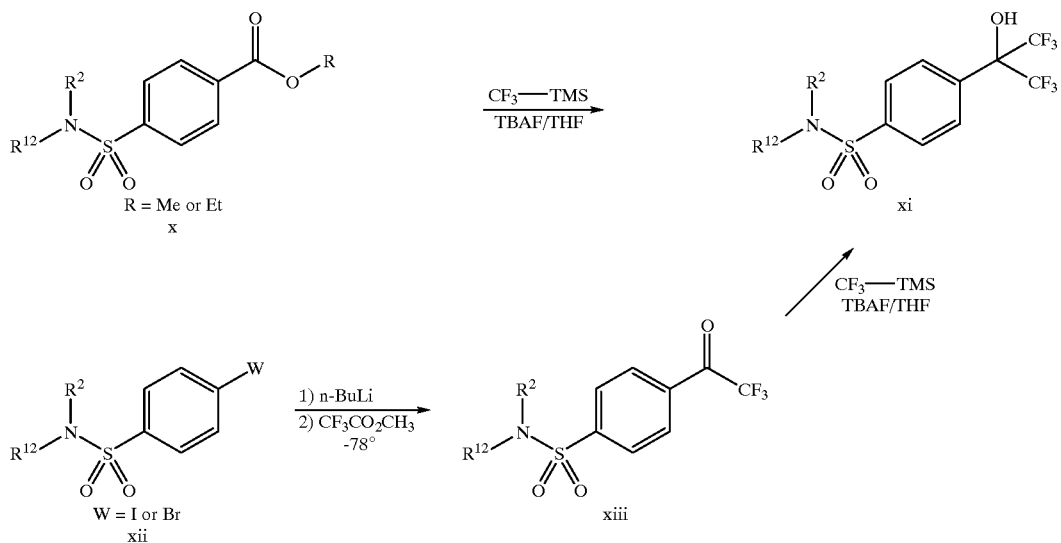

Solid Phase Synthesis

Figure 2:
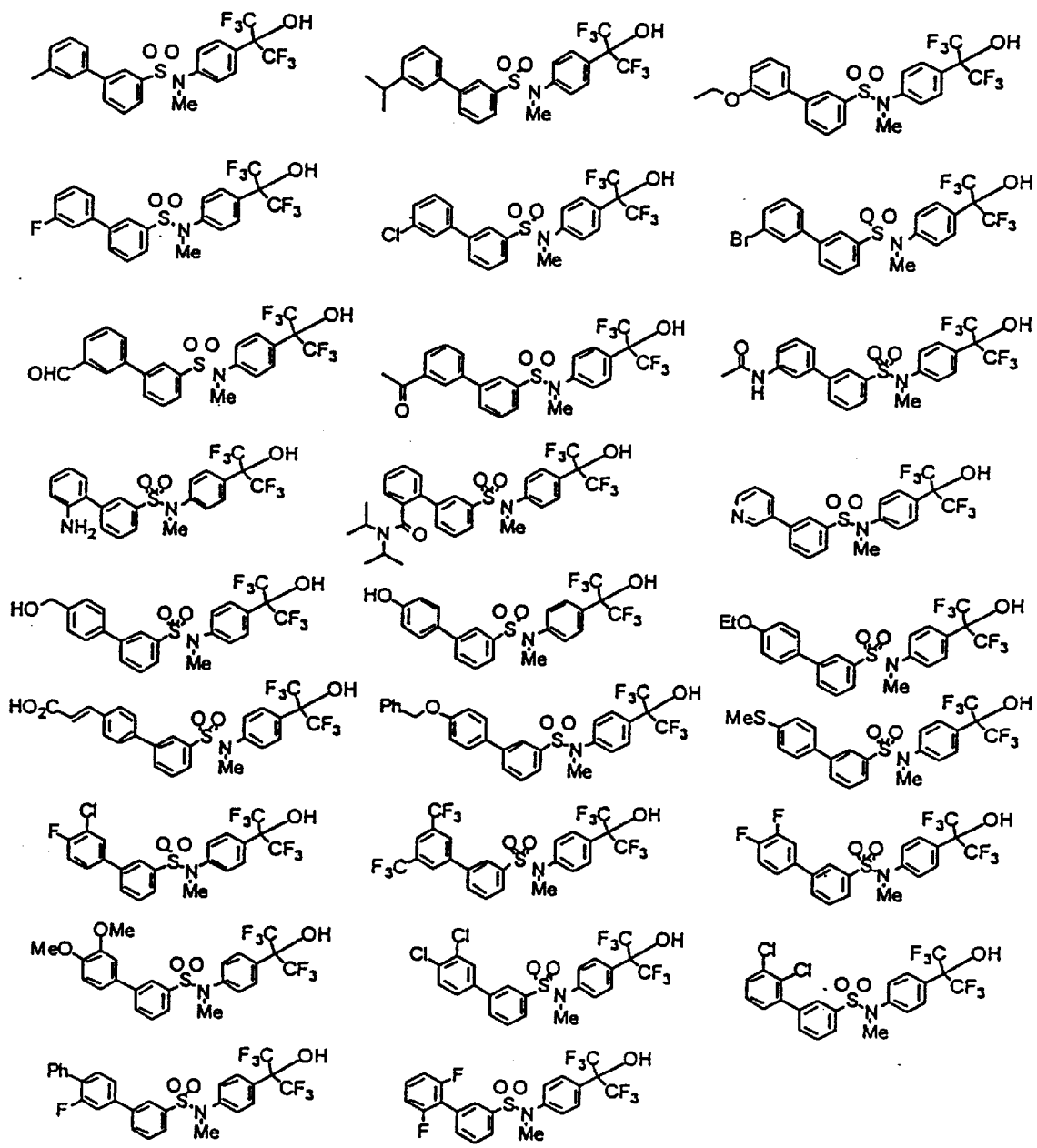

Scheme 3 provides one method for preparing compounds of the present invention using solid phase synthesis. In this method, an initial compound is further elaborated using a Suzuki coupling to include additional aryl substituents on a phenyl ring adjacent to the sulfonyl moiety. According to the method outlined in Scheme 2, an activated resin (e.g., 4-(bromomethyl)phenoxyethyl polystyrene from Nova Biochem) is treated with a parent compound to be derivatized (e.g., compound xiv) to provide a tethered reactive species xv. Suzuki coupling conditions are then employed to attach an aromatic moiety (Ar) in place of the bromine substituent (see Step 2) and provide a modified target compound tethered to the support (xvi). The modified target compound (xvii) is then cleaved from the support and filtered through silica gel. FIGS. 1 and 2 provide structures of compounds prepared using this methodology. The aryl boronic acids used in the Suzuki coupling were from commercial sources (e.g., Aldrich Chemical Co., Milwaukee, Wis., USA; Lancaster, Digital Specialty Chemicals Inc., and Combi-Blocks).

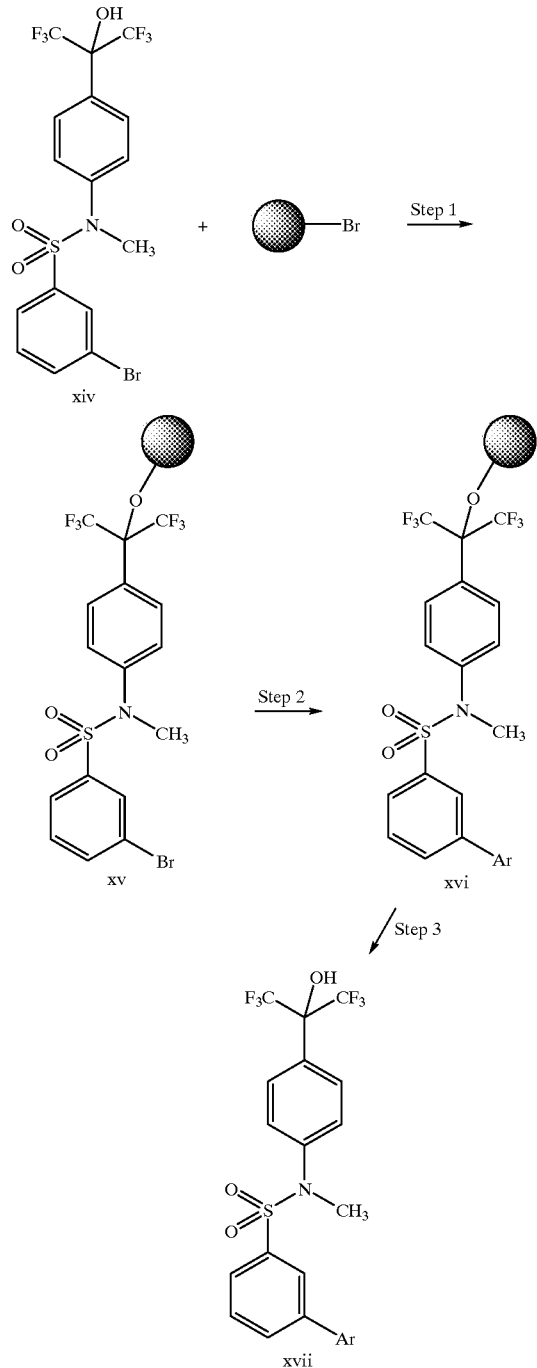

SCHEME 3

Analysis of Compounds

Representative compounds and compositions were demonstrated to have pharmacological activity in in vitro and in vivo assays, e.g., they are capable of specifically modulating a cellular physiology to reduce an associated pathology or provide or enhance a prophylaxis.

Certain preferred compounds and compositions are capable of specifically regulating LXR. Compounds may be evaluated in vitro for their ability to activate LXR receptor function using biochemical assays (see co-pending applications Ser. Nos. 08/975,614 (filed Nov. 21, 1997) and 09/163,713 (filed Sep. 30, 1998)), or in cell-based assays such as that described in Lehnman, et al. (*J. Biol. Chem.* 1997, 272(6), 3137–3140). Alternatively, the compounds and compositions can be evaluated for their ability to increase or decrease gene expression modulated by LXR, using western-blot analysis. Established animal models to evaluate hypocholesterolemic effects of the compounds are also known in the art. For example, compounds disclosed herein can lower cholesterol levels in hamsters fed a high-cholesterol diet, using a protocol similar to that described in Spady et al. (*J. Clin. Invest.* 1988, 81, 300), Evans et al. (*J. Lipid Res.* 1994, 35, 1634), and Lin et al (*J. Med. Chem.* 1995, 38, 277). Still further, LXRα animal models (e.g., LXRα (+/−) and (−/−) mice) can be used for evaluation of the present compounds and compositions (see, for example, Peet, et al. *Cell* 1998, 93, 693–704).

Accordingly, as used herein, the term "LXR-modulating amount" refers to that amount of a compound that is needed to produce a desired effect in any one of the cell-based assays, biochemical assays or animal models described above. Typically, an LXR-modulating amount of a compound will be at least that amount which exhibits an $EC_{50}$ in a reporter-gene cell-based assay (relative to an untreated control).

Formulation and Administration of Compounds and Pharmaceutical Compositions

The invention provides methods of using the subject compounds and compositions to treat disease or provide medicinal prophylaxis, to activate LXR receptor function in a cell, to reduce blood cholesterol concentration in a host, to slow down and/or reduce the abnormal cellular proliferation including the growth of tumors, etc. These methods generally involve contacting the cell or cells with or administering to a host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other hypocholesterolemic therapeutic or prophylactic agents, different from the subject compounds. In many instances, administration in conjunction with the subject compositions enhances the efficacy of such agents. Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, and simvastatin; gemfibrozil and other fibric acids, such as clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to use labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES $^1$H-NMR spectra were recorded on a Varian Gemini 400 MHz NMR spectrometer. Significant peaks are tabulated and typically include: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). Starting materials in the synthesis examples below are either available from commercial sources such as Aldrich Chemical Co., Milwaukee, Wis., USA, or via literature procedures. Abbreviations used in the examples below have their accepted meanings in the chemical literature. For example, THF (tetrahydrofuran), Et$_2$O (diethyl ether), MeOH (methanol), CH$_2$Cl$_2$ (methylene chloride), LDA (lithium diisopropylamide), MeCN (acetonitrile), and DMAP (4-dimethyaminopyridine).

Example 1

This example illustrates preparation of compound 1.

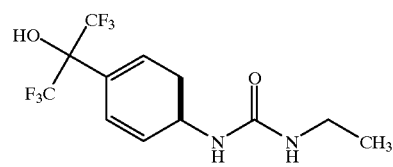

1

Commercially available 4-(1,1,1,3,3,3-hexafluoro-2-hydroxyisopropyl)aniline (1.93 mmol, 500 mg, Lancaster Synthesis, LTD, Teaneck, N.J., USA) was dissolved in THF (8 mL) and triethylamine (3.86 mmol, 391 mg) was added, followed by ethyl isocyanate (1.93 mmol, 137 mg). The mixture was heated at 60° C. for 24 hours. The resulting mixture was diluted with CH$_2$Cl$_2$ and quenched with water. The organic layer was separated and dried with MgSO$_4$, the solvent was evaporated and the crude product was recrystallized from MeOH/CH$_2$Cl$_2$ to afford 353 mg of 1.

mp 170–172° C.

$^1$H-NMR(CD$_3$OD): (7.58 (d, J=8.8 Hz, 2H), 7.42 (d, J=8.8 Hz, 2H), 3.23 (m, 2H), 1.15 (t, J=7.28 Hz, 3H). MS (ES+): 331 (M+H, 100). Anal. Calcd. for C$_{12}$H$_{12}$N$_2$F$_6$O$_2$: C, 43.78; H, 3.66; N, 8.48. Found: C, 48.02; H, 3.72; N, 8.36.

Example 2

This example illustrates preparation of sulfonamide 2.

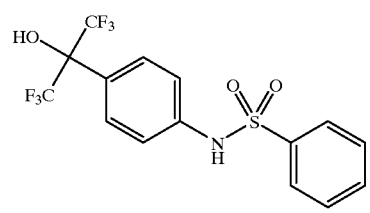

2

To a solution of 4-(hexafluoro-2-hydroxyisopropyl) aniline (77.2 mmol, 20 g) in MeOH (200 mL) was added benzenesulfonyl chloride (61.74 mmol, 11.01 g). The mixture was stirred at ambient temperature for 2.5 hours. The solvent was evaporated under reduced pressure and the crude product was dissolved in Et$_2$O and washed with 3N HCl. The organic layer was separated, the solvent was evaporated and the crude product was purified by silica column chromatography using 25% MeOH/CH$_2$Cl$_2$ to afford 14.7 g of product.

mp 111–113° C.

$^1$H-NMR(CDCl$_3$): δ 7.16 (d, J=7.16 Hz, 2H), 7.56 (m, 2H), 7.45 (m, 2H), 7.14 (dd, J=2.12, 6.84 Hz, 2H), 6.89 (s, 1H), 3.41 (s, 1H). MS (ES–): 398 (M–H, 100). Anal. Calcd. for C$_{15}$H$_{11}$F$_6$NO$_3$S: C, 45.12; H, 2.78; N, 3.51. Found: C, 45.02; H, 2.90; N, 3.54.

The following compounds were prepared in a manner similar to that described above.

2.1

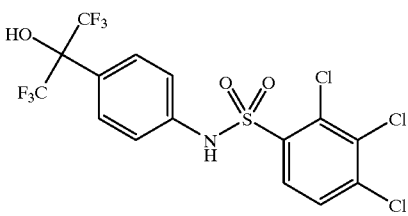

2.1 mp 205–209° C. $^1$H-NMR(d$_6$-DMSO): δ 11.1 (bs, 1H), 8.61 (s, 1H), 8.08 (d, J=8.68 Hz, 1H), 7.89 (d, J=8.68 Hz, 1H), 7.55 (d, J=8.68 Hz, 2H), 7.20 (dd, J=1.96, 6.88 Hz, 2H). MS (ES–): 501 (M–H, 100). Anal. Calcd. for C$_{15}$H$_8$Cl$_3$F$_6$NO$_3$S: C, 35.84; H, 1.60; N, 2.79. Found: C, 36.42; H, 1.85; N, 2.66.

2.2

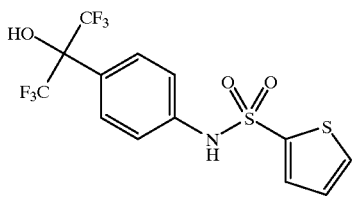

2.2 mp 113–115° C. $^1$H-NMR(CD$_3$OD): δ 7.71 (m, 1H), 7.61–7.54 (m, 3H), 7.24 (m, 2H), 7.06 (m, 1H. MS (ES+): 404 (M+H$^+$, 100). Anal. Calcd. for C$_{13}$H$_9$F$_6$NO$_3$S: C, 38.52; H, 2.24; N, 3.46. Found: C, 38.79; H, 2.28; N, 3.28.

Example 3

This example illustrates the preparation of (3) via N-methylation of (2).

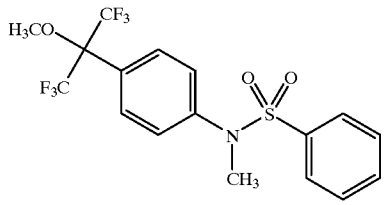

3

To N-[4-[2,2,2-trifluoro-1-hydroxy-1-(trifluoromethyl) ethyl]phenyl-benzenesulfonamide (2) (2.5 g), in DMF (60 mL) was added K$_2$CO$_3$ (1.6 g) and methyl iodide (0.64 mL). The reaction was stirred at room temperature for 1.5 hours, then worked up using standard methods, and the crude product was purified by column chromatography to afford the 3.5 g of the title compound.

mp 79–81° C. $^1$H-NMR(CDCl$_3$): δ 7.63–7.45 (m, 7H), 7.26 (m, 2H), 3.50 (s, 3H), 3.22 (s, 3H). MS (ES+): 428 (M+H, 100). Anal. Calcd. for C$_{17}$H$_{15}$F$_6$NO$_3$S: C, 47.78; H, 3.54; N, 3.20; S, 7.50. Found: C, 47.87; H, 3.61; N, 3.27; S, 7.55.

Example 4

This example illustrates preparation of sulfonamide, 4.

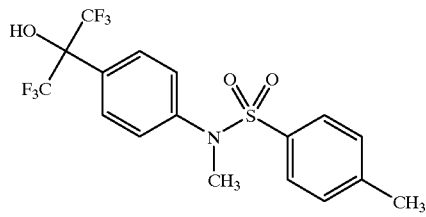

4

To N-methyl-4-(hexafluoro-2-hydroxyisopropyl)aniline (0.915 mmol, 250 mg) prepared as reported by Gilbert et al. (J. Org. Chem., 1965, 30, 1001) in MeOH (2.5 mL) was added p-toluenesulfonyl chloride (0.763 mmol, 145 mg). The reaction was stirred overnight at ambient temperature and the solvent was evaporated under reduced pressure. The crude product was dissolved in CH$_2$Cl$_2$ and washed with 3N HCl. The organic layer was separated, the solvent evaporated and the crude product was purified by silica column chromatography to afford 130 mg of 4.

mp 98–101° C. $^1$H-NMR(CDCl$_3$): δ 7.64 (d, J=8.4 Hz, 2H), 7.39 (d, J=8.16 Hz, 2H), 7.21 (m, 4H), 3.16 (s, 3H), 2.40 (s, 3H). MS (ES–): 426 (M–H, 100). Anal. Calcd. for C$_{17}$H$_{15}$F$_6$NO3S: C, 47.78; H, 3.54; N, 3.20; S, 7.50. Found: C, 48.02; H, 3.52; N, 3.20; S, 7.57.

The following compounds were prepared using methods similar to those described in this and the preceding examples, with the appropriately substituted arylsulfonyl chlorides or alkylsulfonyl chlorides.

4.1

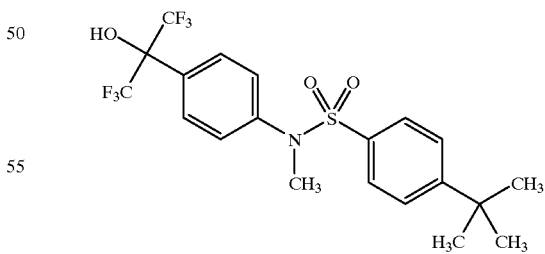

4.1 mp 132–134° C. $^1$H-NMR(CDCl$_3$): δ 7.64 (d, J=8.8 Hz, 2H), 7.44 (s, 4H), 7.23 (d, J=8.8 Hz, 2H), 3.18 (s, 3H), 1.32 (s, 9H). MS (ES–): 468 (M–H, 100). Anal. Calcd. for C$_{20}$H$_{21}$F$_6$NO$_3$S: C, 51.17; H, 4.51; N, 2.98; S, 6.83. Found: C, 51.32; H, 4.47; N, S, 6.76.

4.2

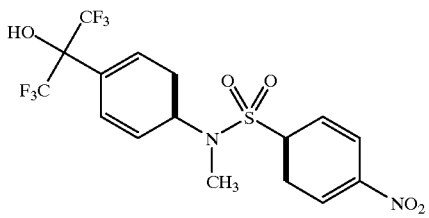

4.2 mp 104–106° C. ¹H-NMR(CDCl₃): δ 8.30 (d, J=8.9 Hz, 2H), 7.70 (m, 4H), 7.20 (d, J=9 Hz, 2H), 3.24 (s, 3H). MS (ES-): 457 (M-H, 100). Anal. Calcd. for $C_{16}H_{12}F_6N_2O_5S$: C, 41.93; H, 2.64; N, 6.11; S, 7.00. Found: C, 42.11; H, 2.71; N, 5.95; S, 6.85.

4.3

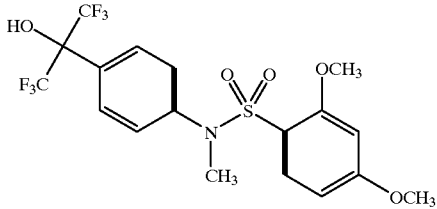

4.3 mp 65–69° C. ¹H-NMR(CDCl₃): δ 7.63 (d, J=8.7 Hz, 2H), 7.34 (m, 3H), 7.03 (dd, 8.9, 3.0 Hz, 1H), 6.85 (d, J=9.04 Hz, 1H), 3.74 (s, 3H), 3.54 (s, 3H), 3.32 (s, 3H). MS (ES+): 474 (M+H, 100). Anal. Calcd. for $C_{18}H_{17}F_6NO_5S$: C, 45.67; H, 3.62; N, 2.96; S, 6.77. Found: C, 45.21; H, 3.71; N, 2.93; S, 6.58.

4.4

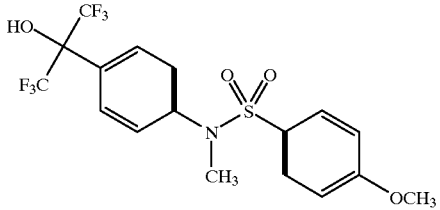

4.4 mp 109–111° C. ¹H-NMR(CDCl₃): δ 8.4 (d, J=8.4 Hz, 2H), 7.44 (d, J=8.8 Hz, 2H), 7.21 (d, J=8.9 Hz, 2H), 6.90 (d, J=8.9 Hz, 2H), 3.84 (s, 3H), 3.16 (s, 3H). MS (ES+): 444 (M+H, 100). Anal. Calcd. for $C_{17}H_{15}F_6NO_4S$: C, 46.05; H, 3.41; N, 3.16; S, 7.23. Found: C, 45.84; H, 3.41; N, 3.12; S, 7.14.

4.5

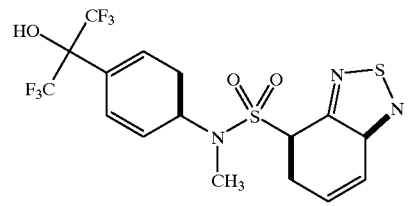

4.5 mp 175–180° C. ¹H-NMR(CDCl₃): δ 8.21 (d, J=8.8 Hz, 1H), 8.12 (d, J=7.6 Hz, 1H), 7.64 (dd, J=7.08, 8.8 Hz, 1H), 7.56 (d, J=8.76 Hz, 2H), 7.21 (d, J=8.5 Hz, 2H), 3.53 (s, 3H). MS (ES-): 470 (M-H, 100). Anal. Calcd. for $C_{16}H_{11}F_6N_3O_3S_2$: C, 40.77; H, 2.35; N, 8.91; S, 13.60. Found: C, 40.64; H, 2.22; N, 8.84; S, 13.78.

4.6

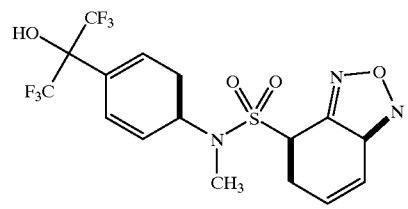

4.6 mp 113–115° C. ¹H-NMR(CDCl₃): δ 8.06 (dd, J=9.12, 0.7 Hz, 1H), 7.85 (dd, J=6.88, 0.8 Hz, 1H), 7.60 (d, J=9.0 Hz, 2H), 7.46 (dd, J=9.08, 6.84 Hz, 1H), 7.25 (d, J=9.0 Hz, 2H), 3.55 (s, 3H).

4.7

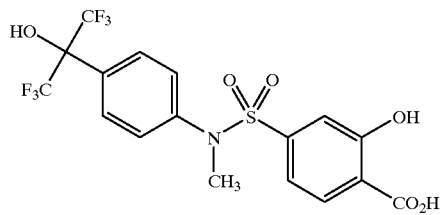

4.7 mp 195–197° C. ¹H-NMR(d₆-DMSO): δ 8.76 (s, 1H), 7.77 (d, J=2.5 Hz, 1H), 7.64 (d, J=8.44 Hz, 2H), 7.56 (dd, J=8.8, 2.5 Hz, 1H), 7.30 (d, J=8.9 Hz, 2H), 7.07 (d, J=9.0 Hz, 1H), 3.13 (s, 3H).

4.8

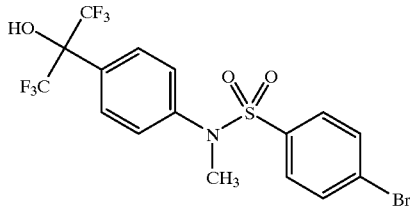

4.8 mp 90–91° C. ¹H-NMR(CDCl₃): δ 7.66 (d, J=8.5 Hz, 2H), 7.58 (d, J=8.6 Hz, 2H), 7.37 (d, J=8.64 Hz 2H), 7.23 (d,

J=8.8 Hz, 2H), 3.19 (s, 3H). MS (ES−): 491 (M−H, 100), 489 (M−H, 100). Anal. Calcd. for $C_{16}H_{12}BrF_6NO_3S$: C, 39.04; H, 2.46; N, 2.85; S, 6.51; Br, 16.23. Found: C, 39.24; H, 2.44; N, 2.71; S, 6.52; Br, 16.38.

4.9 mp 98–99° C. $^1$H-NMR(CDCl$_3$): δ 7.67 (d, J=9 Hz, 2H), 7.54 (m, 2H), 7.21 (d, J=9.0 Hz, 2H), 7.13 (m, 2H), 3.20 (s, 3H). MS (ES−): 430 (M−H, 100). Anal. Calcd. for $C_{16}H_{12}F_7NO_3S$: C, 44.55; H, 2.80; N, 3.25; S, 7.43. Found: C, 44.54; H, 2.83; N, 3.18; S, 7.39.

4.10 mp 98–100° C. $^1$H-NMR(CDCl$_3$): δ 8.8 (d, J=8.8 Hz, 2H), 7.55 (m, 1H), 7.49 (s, 1H), 7.38 (m,2H), 7.21 (d, J=9 Hz, 2H), 3.21 (s, 3H). MS (ES−): 446 (M−H, 100). Anal. Calcd. for $C_{16}H_{12}ClF_7NO_3S$: C, 42.92; H, 2.70; N, 3.13; S, 7.16; Cl, 7.92. Found: C, 42.90; H, 2.62; N, 3.02; S, 7.15; Cl, 8.04.

4.11 mp 114–116° C. $^1$H-NMR(CDCl$_3$): δ 7.94 (d, J=6.5 Hz, 1H), 7.62 (d, J=8.8 Hz, 2H), 7.48 (m, 2H), 7.33 (m, 3H), 3.42 (s, 3H). MS (ES−): 446 (M−H, 100). Anal. Calcd. for $C_{16}H_{12}ClF_7NO_3S$: C, 42.92; H, 2.70; N, 3.13; S, 7.16; Cl, 7.92. Found: C, 42.84; H, 2.62; N, 3.02; S, 7.24; Cl, 8.03.

4.12 mp 124–126° C. $^1$H-NMR(CDCl$_3$): δ 7.68 (m, 4H), 7.42 (m, 1H), 7.33 (m, 1H), 7.21 (d, J=8.08 Hz, 2H), 3.21 (s, 3H). Anal. Calcd. for $C_{16}H_{12}BrF_6NO_3S$: C, 39.04; H, 2.46; N, 2.85; S, 6.51; Br, 16.23. Found: C, 39.04; H, 2.38; N, 2.75; S, 6.45; Br, 16.36.

4.13 mp 79–81° C. $^1$H-NMR(CDCl$_3$): δ 7.83 (d, J=7.0 Hz, 1H), 7.74 (d, J=7.0 Hz, 1H), 7.66 (m,3H), 7.63 (m, 1H), 7.18 (d, J=7.0 Hz, 2H), 3.20 (s, 3H). MS (ES−): 480 (M−H, 100). Anal. Calcd. for $C_{17}H_{12}F_9NO_3S$: C, 42.42; H, 2.51; N, 3.91; S, 6.66. Found: C, 42.66; H, 2.48; N, 2.96; S, 6.49.

4.14 mp 135–137° C. MS (ES−): 430 (M−H, 100). Anal. Calcd. for $C_{16}H_{12}F_7NO_3S$: C, 44.55; H, 2.80; N, 3.25; S, 7.43. Found: C, 44.45; H, 2.76; N, 3.17; S, 7.48.

4.15 mp 135–137° C. MS (ES−): 430 (M−H , 100). Anal. Calcd. for $C_{16}H_{12}F_7NO_3S$ : C, 44.55; H, 2.80; N, 3.25; S, 7.43. Found: C, 44.65; H, 2.84; N, 3.17; S, 7.39.

4.16

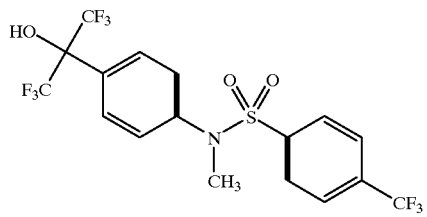

mp 115–118° C. ¹H-NMR(CDCl₃): δ 7.74–7.65 (m, 6H), 7.22 (d, J=6.72 Hz, 2H), 3.22 (s, 3H). MS (ES–): 430 (M–H, 100). Anal. Calcd. for $C_{17}H_{12}F_9NO_3S$: C, 42.42; H, 2.51; N, 3.91; S, 6.66. Found: C, 42.24; H, 2.42; N, 2.87; S, 6.65.

4.17

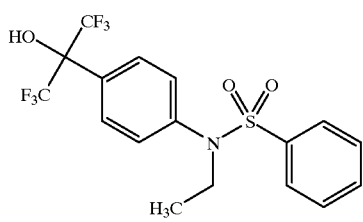

mp 88–89° C. ¹H-NMR(d₆-DMSO): δ 8.80 (s, 1H), 7.75–7.50 (m, 7H), 7.25 (m, 2H), 3.60 (m, 2H), 3.31 (s, 3H), 0.977 (m, 3H). MS (ES+): 428 (M+H, 100).

4.18

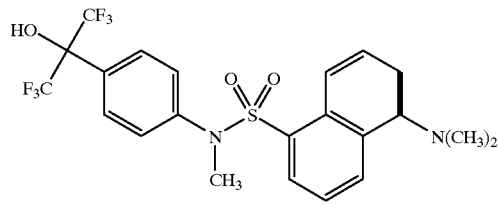

¹H-NMR(CD₃OD): δ 8.57 (dd, J=1.12, 8.56 Hz, 1H), 8.13 (m, 1H), 8.36 (m, 1H), 7.61–7.52 (m, 3H), 7.23–7.15 (m, 4H), 3.22 (s, 3H), 2.84 (s, 6H). MS (ES+): 507 (M+H, 100).

4.19

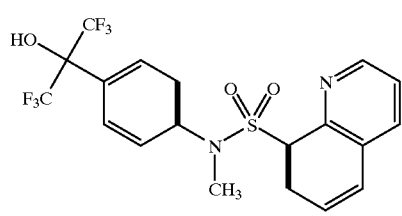

mp 180–183° C. ¹H-NMR(CD₃OD): δ 8.92 (dd, J=4.2, 1.76 Hz, 1H), 8.39 (dd, J=8.36, 1.72 Hz, 1H), 8.35 (dd, J=1.36, 7.36 Hz, 1H), 8.17 (dd, J=1.32, 8.2 Hz, 1H), 7.63 (m, 2H), 7.52 (m, 2H), 7.25 (dd, J=6.88, 2.0 Hz, 2H), 3.61 (s, 3H). MS (ES+): 465 (M+H, 100).

4.20

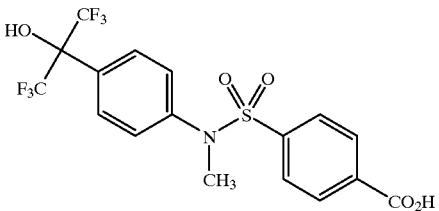

mp 208–210° C. ¹H-NMR(CD₃OD): δ 8.12 (d, J=8.56 Hz, 2H), 7.70 (d, J=8.72 Hz, 2H), 7.64 (d, J=8.6 Hz, 2H), 7.26 (d, J=8.96 Hz, 2H), 3.24 (s, 3H). MS (ES–): 456 M–H, 100).

4.21

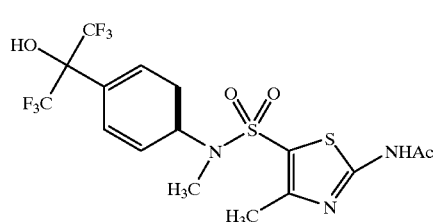

mp 102–106° C. ¹H-NMR(CD₃OD): δ 7.72 (d, J=8.4 Hz, 2H), 7.36 (dd, J=2.12, 6.88 Hz, 2H), 3.31 (s, 3H), 2.22 (s, 3H), 1.86 (s, 3H). MS (ES+): 492 (M+H, 100).

4.22

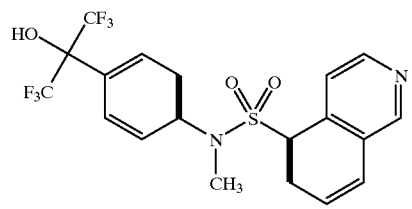

mp 204–206° C. ¹H-NMR(CD₃OD): δ 9.30 (s, 1H), 8.41 (m, 2H), 8.13 (d, J=1.5 Hz, 1H), 7.83 (t, J=8.03 Hz, 1H), 7.74 (d, J=6.32 Hz, 1H), 7.60 (d, J=8.8 Hz, 2H), 7.20 (dd, J=2.08, 6.84 Hz, 2H), 3.24 (s, 3H). MS (ES+): 465 (M+H, 50).

4.23

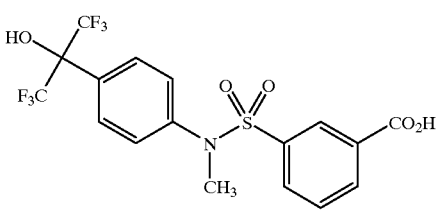

mp 199–202° C. ¹H-NMR(CD₃OD): δ 8.26 (m, 1H), 7.71 (m, 3H), 7.63 (t, J=8.12 Hz, 1H), 7.25 (dd, J=2.12, 6.8 Hz, 2H), 3.23 (s, 3H). MS (ES+): 458 (M+H, 100).

4.24

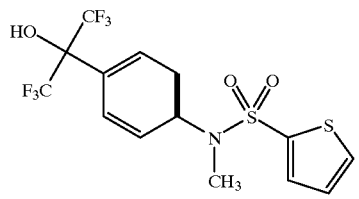

4.24 mp 133–136° C. $^1$H-NMR(CD$_3$OD): δ 7.82 (dd, J=5.08, 1.28 Hz, 1H), 7.70 (d, J=8.52 Hz, 2H), 7.38 (dd, J=1.2, 3.74 Hz, 1H), 7.28 (m, 2H), 7.16 (m, 1H), 3.26 (s, 3H). MS (ES+): 420 (M+H, 100).

4.25

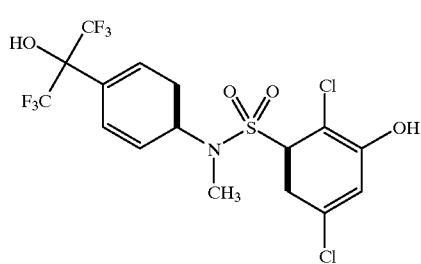

4.25 mp 120–122° C. $^1$H-NMR(CD$_3$OD): δ 7.68 (d, J=8.72 Hz, 2H), 7.61 (s, 1H), 7.43 (s, 1H), 7.38 (m, 2H), 3.40 (s, 3H). MS (ES–): 487 (M–H, 100).

4.26

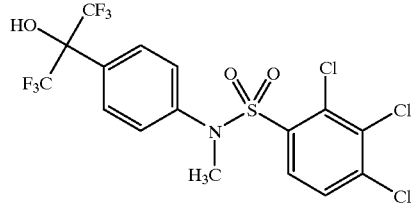

4.26

Oil. $^1$H-NMR(CD$_3$OD): δ 7.90 (m, 1H), 7.70–7.63 (m, 3H), 7.40 (m, 2H), 3.42 (s, 3H). MS (ES–): 515 (M–H, 100).

4.27

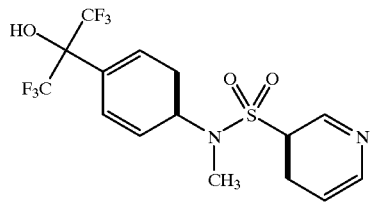

4.27 mp 148–149° C. $^1$H-NMR(CD$_3$OD): δ 8.80 (d, J=4.76 Hz, 1H), 8.64 (s, 1H), 7.96 (m, 1H), 7.72 (d, J=8.72 Hz, 2H), 7.59 (m, 1H), 7.28 (d, J=9 Hz, 2H), 3.26 (s, 3H). MS (ES–): 413 (M–H, 100).

4.28

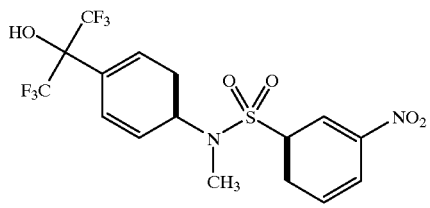

4.28 mp 130–134° C. $^1$H-NMR(CD$_3$OD): δ 7.64 (m, 1H), 7.54 (m, 6H), 7.12 (dd, J=6.64, 2.12 Hz, 2H), 3.18 (s, 3H). MS (ES+): 459 (M+H$^+$, 100). Anal. Calcd. for C$_{16}$H$_{12}$F$_6$N$_2$O$_5$S: C, 41.93; H$_{12.64}$; N, 6.11. Found: C, 41.64; H, 2.69; N, 6.10.

4.29

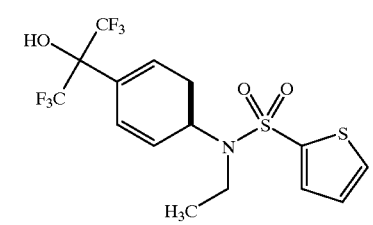

4.29 mp 83–86° C. $^1$H-NMR(CD$_3$OD): δ 7.82 (m, 1H), 7.73 (m, 2H), 7.40 (m, 1H), 7.24 (m, 2H), 7.15 (m, 1H), 3.71 (q, J=7.16, 14.24 Hz, 2H), 1.09 (t, J=7.24 Hz, 3H). MS (ES+): 434 (M+H$^+$, 100).

4.30

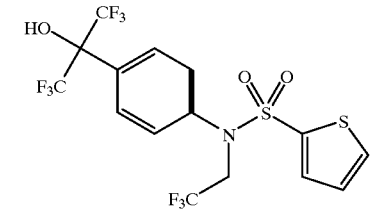

4.30 mp 87–89° C. $^1$H-NMR(CD$_3$OD): δ 8.86 (s, 1H), 8.07 (dd, J=1.28, 4.92 Hz, 1H), 7.71 (m, 2H), 7.36 (m, 2H), 7.28 (m, J=3.84, 4.98 Hz, 1H), 4.61 (q, J=8.8, 17.6 Hz, 2H).

4.31

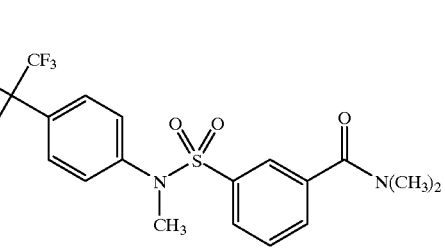

4.31 mp 142–145° C. $^1$H-NMR(CD$_3$OD): δ 7.68 (m, 5H), 7.44 (s, 1H), 7.28 (m, 2H), 3.24 (s, 3H), 3.06 (s, 3H), 2.84 (s, 3H). Anal. Calcd. for C$_{19}$H$_{18}$F$_6$N$_2$O$_4$S: C, 47.11; H, 3.75; N, 5.78. Found: C, 47.19; H, 3.75; N, 5.77.

4.32

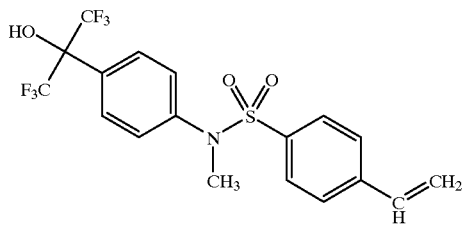

4.32

¹H NMR (CDCl₃): δ 7.70 (d, J=8.4 HZ, 2H), 7.50 (m, 4H), 7.25 (d, J=8.4 Hz, 2H), 6.78 (dd, J=16.0, 11.0 Hz, 1H), 5.90 (d, J=16.0 Hz, 1H), 5.48 (d, J=11.0 Hz, 1H), 3.55 (s, 1H), 3.28 (s, 3H). MS (ES−): 438 (M−H, 100).

4.33

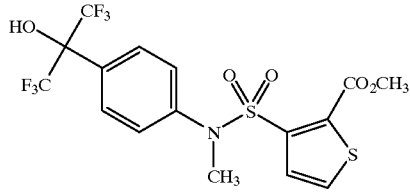

4.33

¹H NMR (CDCl₃): δ 7.70 (d, J=8.5 Hz, 2H), 7.42 (d, J=5.0 Hz, 1H), 7.35 (d, J=8.5 Hz, 2H), 7.25 (d, J=5 Hz, 1H), 3.75 (s, 3H), 3.65 (s, 1H), (s, 3H). MS (ES+): 478 (M+H, 100).

4.34

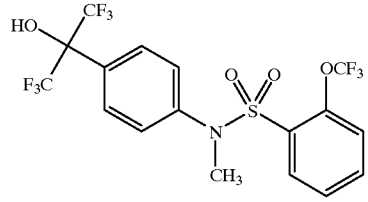

4.34

¹H NMR (CDCl₃): δ 7.91 (d, J=7.5 Hz, 1H), 7.68 (d, J=8.4 Hz, 2H), 7.63 (t, J=8.4 Hz, 1H), 7.36 (t, J=7.5 Hz, 2H), 7.32 (d, J=8.4 Hz, 2H), 3.60 (s, H), 3.30 (s, 3H). MS (ES+): 498 (M+H, 100).

4.35

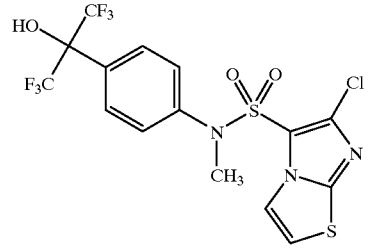

4.35

¹H NMR (CDCl₃): δ 7.65 (d, J=8.2 Hz, 2H), 7.28 (d, J=8.2 Hz, 2H), 6.95 (d, J=5.0 Hz, 1H), 6.70 (d, J=5.0 Hz, 1H), 3.82 (s, 1H), 3.35 (s, 3H). MS (ES−): 492 (M−H, 100).

4.36

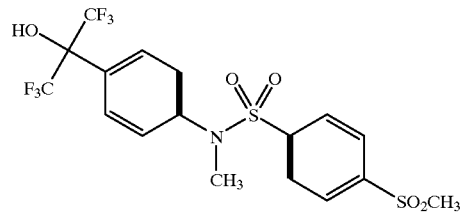

4.36

¹H NMR (CDCl₃): δ 8.05 (d, J=7.5 Hz, 2H), 7.76 (d, J=7.5 Hz, 2H), 7.70 (d, J=8.2 Hz, 2H), 7.21 (d, J=8.2 Hz, 2H), 3.57 (s, 1H), 3.21 (s, 3H), 3.06 (s, 3H). MS (ES−): 490 (M−H, 100).

4.37

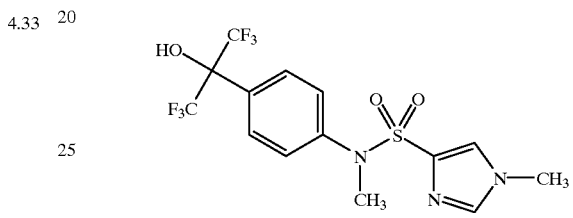

4.37

¹H NMR (CDCl₃): δ 7.68 (d, J=8.5 Hz, 2H), 7.50 (s, 1H), 7.40 (d, J=8.5 Hz, 2H), 7.20 (s, 1H), 3.70 (s, 3H), 3.30 (s, 3H). MS (ES+): 418 (M+H, 100).

4.38

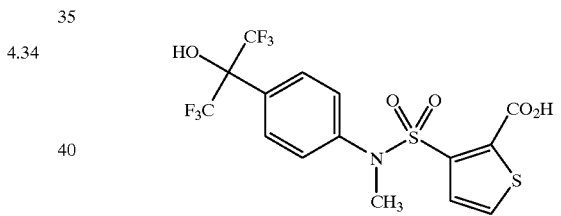

4.38

¹H NMR (CD₃OD): δ 7.70 (d, J=8.5 Hz, 2H), 7.43 (d, J=8.5 Hz, 2H), 7.33 (d, J=5.0 Hz, 1H), 6.92 (d, J=5.0 Hz, 1H), 3.46 (s, 2H). MS (ES−): 925 (2M−H, 100). Anal. Calcd. for C₁₉H₁₁F₆NO₅S₂: C, 38.88; 2.39; N, 3.02; S, 13.84. Found: C, 39.65; H, 2.97; N, 2.70; S, 12.09.

4.39

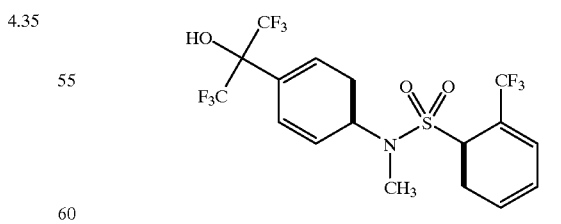

4.39

¹H NMR (CDCl₃): δ 7.90 (d, J=7.5 Hz, 1H), 7.78 (d, J=7.5 Hz, 1H), 7.70 (t, J=7.5 Hz, 1H), 7.68 (d, J=8.4 Hz, 2H), 7.57 (t, J=7.5 Hz, 1H), 7.27 (d, J=8.4 Hz, 2H), 3.83 (s, 1H), 3.36 (s, 3H). MS (ES−): 480 (M−H, 100). Anal. Calcd. for C₁₇H₁₂F₉NO₃S: C, 42.42; H, 2.51; N, 2.91; S, 6.66. Found: C, 43.71; H, 2.75; N, 2.67; S, 6.92.

4.40

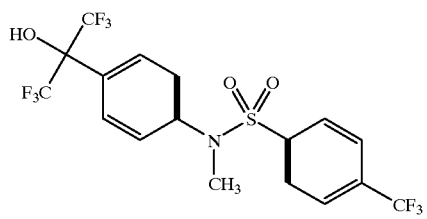

¹H NMR (CDCl₃): δ 7.72 (d, J=7.2 Hz, 2H), 7.69 (d, J=8.2 Hz, 2H), 7.66 (d, J=7.2 Hz, 2H), 7.21 (d, J=8.2 Hz, 2H), 3.52 (s, 1H), 3.20 (s, 3H). MS-): 480 (M-H, 100).

4.41

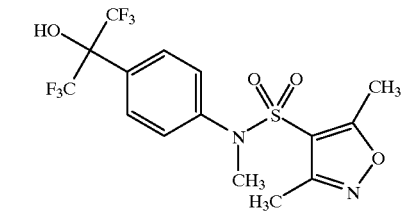

¹H NMR (CDCl₃): δ 7.72 (d, J=7.2 Hz, 2H), 7.35 (d, J=8.4 Hz, 2H), 3.58 (s, 1H), 3.25 (s, 3H), 2.25 (s, 3H), 1.96 (s, 3H). MS (ES-): 431 (M-H, 100)

4.42

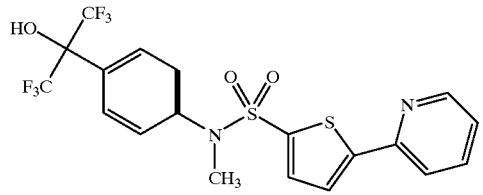

¹H NMR (CDCl₃): δ 8.56 (s, 1H), 7.78 (t, J=7.2 Hz, 1H), 7.65 (d, J=8.4 Hz, 2H), 7.50 (d, J=4.5 Hz, 1H), 7.30 (d, J=8.4 Hz, 2H), 7.28 (m, 2H), 7.21 (d, J=4.5 Hz, 1H), 3.30 (s, 3H). MS (ES-): 495 (M-H, 100).

4.43

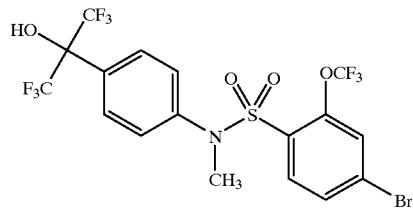

¹H NMR (CDCl₃): δ 7.72 (d, J=7.5 Hz, 1H), 7.65 (d, J=8.4 Hz, 2H), 7.50 (s, 1H), 7.48 (d, J=7.5 Hz, 1H), 7.29 (d, J=8.4 Hz, 2H), 3.85 (s, 1H), 3.35 (s, 3H). MS (ES-): 576 (M-H, 100).

4.44

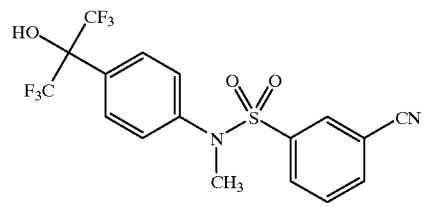

¹H NMR (CDCl₃): δ 7.86 (d, J=7.8 Hz, 1H), 7.85 (s, 1H), 7.70 (d, J=8.5 Hz, 2H), 7.60 (d, J=7.8 Hz, 2H), 7.20 (d, J=8.5 Hz, 2H), 3.48 (s, 1H), 3.25 (s, 3H). MS (ES-): 437 (M-H, 100). Anal. Calcd. for $C_{17}H_{12}F_6N_2O_3S$: C, 46.58; H, 2.76; N, 6.39; S, 7.32. Found: C, 46.97; H, 2.92; N, 6.18; S, 7.17.

4.45

¹H NMR (CDCl₃): δ 7.88 (d, J=8.0 Hz, 1H), 7.65 (d, J=8.0 Hz, 1H), 7.64 (d, J=8.4 Hz, 2H), 7.35 (d, J=8.4 Hz, 2H), 7.26 (t, J=8.0 Hz, 1H), 3.45 (s, 3H), 3.44 (s, 1H). MS (ES-): 481 M-H, 100). Anal. Calcd. for $C_{16}H_{11}Cl_2F_6NO_3S$: C, 39.85; H, 2.30; Cl, 14.70; N, 2.90; S, 6.65. Found: C, 40.49; H, 2.37; N, 2.89; S, 6.60; Cl, 14.95.

4.46

¹H NMR (CDCl₃): δ 7.71 (d, J=8.4 Hz, 2H), 7.35 (d, J=8.5 Hz, 2H), 6.86 (s, 1H), 3.41 (s, 1H), 3.35 (s, 3H). MS (ES-): 486 M-H, 100). Anal. Calcd. for $C_{14}H_9Cl_2F_6NO_3S_2$: C, 34.44; H, 1.86; Cl, 14.52; N, 2.87; S, 13.13. Found C, 35.20; H, 1.87; N, 2.95; S, 13.31; Cl, 15.04.

4.47

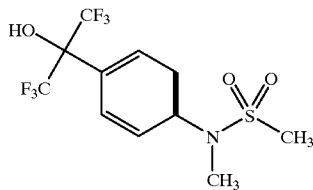

¹H NMR (CDCl₃): δ 7.75 (d, J=8.4 Hz, 2H), 7.48 (d, J=8.4 Hz, 2H), 3.49 (s, 1H), 3.37 (s, 3H), 2.88 (s, 3H). MS (ES−): 350 M−H, 100). Anal. Calcd. for C₁₁H₁₁F₆NO₃S: C, 37.61; H, 3.16; N, 3.99; S, 9.13. Found: C, 37.83; H, 3.27; N, 4.03; S,9.28.

4.48

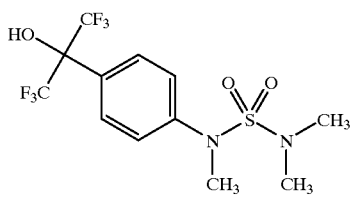

¹H NMR (CDCl₃): δ 7.70 (d, J=8.0 Hz, 2H), 7.49 (d, J=8.0 Hz, 2H), 3.45 (s, 1H), 3.30 (s, 3H), 2.80 (s, 6H). MS (ES−): 379 (M−H, 100). Anal. Calcd. for C₁₂H₁₄F₆N₂O₃S: C, 37.90; H, 3.71; N, 7.37. Found: C, 38.05; H, 3.77; N, 7.45.

4.49

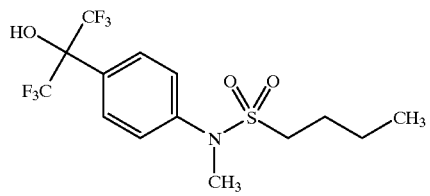

¹H NMR (CDCl₃): δ 7.72 (d, J=8.2 Hz, 2H), 7.48 (d, J=8.2 Hz, 2H), 3.65 (s, 1H), 3.30 (s, 3H), 3.01 (t, J=6.3 Hz, 2H), 1.80 (m, 2H), 1.31 (m,2H), 0.92 (t, J=6.0 Hz, 3H). MS (ES−): 392 (M−H, 100).

4.50

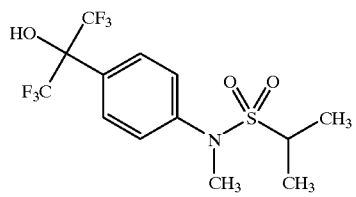

¹H NMR (CDCl₃): δ 7.71 (d, J=8.2 Hz, 2H), 7.50 (d, J=8.2 Hz, 2H), 3.90 (s, 1H), 3.41 (s, 3H), 3.32 (m, 1H), 1.38 (d, J=6.0 Hz, 6H). MS (ES−): 378 (M−H, 100).

4.51

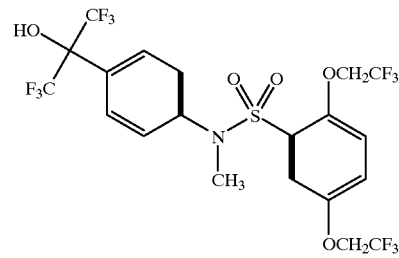

¹H NMR (CDCl₃): δ 7.60 (d, J=8.0 Hz, 2H), 7.28 (d, J=8.0 Hz, 2H), 7.25 (d, J=2.5 Hz, 1H), 7.15 (dd, J=7.25 Hz, 1H), 7.06 (d, J=7.2 Hz, 1H), 4.30 (q, J=7.0 Hz, 2H), 4.20 (q, J=7.0 Hz, 2H), 3.50 (s, 1H), 3.38 (s, 3H). MS (ES−): 6.10 (M+H, 100).

4.52

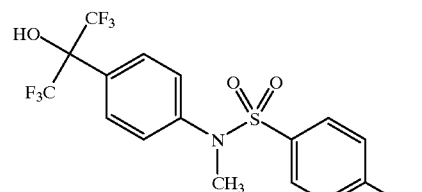

¹H NMR (CDCl₃): δ 7.78 (d, J=7.0 Hz, 2H), 7.70 (d, J=8.2 Hz, 2H), 7.62 (d, J=7.0 Hz, 2H), 7.20 (d, J=8.2 Hz, 2H), 3.51 (s, 1H), 3.21 (s, 3H). MS (ES−): 437 M−H, 100).

4.53

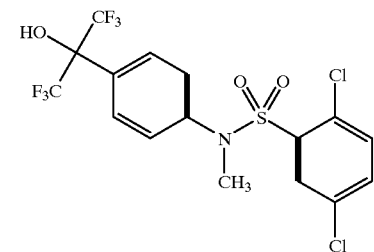

¹H NMR (CDCl₃): δ 7.82 (m, 2H), 7.68 (d, J=8.4 Hz, 2H), 7.65 (m, 2H), 7.28 (d, J=8.4 Hz, 2H), 3.72 (s, 1H), 3.40 (s, 3H). MS (ES−): 437 (M−H, 100).

4.54

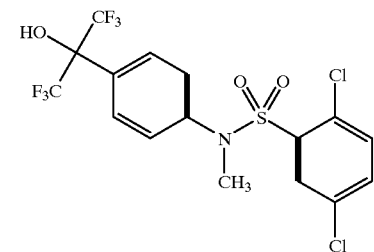

¹H NMR (CDCl₃): δ 7.90 (s, 1H), 7.66 (d, J=8.4 Hz, 2H), 7.42 (m, 2H), 7.33 (d, J=8.4 Hz, 2H), 3.47 (s, 1H), 3.40 (s,

3H). MS (ES–): 481 (M–H, 100). Anal. Calcd. for $C_{16}H_{11}Cl_2F_6NO_3S$: C, 39.85; H, 2.30; N, 2.90; S, 6.65. Found: C, 40.01; H, 2.19; N, 2.99; S, 6.82.

4.55

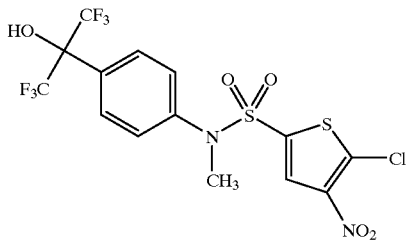

4.55

$^1$H NMR (CDCl$_3$): δ 7.80 (s, 1H), 7.77 (d, J=8.4 Hz, 2H), 7.31 (d, J=8.4 Hz, 2H), 3.50 (s, 1H), 3.31 (s, 3H). MS (ES–): 496 (M–H, 100).

4.56

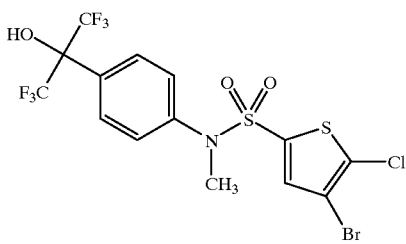

4.56

$^1$H NMR (CDCl$_3$): δ 7.72 (d, J=8.4 Hz, 2H), 7.30 (d, J=8.4 Hz, 2H), 7.12 (s, 1H), 3.48 (s, 1H), 3.28 (s, 3H). MS (ES–): 531 (M+H, 100). Anal. Calcd. for $C_{14}H_9BrClF_6NO_3S_2$: C, 31.57; H, 1.70; N, 2.63; S, 12.21. Found: C, 40.01; H, 2.19; N, 2.99; S, 6.82.

4.57

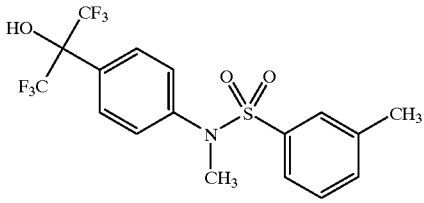

4.57

$^1$H NMR (CDCl$_3$): δ 7.66 (d, J=8.4 Hz, 2H), 7.35 (,3H), 7.20 (m, 3H), 3.50 (s, 1H), 3.19 (s, 3H), 2.30 (s, 3H). MS (ES–): 426 (M–H, 100).

4.58

4.58

$^1$H NMR (CD$_3$OD): δ 8.59 (s, 1H), 7.97 (2H, J=7.8 Hz, 2H), 7.70 (t, J=7.8 Hz, 1H), 7.68 (d, J=8.2 Hz, 2H), 7.62 (t, J=7.8 Hz, 2H), 7.50 (s, 1H), 7.20 (d, J=8.2 Hz, 2H), 3.30 (s, 1H), 3.21 (s, 3H). MS (ES–): 558 (M–H, 100). Anal. Calcd. for $C_{20}H_{15}F_6NO_5S_3$: C, 42.93; H, 2.73; N, 2.50; S, 17.19. Found: C, 43.07, H, 2.70; N, 2.50; S, 17.30.

4.59

4.59

This compound was prepared from 4.46 using conditions similar to the palladium-catalyzed reduction of Example 5, below (monitoring the reaction to obtain an incomplete reduction of the chloro substituents).

$^1$H NMR (CDCl$_3$): δ 7.70 (d, J=8.8 Hz, 2H), 7.50 (s, 1H), 7.28 (d, J=8.8 Hz, 2H), 6.83 (s, 1H), 3.37 (s, 1H), 3.25 (s, 1H). MS (ES–): 907 (2M–H, 100). Anal. Calcd. for $C_{14}H_{10}ClF_6NO_3S_2$: C, 37.05; H, 2.22; N, 3.09. Found: C, 37.92; H, 2.35; N, 3.11.

4.60

4.60

This compound was prepared from 4.46 using conditions similar to the palladium-catalyzed reduction of Example 5, below.

$^1$H NMR (CDCl$_3$): δ 7.76 (d, J=3.0 Hz, 1H), 7.67 (d, J=8.8 Hz, 2H), 7.37 (dd, J=4.0, 1.5 Hz, 1H), 7.27 (d, J=8.8 Hz, 2H), 6.99 (d, J=4.0 Hz, 1H), 3.49 (s, 1H), 3.22 (s, 3H). MS (ES–): 461 (M–H, 100). MS (ES–): 837 (2M–H, 100). Anal. Calcd. for $C_{14}H_{11}F_6NO_3S_2$: C, 40.10; H, 2.64; N, 3.34. Found: C, 40.22; H, 2.67; N, 3.36.

4.61

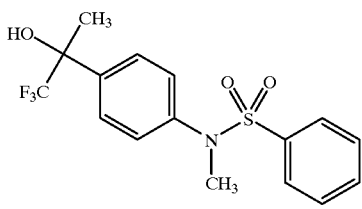

4.61

The starting aniline was prepared via treatment of 4-(trifluoroacetyl)aniline with methyl magnesium bromide. Subsequent alkylation and sulfonylation was carried out as described in the examples above.

$^1$H-NMR(CD$_3$OD): δ 7.64 (m, 1H), 7.54 (m, 6H), 7.12 (dd, J=6.64, 2.12, 2H), 3.18 (s, 3H). MS (ES+): 382 (M+Na$^+$, 50). Oil

Example 5

This example illustrates preparation of compound 5 by reduction of 4.28.

5

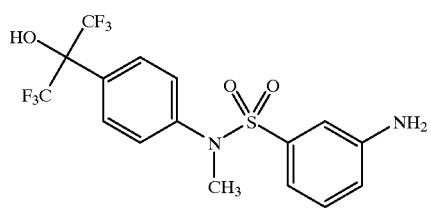

To a mixture of N-Methyl-N-[4-[2,2,2-trifluoro-1-hydroxy-1-(trifluoromethyl)ethyl]phenyl]-3-nitrobenzenesulfonamide (4.28) (70 mg), dissolved in 10 mL of MeOH was added 10% Pd/carbon (10 mg) and the reaction was stirred under a H$_2$ atmosphere for 2 days. The resulting mixture was filtered through Celite and the solvent was evaporated under reduced pressure. The crude product was purified by preparative-TLC to obtain 30 mg of the title compound as an oil.

$^1$H-NMR(CD$_3$OD): δ 7.66 (d, J=8.76 Hz, 2H), 7.23 (m, 3H), 6.91 (d, J=7.9 Hz, 1H), 6.86 (d, J=1.62, 7.96 Hz, 1H), 6.74 (s, 1H), 3.19 (s, 3H). Anal. Calcd. For C$_{19}$H$_{18}$F$_6$N$_2$O$_4$S: C, 47.11; H, 3.75; N, 5.78. Found: C, 47.19; H, 3.75; N, 5.77.

Example 6

This example illustrates preparation of compound 6 via esterification of 4.23.

6

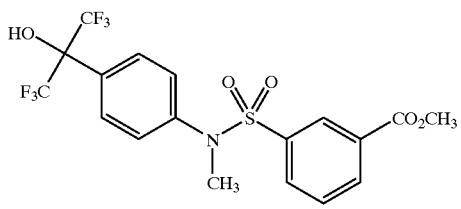

To N-Methyl-N-[4-[2,2,2-trifluoro-1-hydroxy-1-(trifluoromethyl)ethyl]phenyl]-3-carboxybenzenesulfonamide (4.23, 0.536 mmol, 245 mg) under N$_2$ at 0° C. in 10 mL of THF was added triethylamine (2.15 mmol, 300 μL), MeOH (0.864 mmol, 35 μL), and bis(2-oxo-3-oxazolidinyl)phosphinic chloride (0.833 mmol, 212 mg). The mixture was stirred for 20 h at 0° C. The reaction was quenched with water, the THF was removed under vacuum, and the reaction product was extracted with EtOAc. The organic extract was dried with MgSO$_4$, the solvent was evaporated and the crude product was purified by preparative TLC to afford 106 mg of the title compound as a solid.

mp 88–90° C.

$^1$H-NMR(CD$_3$OD): δ 8.26 (d, J=7.68 Hz, 1H), 8.03 (d, J=1.7 Hz, 1), 7.73 (m, 3H), 7.68 (m, 3H), 7.25 (m, 2H) 3.89 (s, 3H), 3.22 (s, 3H). MS (ES+): 472 (M+H$^+$, 100). Anal. Calcd. for C$_{18}$H15F$_6$NO$_5$S: C, 45.86; H, 3.21; N, 2.97. Found: C, 46.02; H, 3.32; N, 2.91.

Example 7

This example provides the synthesis of compound 7.

7

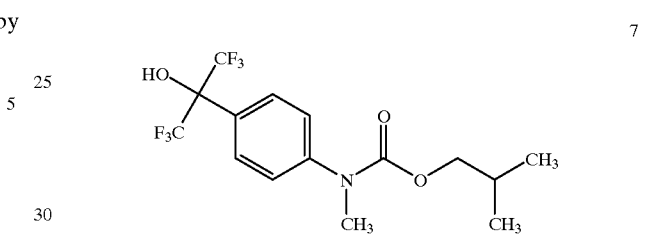

To a stirred solution of N-methyl-4-[2,2,2-trifluoro-1-hydroxy-1-(trifluoromethyl)ethyl]aniline (80 mg, 0.293 mmol) and diisopropylethylamine (112 mL, 0.630 mmol) in dichloromethane (2 mL) was added isobutyl chloroformate (42 mL, 0.323 mmol) at 0° C. The resulting mixture was stirred for 6 h as the cooling bath temperature increased to room temperature. The reaction mixture was diluted with ethyl acetate, and the organic phase was washed sequentially with 1N HCl and brine. The separated organic layer was dried over MgSO$_4$, filtered, and concentrated. The residue was purified by flash chromatography on silica gel (hexanes and ethyl acetate (4:1) as eluant) to give the title compound (80 mg, 73.2%) as a clear oil.

$^1$H NMR (CDCl$_3$): δ 7.70 (d, J=8.5 Hz, 2H), 7.39 (d, J=8.5 Hz, 2H), 3.93 (d, J=7.2 Hz, 2H), 3.69 (s, 1 H), 3.37 (s, 3H), 1.92 (m, 1H), 0.90 (d, J=6.3 Hz, 6H). Anal. Calcd. for C$_{15}$H$_{17}$F$_6$NO$_3$: C, 48.26; H, 4.59; N, 3.75. Found: C, 48.34; H, 4.61; N, 3.72.

The following carbamates were prepared according to the procedure described.

7.1

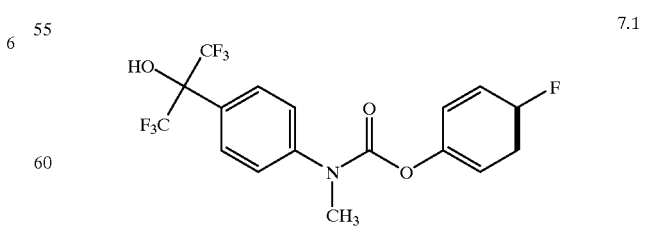

$^1$H NMR (CDCl$_3$): δ 7.71 (d, J=8.6 Hz, 2H), 7.43 (d, J=8.6 Hz, 2H), 7.05 (m, 4H), 4.46 (s, 1H), 3.42 (s, 3H). MS (ES-): 412 (M+H, 100).

7.2

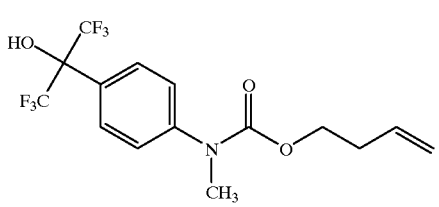

¹H NMR (CDCl₃): δ 7.69 (d, J=8.4 Hz, 2H), 7.37 (d, J=8.4 Hz, 2H), 5.75 (m, 1H), 5.05 (d, J=16.5 Hz, 1H), 5.04 (d, J=10.0 Hz, 1H), 4.20 (t, J=6.5 Hz, 2H), 3.40 (s, 1H), 3.35 (s, 3H), 2.40 (m, 2H). MS (ES-): 370 (M-H, 100).

7.3

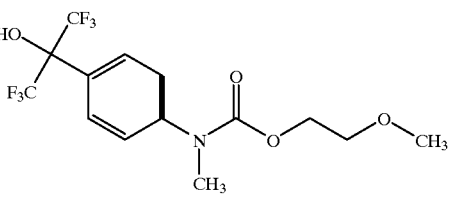

¹H NMR (CDCl₃): δ 7.69 (d, J=8.4 Hz, 2H), 7.35 (d, J=8.4 Hz, 2H), 5.15 (s, 1H), 4.30 (m, 2H), 3.60 (m, 2H). MS (ES-): 374 (M-H, 100).

7.4

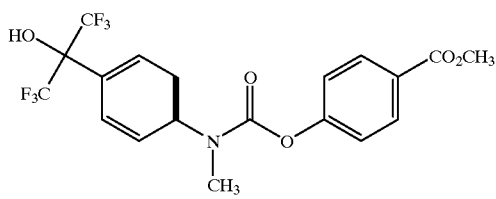

¹H NMR (CDCl₃): δ 8.05 (d, J=7.8 Hz, 2H), 7.75 (d, J=8.5 Hz, 2H), 7.43 (d, J=8.5 Hz, 2H), 7.20 (d, J=7.8 Hz, 2H), 4.81 (s, 1H), 3.90 (s, 3H), 3.45 (s, 3H). MS (ES-): 452 (M+H, 100).

7.5

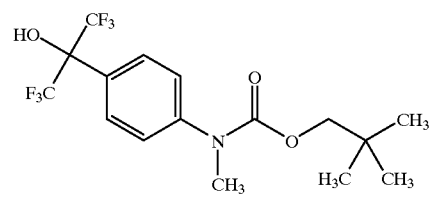

¹H NMR (CDCl₃): δ 7.70 (d, J=8.6 Hz, 2H), 7.37 (d, J=8.6 Hz, 2H), 3.81 (s, 2H), 1.10 (s, 9H). MS (ES-): 386 (M-H, 100). Anal. Calcd. for C₁₇H₁₃F₆NO₃: C, 49.62; H, 4.94; N, 3.62. Found: C, 49.78; H, 5.02; N, 3.64.

7.6

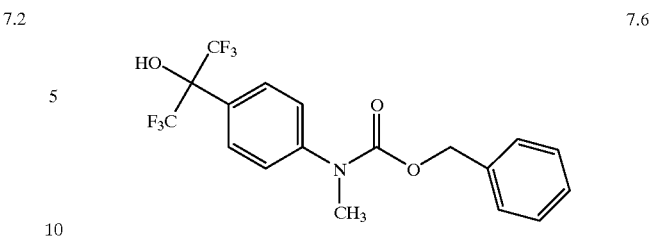

¹H NMR (CDCl₃): δ 7.70 (d, J=8.6 Hz, 2H), 7.35 (d, J=8.6 Hz, 2H), 7.30 (m, 5H), 5.18 (s, 2H), 5.05 (s, 1H), 3.32 (s, 3H). MS (ES-): 408 (M-H, 100).

Example 8

This example provides the synthesis of urea (8).

8

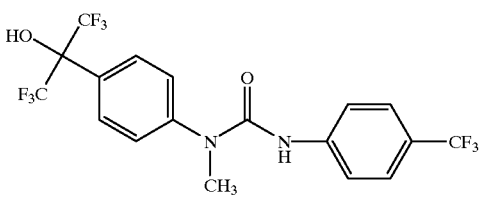

A mixture of N-methyl-4-[2,2,2-trifluoro-1-hydroxy-1-(trifluoromethyl)ethyl]aniline (50 mg, 0.83 mmol), N,N-dimethylaminopyridine (DMAP, 22 mg, 0.183 mmol) and 4-trifluoromethylphenylisocyanate (26 mL, 0.183 mmol) in toluene (1 mL) was stirred at room temperature until reaction was completed by tlc. The resulting mixture was diluted with ethyl acetate, washed with 1N HCl and brine. The organic layer was dried over MgSO₄, and filtered. Solvents were evaporated and the residue was purified by flash chromatography on silica gel (hexanes:ethyl acetate (4:1) as eluant) to provide the title compound (8, 70.0 mg, 85%).

¹H NMR (DMSO): δ 9.00 (s, 1H), 7.69 (d, J=8.2 Hz, 4H), 7.48 (d, J=8.2 Hz, 2H), 7.48 (d, J=8.2 Hz, 2H), 3.35 (s, 3H). MS (ES+): 459 (M-H, 100).

The following ureas were prepared as described above, using the appropriate isocyanates:

8.1

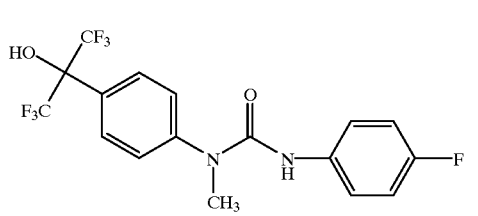

¹H NMR (CD₃OD): δ 7.80 (d, J=8.2 Hz, 2H), 7.45 (d, J=8.2 Hz, 2H), 7.30 (d, J=8.0 Hz, 2H), 6.98 (t, 8.0 Hz, 2H), 3.35 (s, 3H).

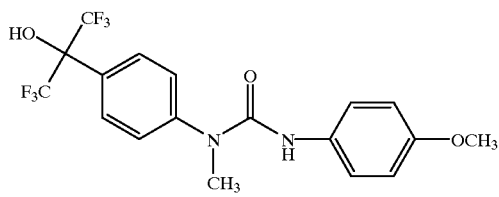

8.2

¹H NMR (CD₃OD): δ 7.80 (d, J=8.2 Hz, 2H), 7.45 (d, J=8.5 Hz, 2H), 7.20 (d, J=8.0 Hz, 2H), 6.82 (d, J=8.0 Hz, 2H), 4.85 (s, 1H), 3.72 (s, 3H), 3.35 (s, 3H), 3.38 (s, 3H). MS (ES−): 421 (M+H, 100).

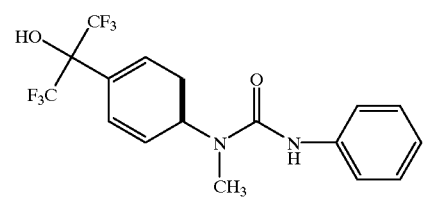

8.3

¹H NMR (CDCl₃): δ 7.81 (d, J=8.4 Hz, 2H), 7.42 (d, J=8.4 Hz, 2H), 7.20–7.32 (m, 4H), 7.00 (t, J=7.0 Hz, 1H), 6.25 (bs, 1H), 3.91 (bs, 1H), 3.38 (s, 3H), MS (ES−): 193 (M−H, 100). Anal. Calcd. for $C_{17}H_{14}F_6N_2O_2$: C, 52.05; H, 3.60; N, 7.14. Found: C, 52.09; H, 3.70; N, 7.29.

Example 9

This example illustrates an alternative procedure for the preparation of ureas of the present invention, exemplified by N-methyl-N-(4-morpholinecarbonyl)-4-[2,2,2-trifluoro-1-hydroxy-1-(trifluoromethyl)ethyl]aniline (9).

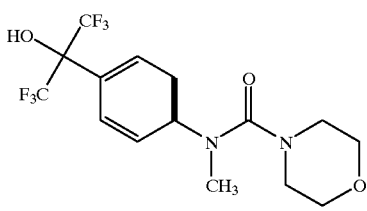

9

To a stirred solution of N-methyl-4-[2,2,2-trifluoro-1-hydroxy-1-(trifluoromethyl)ethyl]aniline (50 mg, 0.183 mmol) and diisopropylethylamine (73.3 mL, 0.421 mmol) in dichloromethane (2 mL) was added 4-morpholinecarbonyl chloride (21 mL, 0.183 mmol). Stirring was continued for 100 hours at room temperature. At the completion of the reaction, the reaction mixture was diluted with ethyl acetate, and washed sequentially with 1N HCl and brine. The organic layer was dried over MgSO₄ and filtered. Solvents were removed from the filtrate under reduced pressure and the residue was purified by flash chromatography on silica gel (hexanes and ethyl acetate (4:1) as eluant) to provide the title compound (50 mg, 70.0%) as a clear oil.

¹H (CDCl₃): δ 7.69 (d, J=8.4 Hz, 2H), 7.12 (d, J=8.4 Hz, 2H), 3.95 (bs, 1H), 3.50 (m, 4H), 3.25 (s, 3H), 3.20 (m, 4H). MS (ES−): 387 (M+H, 100).

Example 10

This example provides procedures for the preparation of N-alkyl derivatives of the sulfonamide compounds of the invention provided in Example 2, and related analogs.

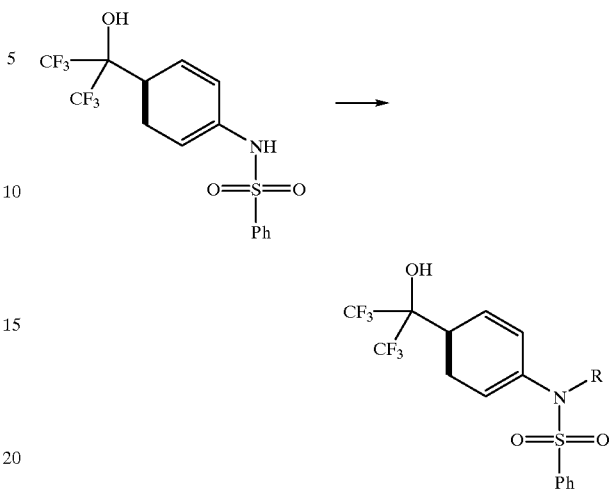

Synthesis of compund 10.1

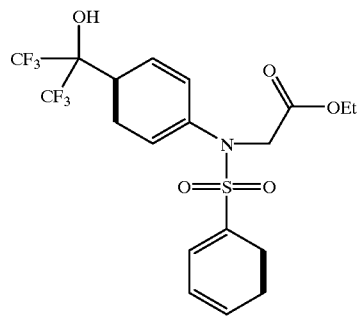

10.1

To a stirred mixture of sulfonamide 2 (2.08 g, 5.21 mmol, from Example 2) and ethyl bromoacetate (0.950 g, 5.68 mmol) in DMF (15 mL) and THF (5 mL), was added sodium hydride (60% dispersion in mineral oil, 0.230 g, 5.70 mmol) at 0° C. The mixture was stirred overnight as the temperature was allowed to warm to room temperature. At the completion of the reaction (as determined by thin-layer chromatography), the mixture was diluted with ethyl acetate, washed with brine (3×), dried over MgSO₄, and concentrated. The residue was purified by flash chromatography on silica gel (hexane/EtOAc gradient from 8:1 to 2:1, as eluant) to give the title compound (2.01 g, 84%) as a clear oil.

¹H NMR (CDCl₃): δ 7.69 (d, J=7.6 Hz, 2H), 7.66 (d, J=8.4 Hz, 2H), 7.60 (t, J=7.6 Hz, 1H), 7.48 (t, J=7.6 Hz, 2H), 7.32 (d, J=8.4 Hz, 2H), 4.44 (s, 2H), 4.15 (q, J=6.5 Hz, 2H), 3.75 (s, 1H), 1.21 (t, J=6.5 Hz, 3H). MS (ES−): 484 M−H, 100). Anal. Calcd. for $C_{19}H_{17}F_6NO_5S$: C, 47.01; H, 3.53; N, 2.89; S, 6.61. Found: C, 47.10; H, 3.59; N, 2.81; S, 6.64.

Synthesis of compound 10.2

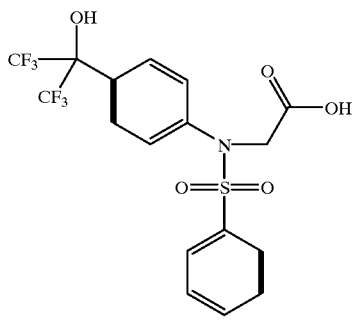

10.2

To a solution of compound 10.1 (100 mg, 0.176 mmol) in 1 mL methanol, 1 mL THF, and 1 mL water was added 1 N NaOH (0.440 mL). The resulting mixture was stirred at room temperature for 3 hours, then diluted into ethyl acetate, washed with brine (3×), dried over MgSO$_4$, and concentrated under reduced pressure. The residue was purified by flash chromatography on SiO$_2$ (CH$_2$Cl$_2$:MeOH:AcOH (10:1:0.05) as eluant) to give the title compound (60 mg, 65% yield) as a clear oil.

$^1$H NMR (CD$_3$OD): δ 7.80 (m, 5H), 7.66 (t, J=7.2 Hz, 2H), 7.46 (d, J=8.2 Hz, 2H), 4.60 (s, 2H). MS (ES−): 456 (M−H, 100). Anal. Calcd. for C$_{17}$H$_{13}$F$_6$NO$_5$S: C, 44.65; H, 2.87; N, 3.06; S, 7.01. Found: C, 44.84; H, 2.96; N, 3.21.

Synthesis of compound 10.3

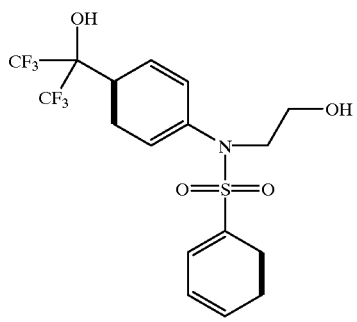

10.3

A portion of the compound from Example 10.1 (71 mg, 0.146 mmol) was treated with LiAlH$_4$ (1 M in THF, 200 mL, 0.200 mmol) in THF at 0° C. The reaction was quenched by careful addition of water. Ethyl acetate was added and the resulting suspension was filtered through a Celite pad. The filtrate was washed with brine, dried over MgSO$_4$, and concentrated under reduced pressure. Crude product was purified by chromatography on SiO$_2$ (hexanes/EtOAc (2:1) as eluant) to provide the title compound (48 mg, 74% yield).

$^1$H NMR (CDCl$_3$): δ 7.68 (d, J=8.6 Hz, 2H), 7.62 (d, J=8.0 Hz, 2H), 7.60 (t, J=7.2 Hz, 1H), 7.50 (dd, J=8.0, 7.2 Hz, 2H), 7.20 (d, J=8.6 Hz, 2H), 3.73 (m, 4H), 3.60 (s, 1H). MS (ES−): 442 (M−H, 100). Anal. Calcd. for C$_{17}$H$_{15}$F$_6$NO$_4$S: C, 46.05; H, 3.41; N, 3.16; S, 7.23. Found: C, 46.15; H, 3.44; N, 3.21.

Synthesis of compound 10.4

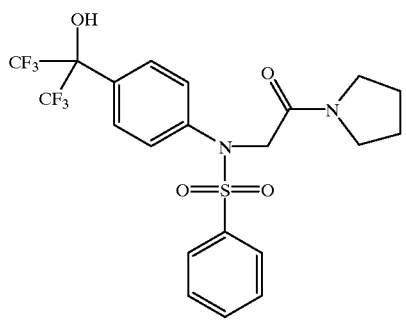

10.4

A solution of the acid (10.2) from above (137 mg, 0.300 mmol) in 4 mL of CH$_2$Cl$_2$ with two drops of DMF added was treated with a solution of oxalyl chloride (2M in CH$_2$Cl$_2$, 4 mL) at room temperature for 2 hours. Solvent was evaporated under reduced pressure to provide an intermediate acyl chloride. To a solution of acyl chloride in CH$_2$Cl$_2$ was added pyrrolidine (80 (L, 0.958 mmol). After stirring for 30 min, additional CH$_2$Cl$_2$ was added. The organic layer was washed with 1 N HCl (2×) and brine (3×), dried over MgSO$_4$, and concentrated. The crude product was purified by flushing chromatography on SiO$_2$ (4:1 hexanes:EtOAc as eluant) to provide 150 mg of the title compound (100%).

$^1$H NMR (CDCl$_3$): δ 7.68 (d, J=8.6 Hz, 2H), 7.60 (d, J=7.6 Hz, 2H), 7.55 (t, J=7.6 Hz, 1H), 7.42 (t, J=7.6 Hz, 2H), 7.35 (t, J=7.6 Hz, 2H), 4.45 (s, 2H), 4.40 (s, 1H), 3.52 (t, J=5.5 Hz, 2H), 3.38 (t, J=5.5 Hz, 2H), 1.95 (m, 2H), 1.82 (m, 2H). MS (ES−): 509 (M−H, 100). Anal. Calcd. for C$_{21}$H$_{20}$F$_6$N$_2$O$_4$S: C, 49.41; H, 3.95; N, 5.49; S, 6.28. Found: C, 49.59; H, 4.00; N, 5.42; S, 6.25.

The following compounds were prepared in accordance with the above procedure, replacing pyrrolidine with the appropriate amine:

10.5 (using diethylamine)

$^1$H NMR (CDCl$_3$): δ 7.65 (d, J=8.5 Hz, 2H), 7.60 (d, J=7.5 Hz, 2H), 7.55 (t, J=7.5 Hz, 1H), 7.45 (d, J=7.5 Hz, 2H), 7.31 (d, J=8.5 Hz, 2H), 4.38 (s, 2H), 3.97 (s, 1H), 3.42 (q, J=6.6 Hz, 2H), 3.25 (q, J=6.6 Hz, 2H), 1.21 (t, J=6.6 Hz, 3H), 0.90 (t, J=6.6 Hz, 3H). MS (ES+): 513 N+H, 100). Anal. Calcd. for C$_{21}$H$_{22}$F$_6$N$_2$O$_4$S: C, 49.22; H, 4.33; N, 5.47; S, 6.26. Found: C, 49.48; H, 4.35; N, 5.37; S, 6.24.

10.6 (using 4-methylpiperazine)

$^1$H NMR (CDCl$_3$): δ 7.62 (d, J=8.5 Hz, 2H), 7.60 (t, J=7.5 Hz, 1H), 7.55 (t, J=7.5 Hz, 2H), 7.45 (t, J=7.5 Hz, 2H), 7.25 (d J=7.5 Hz, 2H), 4.45 (s, 2H), 3.70 (m, 2H), 3.45 (m, 2H), 2.50 (m, 2H), 2.35 (m, 2H), 2.30 (s, 3H). MS (ES−): 540 (M−H, 100), MS (ES−): 538 (M−H, 100). Anal. Calcd. for C$_{22}$H$_{23}$F$_6$N$_3$O$_4$S: C, 48.98; H, 4.30; F, 21.13; N, 7.79; O, 11.86; S, 5.94. Found: C, 49.26; H, 4.38; N, 7.64; S. 5.83.

10.7 (using 2-methylpiperidine)

$^1$H NMR (CDCl$_3$): δ 7.62 (d, J=8.5 Hz, 2H), 7.60 (t, J=7.5 Hz, 1H), 7.60 (d, J=7.5 Hz, 2H), 7.45 (t, J=7.5 Hz, 2H), 7.30 (d, J=8.5 Hz, 2H), 4.50 (s, 2H), 4.30 (m, 1H), 3.85 (m, 1H), 1.40–1.70 (m, 6H), 0.80 (d, J=5.5 Hz, 3H). MS (ES−): 537 (M−H, 100). Anal. Calcd. for C$_{23}$H$_{24}$F$_6$N$_2$O$_4$S: C, 51.30; H, 4.49; N, 5.20; S, 5.95. Found: C, 51.81; H, 4.68; N, 5.13; S, 5.89.

Example 11

This example illustrates a procedure for the reduction of the amides prepared in Example 10 to their corresponding amine derivatives.

47

Synthesis of compound 11.1 from compound 10.4:

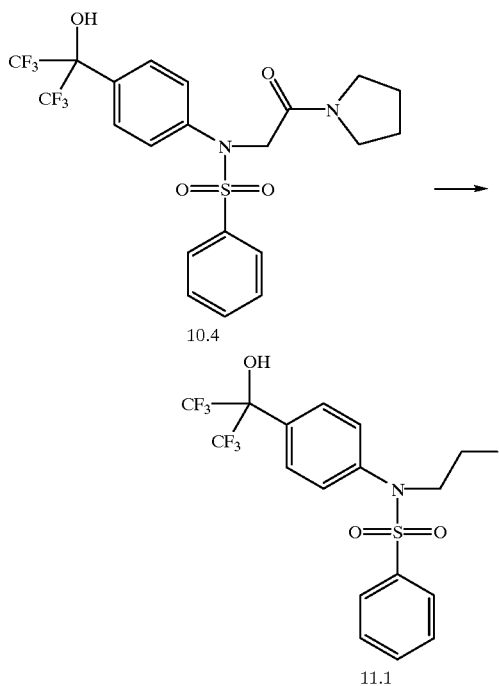

The amide produced in 10.4 (126 mg, 0.247 mmol) was treated with LiAlH$_4$ (18.7 mmg, 37.4 mmol) in THF (3 mL) at reflux for 2 hours. The reaction was quenched by careful addition of water, ethyl acetate was added, and the resulting suspension was filtered through a Celite pad. The filtrate was washed with brine, dried over MgSO$_4$, and stripped. Crude product was purified by flushing chromatography on SiO$_2$ eluted CH$_2$Cl$_2$:MeOH (20:1) to give 60 mg (50%) of amine 11.1.

$^1$H NMR (CDCl$_3$): δ 7.60 (t J=7.6 Hz, 1H), 7.57 (d, J=8.5 Hz, 2H), 7.52 (d, J=7.6 Hz, 2H), 7.45 (t, J=7.6 Hz, 2H), 7.11 (d J=8.5 Hz, 2H), 3.80 (t, J=6.5 Hz, 2H), 2.70 (m. 2H), 2.55 (m, 4H), 1.80 (m, 4H). MS (ES+): 497 (M+H, 100). Anal. Calcd. for: C, 50.80; H, 4.47; N, 5.64; S, 6.46; Found: C, 51.06; H, 4.58; N, 5.51; S, 6.42.

In a similar manner, the amides 10.5, 10.6 and 10.7 were reduced to their corresponding amides.

Compound 11.2 (prepared from compound 10.5)

$^1$H NMR (CDCl$_3$): δ 7.55 (m, 5H), 7.45 (t, J=7.5 Hz, 2H), 7.15 (t, J=8.5 Hz, 2H), 3.70 (m, 2H), 2.40–2.65 (m, 6H), 0.95 (, 3H). MS (ES+): 499 (M+H, 100). Anal. Calcd. for C$_{21}$H$_{24}$F$_6$N$_2$O$_3$S: C, 50.60; H, 4.85; N, 5.62; S, 6.43. Found: C, 50.65; H, 4.90; N, 5.59; S, 6.35.

Compound 11.3 (prepared from compound 10.6)

$^1$H NMR (CDCl$_3$): δ 7.65 (d, J=8.5 Hz, 2H), 7.60 (m, 3H), 7.45 (t, J=7.5 Hz, 2H), 7.12 (d, J=8.5 Hz, 2H), 3.70 (t, J=6.3 Hz, 2H), 2.30–2.50 (m, 8H), 2.20 (s, 3H). MS (ES–): 524 (M–H, 100). Anal. Calcd. for C$_{22}$H$_{25}$F$_6$N$_3$O$_3$S: C, 50.28; H, 4.80; N, 8.00; S, 6.10. Found: C, 49.28; H, 5.12; N, 7.59; S, 5.74.

Compound 11.4 (prepared from compound 10.7)

$^1$H NMR (CDCl$_3$): δ 7.65 (d, J=8.6 Hz, 2H), 7.57 (d, J=7.4 Hz, 2H), 7.56 (t, J=7.4 Hz, 1H), 7.46 (t, J=7.4 Hz, 2H), 7.17 (d, J=8.6 Hz, 2H), 3.65 (m, 2H), 2.76 (m, 1H), 2.45 (m, 1H), 2.25 (m, 1H), 2.15 (m, 1H), 1.20–1.70 (m, 6H). 0.92 (d, J=5.0 Hz, 3H). MS (ES+): 525 (M+H, 100). Anal. Calcd for

48

C$_{23}$H$_{26}$F$_6$N$_2$O$_3$S: C, 52.67; H, 5.00; N, 5.34; S, 6.11. Found: C, 52.96; H, 5.10; N, 5.18; S, 5.89.

Example 12

This example illustrates the synthesis of compound 12.

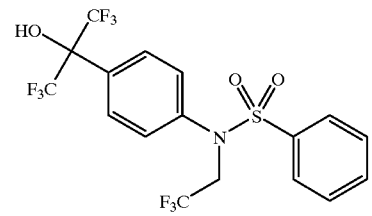

12.1 Preparation of N-trifluoroethylaniline derivative

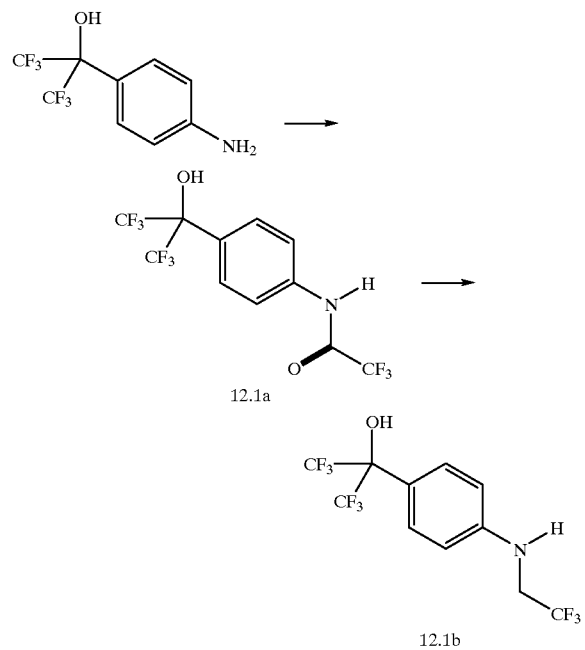

To a suspension of 4-[2,2,2-trifluoro-1-hydroxy-1-(trifluoromethyl)ethyl]aniline (9.07 g, 35.0 mmol) in CH$_2$Cl$_2$ (100 mL) was added a solution of trifluoroacetic anhydride (5.7 mL, 40.2 mmol) in CH$_2$Cl$_2$ (50 mL) dropwise at room temperature. The solution was stirred for 3 hours (solution cleared and TLC indicated that the reaction was completed. The reaction mixture was washed with water, aqueous NaHCO$_3$, and brine. The organic layer was drawn off, dried over MgSO$_4$, filtered, and concentrated to give 12.1 g of the intermediate trifluoroacetanilide (12.1a). The intermediate 12.1a was taken up in THF (50 mL) and treated with LiAlH$_4$ (4.00 g, 106 mmol) at reflux for 10 hours. The reaction was quenched by sequentially adding 4 mL water, 4 mL of 15% NaOH, and 12 mL of water. The resulting suspension was stirred for an additional 30 minutes, filtered through a Celite pad, which was then rinsed with THF. The combined filtrate and rinse was concentrated under reduced pressure. The residue was taken up in EtOAc, washed with brine, dried over MgSO$_4$, filtered, and concentrated. The resulting crude product was purified by chromatography on SiO$_2$ (4:1 hexanes:EtOAc as eluant) to provide 11.0 g (92%) of the title compound (12.1b).

¹H NMR (CDCl₃): δ 7.52 (d, J=8.6 Hz, 2H), 6.72 (d, J=8.6 Hz, 2H), 4.10 (bs, 1H), 3.80 (q, J=8.5 Hz, 2H), 3.31 (bs, 1H). MS (ES+): 342 (M+H, 100).

12.2 Sulfonylation of 12.1b

A sample of 12.1b from above (1.87 g, 5.48 mmol) was treated with benzenesulfonyl chloride (1.18 g, 6.68 mmol) in pyridine (10 mL) at room temperature for 10 days. The reaction mixture was diluted with EtOAc, washed with aqueous NaHCO₃, and brine. The organic layer was dried over MgSO₄, filtered, and concentrated. The crude product was purified by chromatography on SiO₂ 4:1 hexanes:EtOAc as eluant) to provide 1.65 g (62%) of compound 12.

¹H NMR (CDCl₃): δ 7.78 (d, J=8.8 HZ, 2H), 7.61 (t, J=7.6 Hz, 1H), 7.58 (d, J=7.6 Hz, 2H), 7.46 (t, J=7.6 Hz, 2H), 4.24 (q, J=8.2 Hz, 2H), 3.41 (s, 1H), MS (ES−): 480 (M−H, 100). Anal. Calcd. for C₁₇H₁₂F₉NO₃S: C, 42.42; H, 2.51; N, 2.91; S, 6.66. Found: C, 42.70; H, 2.55; N, 2.84; S, 6.61.

In a similar manner, compound 12.3 was prepared by substituting 3-cyanobenzenesulfonyl chloride for benzenesulfonyl chloride.

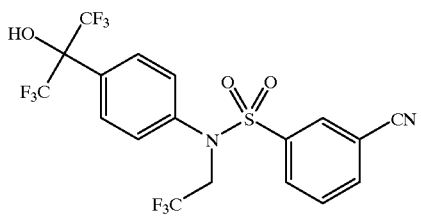

12.3

¹H NMR (CDCl₃): δ 7.91 (s, 1H), 7.90 (d, J=7.5 Hz, 2H), 7.80 (d, J=7.5 Hz, 1H), 7.75 (d, J=8.8 Hz, 2H), 7.80 (d J=7.5 Hz, 1H), 7.75 (d, J=8.8 Hz, 2H), 7.62 (t, J=7.5 Hz, 1H), 7.19 (d, J=8.8 Hz, 2H), 4.30 (q, J=8.2 Hz, 2H), 3.62 (s, 1H). MS (ES−): 505 (M−H, 100). Anal. Calcd. for C₁₈H₁₁F₉N₂O₃S: C, 42.70; H, 2.19; N, 5.53; S, 6.33. Found: C, 43.41; H, 2.46; N, 5.67.

Example 13

This example illustrates the preparation of 13, and related derivatives 13.3 and 13.4.

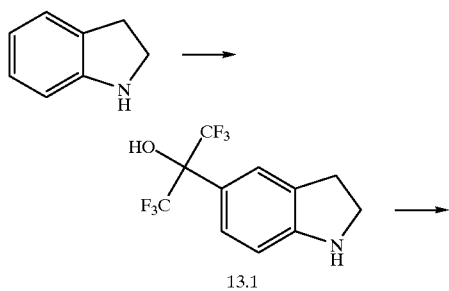

13.1

-continued

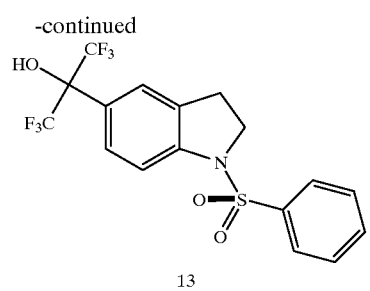

13

Synthesis of compound 13.1

To a stirred mixture of indoline (5.32 g, 44.6 mmol) and toluenesulfonic acid (75 mg, 0.395 mmol) was added hexafluoroacetone hydrate (7 mL, 49.1 mmol) at 90° C. over 15 min. The resulting mixture was heated at 135 ° C. overnight. After cooling to room temperature, the mixture was diluted with EtOAc, washed with aqueous NaHCO₃ (2×) and brine (2×). The organic layer was dried over MgSO₄, filtered, and concentrated. The crude product was purified by chromatography on SiO₂ (6:1 to 4:1 hexanes:EtOAc as eluant) to give the intermediate substituted indoline (13.1, 6.35 g, 50% yield).

¹H NMR (CDCl₃): δ 7.41 (s, 1H), 7.32 (d, J=8.5 Hz, 1H), 6.65 (d, J=8.5 Hz, 1H), 3.60 (d, J=5.5 Hz, 2H), 3.08 (d, J=5.5 Hz, 2H). MS (ES+): 286 (M+H, 100).

Synthesis of compound 13.

Sulfonylation of compound 13.1 was carried out as described in the Examples above to provide the title compound (13).

¹H NMR (CDCl₃): δ 7.84 (d, J=8.0 Hz, 2H), 7.68 (d, J=8.4 Hz, 2H), 7.59 (t, J=8.0 Hz, 1H), 7.52 (d, J=8.4 Hz, 1H), 7.48 (t, J=8.0 Hz, 2H), 7.41 (s, 1H), 3.97 (t, J=5.6 Hz, 2H), 3.38 (s, 1H), 3.00 (t, J=5.6 Hz, 2H). MS (ES−): 424 (M−H, 100). Anal. Calcd. for C₁₇H₁₃F₆NO₃S: C, 48.00; H, 3.08; N, 3.29. Found: C, 48.17; H, 3.06; N, 3.37.

In a similar manner, the following compounds were prepared, beginning with the tetrahydroquinoline and the appropriate (substituted)benzenesulfonyl chlorides.

13.3

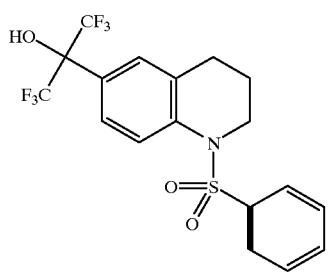

13.3

¹H NMR (CDCl₃): δ 7.86 (d, J=8.5 Hz, 1H), 7.62 (d, J=7.2 Hz, 2H), 7.55 (t, J=7.5 Hz, 1H), 7.48 (d, J=8.5 Hz, 1H), 7.41 (t, J=7.2 Hz, 2H), 7.36 (s, 1H), 3.81 (dd, J=6.5, 4.5 Hz, 2H), 3.40 (s, 1H), 2.52 (dd, J=7.0, 4.5 Hz, 2H), 1.70 (m, 2H), MS (ES−): 438 (M−H, 100). Anal. Calcd. for C₁₈H₁₅F₆NO₃S: C, 49.20; H, 3.44; N, 3.19; S, 7.30. Found: C, 49.55; H, 3.36; N, 3.31; S, 7.53.

13.4

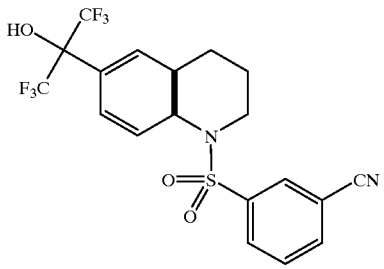

13.4

¹H NMR (CDCl₃): δ 7.90 (s, 1H), 7.81 (d, J=8.5 Hz, 2H), 7.80 (d, J=7.5 Hz, 1H), 7.55 (d, J=7.5 Hz, 1H), 7.50 (t, J=7.5 Hz, 1H), 7.36 (s, 1H), 3.82 (dd, J=6.5, 5.5 Hz, 2H), 3.35 (s, 1H), 2.55 (t, J=5.5 Hz, 2H), 1.72 (m, 2H). MS (ES-): 577 (M-H, 100). Anal. Calcd. for $C_{19}H_{14}F_6N_2O_3S$: C, 49.14; H, 3.04; N, 6.03; S, 6.91. Found: C, 49.25; H, 3.08; N, 5.86; 6.84.

Example 14

This example illustrates the synthesis of compound 14.1.

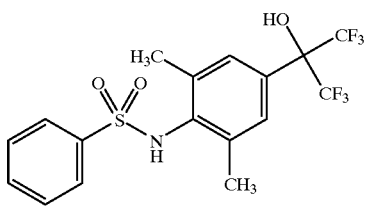

14.1

Hexafluoroacetone trihydrate (9.68 g, 44 mmol) was added to 2,6-dimethylaniline (4.84 g, 40 mmol) and p-toluenesulfonic acid (304 mg, 1.6 mmol) at room temperature. The mixture was stirred at 130° C. for 14 hours under a nitrogen atmosphere. After cooling down, the solidified mixture was washed with sodium bicarbonate solution, water, and hexane and dried to afford 10 g of 4-[2,2,2-trifluoro-1-hydroxy-1-(trifluoromethyl)ethyl]-2,6-dimethylaniline. ¹H NMR (DMSO): δ 8.11 (s, 1H), 7.08 (s, 2H), 4.89 (s, 2H), 2.10 (s, 6H). MS (ES) m/z 288.1 ([M+H]⁺).

To a solution of 4-[2,2,2-trifluoro-1-hydroxy-1-(trifluoromethyl)ethyl]-2,6-dimethylaniline (4.3 g, 15 mmol) and 2,6-lutidine (3.5 mL, 30 mmol) in acetone (25 mL), was added benzenesulfonyl chloride (3.18 g, 18 mmol). The mixture was stirred at room temperature for 20 hours, at 50° C. for 20 hours, and at 70° C. for 24 hours. After cooling down, the solid was filtered off. The filtrate was concentrated, and the residue was treated by 3N HCl (200 mL), and it was extracted with ethyl acetate. The organic layer was separated, washed with saturated sodium bicarbonate solution and brine, dried, and concentrated. The residue was purified by silica column chromatography (eluted by 9:1 DCM/EtOAc) to afford 5.1 g of product (example 14.1). ¹H NMR (DMSO): δ 9.52 (s, 1H), 8.64 (s, 1H), 7.69 (m, 3H), 7.59 (m, 2H), 7.31 (s, 2H), 1.99 (s, 6H). MS (ES) m/z 426.0 ([M-H]⁻). Anal. Calcd. for $C_{17}H_{15}F_6NO_3S$: C, 47.78; H, 3.54; N, 3.28. Found: C, 47.69; H, 3.45; N, 3.33.

Compounds 14.2–14.11 were prepared from their corresponding anilines in a manner similar to that described for 14.1.

14.2

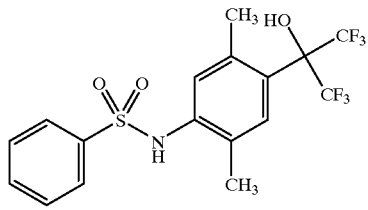

14.2

¹H NMR (DMSO): δ 9.75 (s, 1H), 8.42 (s, 1H), 7.72 (m, 2H), 7.66 (m, 1H), 7.57 (m, 2H), 7.18 (s, 1H), 6.91 (s, 1H), 2.40 (s, 3H), 1.97 (s, 3H). MS (EI) m/z 427 (M⁺). Anal. Calcd. for $C_{17}H_{15}F_6NO_3S$: C, 47.78; H, 3.54; N, 3.28. Found: C, 47.60; H, 3.57; N, 3.33.

14.3

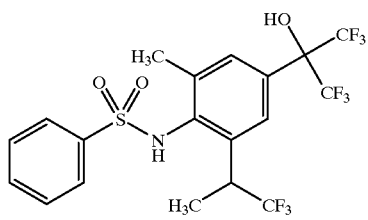

14.3

¹H NMR (DMSO): 9.59 (s, 1H), 8.65 (s, 1H), 7.72 (m, 2H), 7.66 (m, 1H), 7.58 (m, 2H), 7.39 (s, 1H), 7.29 (s, 1H), 3.17 (h, J=6.9 Hz, 1H), 1.98 (s, 3H), 0.93 (d, J=6.9 Hz, 6H). MS (EI) m/z 455 (M⁺). Anal. Calcd. for $C_{19}H_{19}F_6NO_3S$: C, 50.11; H, 4.21; N, 3.08. Found: C, 50.18; H, 4.23; N, 3.06.

14.4

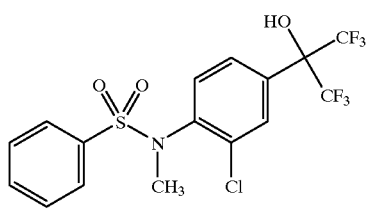

14.4

¹H NMR (CDCl₃): δ 7.78 (m, 3H), 7.65–7.50 (m, 4H), 7.34 (d, J=8.5 Hz, 1H), 3.54 (s, 1H), 3.23 (s, 3H). MS (EI) m/z 447 (M+). Anal. Calcd. for $C_{16}H_{12}ClF_6NO_3S$: C, 42.92; H, 2.70; N, 3.13; S, 7.16. Found: C, 43.19; H, 2.80; N, 3.16; S, 7.27.

14.5

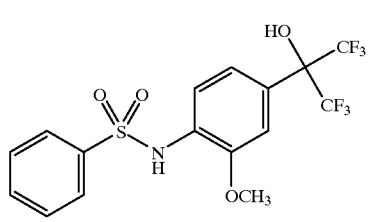

14.5

¹H-NMR (DMSO): δ 9.80 (s, 1H), 8.68 (s, 1H), 7.78 (d, J=7.12, 1.56 Hz, 2H), 7.56 (m, 3H), 7.33 (d, J=8.36, 1H), 7.15 (d, J=12.00 Hz, 2H), 3.59 (s, 3H). MS (ES+): 430 (M+H, 75). Anal. Calc. for $C_{16}H_{13}F_6NO_4S$: C, 44.76; H, 3.05; N, 3.26; S, 7.47. Found: C, 44.90; H, 3.10; N, 3.32; S, 7.57.

14.6

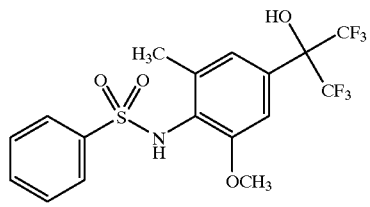

14.6

$^1$H-NMR (DMSO): δ 9.34 (s, 1H), 8.71 (s, 1H), 7.60(m, 5H), 7.12 (s, 1H), 6.91 (s, 1H), 3.17 (s, 3H), 2.33 (s, 3H). MS (ES+): 444 (M+H, 17). MS (ES−): 442 (M−H, 100). Anal. Calc. for $C_{17}H_{15}F_6NO_4S$: C, 46.05; H, 3.41; N, 3.16; S, 7.23. Found: C, 46.18; H, 3.50; N, 3.16; S, 7.33.

14.7

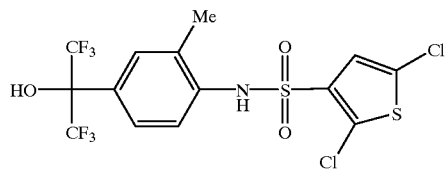

14.7

$^1$H-NMR (DMSO): δ 10.22 (s, 1H), 8.69 (s, 1H), 7.50 (m, 2H), 7.20 (m, 2H), 2.21 (s, 3H). MS (ES+): 488 (M+H, 15). Anal. Calc. for $C_{14}H_9Cl_2F_6NO_3S_2$: C, 34.44; H, 1.86; N, 2.87; Cl, 4.52; S, 13.13. Found: C, 34.65; H, 1.80; N, 2.69; Cl, 14.44; S, 13.02.

14.8

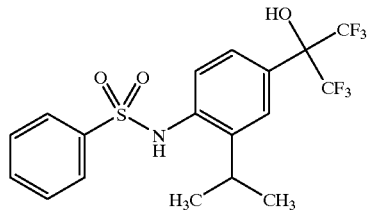

14.8

$^1$H-NMR (DMSO): δ 9.90 (s, 1H), 8.65 (s, 1H), 7.6 (m, 6H), 7.36 (d, J=8.40 Hz, 1H), 7.08 (d, J=8.48 Hz, 1H), 3.17 (m, 1H), 0.90 (d, J=6.80 Hz, 6H). MS (ES−): 440 (M−H, 100). Anal. Calc. for $C_{18}H_{17}F_6NO_3S$: C, 48.98; H, 3.88; N, 3.17; S, 7.26. Found: C, 49.03; H, 3.83; N, 3.18; S, 7.37.

14.9

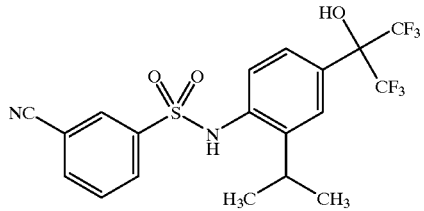

14.9

$^1$H-NMR (DMSO): δ 10.14 (s, 1H), 8.69 (s, 1H), 8.15 (d, J=7.76 Hz, 1H), 8.01 (m, 2H), 7.81 (t, J=7.72 Hz, 1H), 7.54 (s, 1H), 7.40 (d, J=8.44 Hz, 1H), 7.04 (d, J=8.64 Hz, 1H), 3.15 (m, 1H), 0.94 (d, J=6.88 Hz, 6H). MS (ES−): 465 (M−H, 100). Anal. Calc. for $C_{19}H_{16}F_6N_2O_3S$: C, 48.93; H, 3.46; N, 6.01; S, 6.88. Found C, 48.99; H, 3.39; N, 5.84; S, 6.82.

14.10

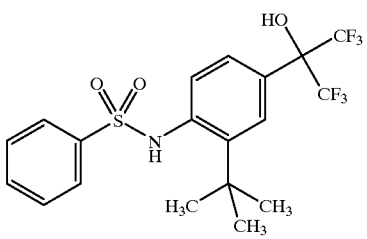

14.10

$^1$H-NMR (DMSO): δ 9.44 (s, 1H), 8.71 (s, 1H), 7.90 (m, 2H), 7.70 (m, 4H), 7.30 (m, 1H), 6.65 (d, J=8.44 Hz, 1H), 1.43 (s, 9H). MS (ES−): 454 (M−H, 100). Anal. Calc. for $C_{19}H_{19}F_6NO_3S$: C, 50.11; H, 4.21; N, 3.08; S, 7.04. Found: C, 50.18; H, 4.22; N, 3.07; S, 7.04.

14.11

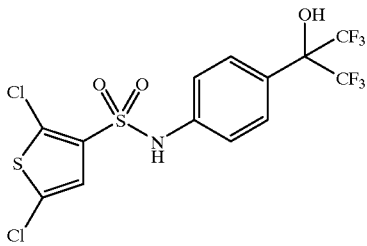

14.11

$^1$H-NMR (DMSO): δ 11.06 (s, 1H), 8.64 (s, 1H), 7.60 (d, J=9 Hz, 2H), 7.39 (s, 1H), 7.25 (d, J=9 Hz, 2H). Anal. Calc. for $C_{14}H_9Cl_2F_6NO_3S_2$: C, 32.92; H, 1.49; N, 2.95; S, 13.52. Found: C, 33.06; H, 1.44; N, 2.89; S, 13.53.

Example 15

This example illustrates the preparation of compound 15.1

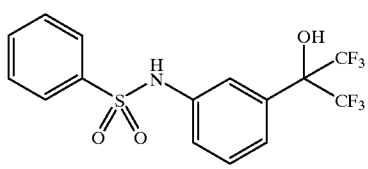

15.1

Fuming nitric acid (90%, 5 mL) was added drop wise to 1,1,1,3,3,3-hexafluoro-2-phenyl-2-propanol (4.2 mL, 25 mmol) in concentrated suifliic acid (15 mL) at 0° C. The mixture was stirred at 0° C. for 30 minutes, and at room temperature for 2 hours. Then it was poured into ice water. The solid was fitered, washed with sodium bicarbonate solution, water, and hexane, and dried to give 6.2 g of 1-[2,2,2-trifluoro-1-hydroxy-1-(trifluoromethyl)ethyl]-3-nitrobenzene. $^1$H NMR (CDCl$_3$): δ 8.66 (s, 1H), 8.38 (d, J=8 Hz, 1H), 8.06 (d, J=8 Hz, 1H), 7.69 (t, J=8 Hz, 1H), 3.66 (bs, 1H). MS (EI) m/z 289 (M$^+$).

Palladium on carbon (10%, 150 mg) was added to the product above (2.0 g, 6.9 mmol) in ethanol (20 mL). The mixture was stirred under 1 atmosphere of hydrogen at room temperature for 6 hours. The catalyst was filtered off through celite. The filtrate was concentrated to give 1.78 g of solid product (3-[2,2,2-trifluoro-1-hydroxy-1-(trifluoromethyl) ethyl]aniline). $^1$H NMR (DMSO): δ 8.36 (s, 1H), 7.11 (t, J=8 Hz, 1H), 6.93 (s, 1H), 6.78 (d, J=8 Hz, 1H), 6.66 (d, J=8 Hz, 1H), 5.40 (bs, 1H). MS (EI) m/z 259 (M$^+$).

To a solution of the above product (770 mg, 3 mmol) and 2,6-lutidine (0.7 mL, 6 mmol) in acetone (10 mL), was added benzenesulfonyl chloride (0.46 mL, 3.6 mmol). The mixture was stirred at room temperature for 20 hours. The solid was filtered off. The filtrate was concentrated, and the residue was treated by 3N HCl (100 mL), and it was extracted with ethyl acetate. The organic layer was separated, washed with saturated sodium bicarbonate solution and brine, dried, and concentrated. The residue was purified by silica column chromatography (eluted by 1:2 EtOAc/Hexane) to afford 1.08 g of 15.1. $^1$H NMR (CDCl$_3$): δ 7.73 (d, J=7.2 Hz, 2H), 7.54 (m, 1H), 7.45 (m, 3H), 7.35 (m, 2H), 7.24 (s, 1H), 6.52 (s, 1H), 3.39 (s, 1H). MS (ES) m/z 398.0 ([M–H]$^-$). Anal. Calcd. for C$_{15}$H$_{11}$F$_6$NO$_3$S: C, 45.12; H, 2.78; N, 3.51; S, 8.03. Found: C, 45.27; H, 2.88; N, 3.49; S, 8.05.

Compound 15.2 was prepared in a manner the same as that described above except that 3-(2,5-dimethylthienyl)sulfonyl chloride was used instead of benzenesulfonyl chloride.

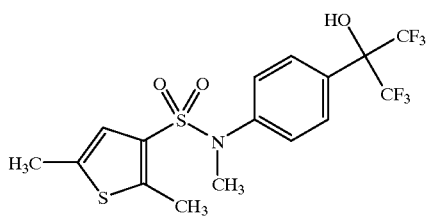

15.2

$^1$H NMR (CDCl$_3$): δ 7.51 (m, 1H), 7.39 (m, 2H), 7.23 (m, 1H), 6.81 (s, 1H), 6.60 (s, 1H), 3.66 (s, 1H), 2.35 (s, 3H), 2.33 (s, 3H). MS (EI) m/z 433 (M$^+$). Anal. Calcd. for C$_{15}$H$_{13}$F$_6$NO$_3$S$_2$: C, 41.57; H, 3.02; N, 3.23. Found: C, 41.70; H, 3.02; N, 3.20.

Example 16

This example illustrates the preparation of compound 16.1

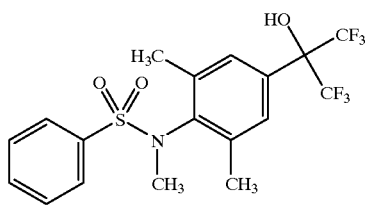

16.1

Sodium hydride (60%, 116.4 mg, 2.91 mmol) was added to compound 14.1 (1.13 g, 2.65 mmol) in DMF (10 mL) at room temperature. The mixture was stirred at room temperature for 20 minutes. Then iodomethane (0.18 ml, 2.91 mmol) was added. The mixture was stirred at room temperature for 2 hours. DMF was evaporated under vacuum, and the residue was treated with water, which was extracted with EtOAc. The organic layer was separated, washed with brine, dried, and concentrated. The residue was purified by silica column chromatography (eluted by 1;5 EtOAc/Hexane) to afford 1.06 g of product.

$^1$H NMR (CDCl$_3$): δ 7.82 (m, 2H), 7.60 (m, 1H), 7.52 (m, 2H), 7.38 (s, 2H), 3.85 (bs, 1H), 3.18 (s, 3H), 2.12 (s, 6H). MS (ES) m/z 440.0 ([M–H]$^-$). Anal. Calcd. for C$_{18}$H$_{17}$F$_6$NO$_3$S: C, 48.98; H, 3.88; N, 3.17. Found: C, 49.12; H, 3.86; N, 3.26.

Compounds 16.2–16.38 were prepared in a manner similar to that described for 16.1.

16.2

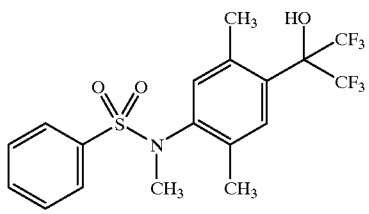

16.2

$^1$H NMR (DMSO): δ 8.55 (s, 1H), 7.77 (m, 1H), 7.68 (m, 4H), 7.38 (s, 1H), 6.53 (s, 1H), 3.07 (s, 3H), 2.36 (s, 3H), 2.26 (s, 3H). MS (EI) m/z 441 (M$^+$). Anal. Calcd. for C$_{18}$H$_{17}$F$_6$NO$_3$S: C, 48.98; H, 3.88; N, 3.17. Found: C, 49.20; H, 3.93; N, 3.16.

16.3

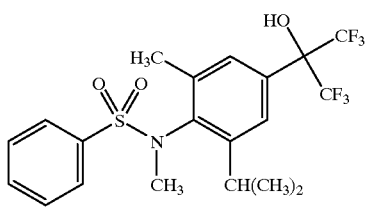

16.3

$^1$H NMR (DMSO): δ 8.73 (s, 1H), 7.85 (m, 2H), 7.74 (m, 1H), 7.66 (m, 2H), 7.45 (s, 1H), 7.37 (s, 1H), 3.14 (s, 3H), 2.90 (h, J=6.9 Hz, 1H), 2.05 (s, 3H), 1.06 (dd, J=6.9 Hz, 6H). MS (ES) m/z 468.1 ([M–H]$^-$). Anal. Calcd. for C₂₀H₂₁F₆NO₃S: C, 51.17; H, 4.51; N, 2.98. Found: C, 51.18; H, 4.54; N, 3.10.

16.4

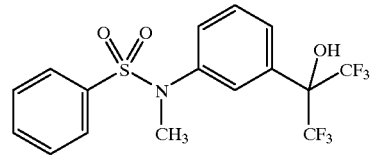

¹H NMR (CDCl₃): δ 7.65–7.30 (m, 9H), 3.40 (s, 1H), 3.19 (s, 3H). MS (ES) m/z 412.0 ([M–H]⁻). Anal. Calcd. for C₁₆H₁₃F₆NO₃S: C, 46.49; H, 3.17; N, 3.39; S, 7.76. Found: C, 46.74; H, 3.30; N, 3.35; S, 7.79.

16.5

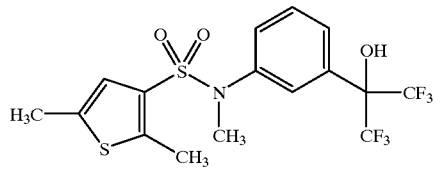

¹H NMR (CDCl₃): δ 7.63 (m, 1H), 7.43 (m, 3H), 6.67 (s, 1H), 3.37 (s, 1H), 3.24 (s, 3H), 2.36 (s, 3H), 2.05 (s, 3H). MS (EI) m/z 447 (M⁺). Anal. Calcd. for C₁₆H₁₅F₆NO₃S₂: C, 42.95; H, 3.38; N, 3.13; S, 14.33. Found: C, 43.00; H, 3.29; N, 3.08; S, 14.44.

16.6

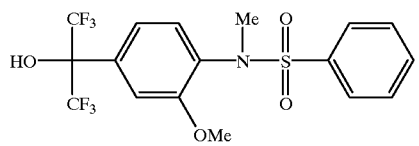

¹H-NMR (DMSO): δ 8.84 (s, 1H), 7.60 (m, 5H), 7.32 (d, J=8.92 Hz, 1H), 7.22(m, 2H), 3.44 (s, 1H), 3.12 (s, 1H). MS (ES–): 442 M–H, 100). Anal. Calc. for C₁₇H₁₅F₆NO₄S: C, 46.05; H, 3.41; N, 3.16; S, 7.23. Found: C, 46.14; H, 3.43; N, 3.15; S,7.34.

16.7

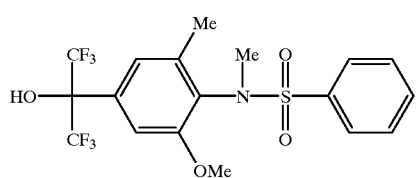

¹H-NMR (DMSO): δ 8.78 (s, 1H), 7.70 (m, 3H), 7.60 (m, 2H), 7.17 (s, 1H), 7.01(s, 1H), 3.26 (s, 3H), 3.07 (s, 3H), 2.38 (s, 3H). MS (ES–): 456 (M–H, 100). Anal. Calc. for C₁₈H₁₇F₆NO₄S: C, 47.27; H, 3.75; N, 3.06; S, 7.01. Found: C, 47.32; H, 3.75; N, 3.07; S, 7.08.

16.8

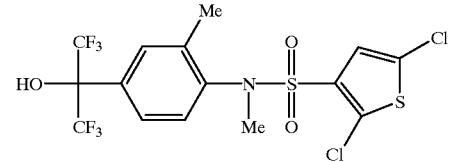

¹H-NMR (DMSO): δ 8.80 (s, 1H), 7.63 (s, 1H), 7.50 (d, J=8.52 Hz, 1H), 7.32 (s, 1H), 7.14 (d, J=8.52 Hz, 1H), 3.23 (s, 3H), 2.37 (s, 3H). MS (ES+): 502 (M+H, 100). Anal. Calc. for C₁₅H₁₁Cl₂F₆NO₃S₂: C, 35.87; H, 2.21; N, 2.79; Cl, 14.12; S, 12.77. Found: C, 35.95; H, 2.10; N, 2.63; Cl, 14.12; S, 12.88.

16.9

¹H-NMR (DMSO): δ 8.77 (s, 1H), 7.62 (d, J=8.44 Hz, 2H), 7.50 (m, 1H), 7.40 (d, J=8.96 Hz, 2H), 7.36 (s, 1H), 7.31 (s, 1H), 7.0 (m, 1H), 4.96 (m, 2H), MS (ES–): 568 (M–H, 56). Anal. Calc. for C₁₈H₁₁Cl₂F₆NO₃S₃: C, 37.90; H, 1.94; N, 2.46; Cl, 12.43; S, 16.87. Found: C, 37.84; H, 1.81; N, 2.38; Cl, 12.52; S, 16.96.

16.10

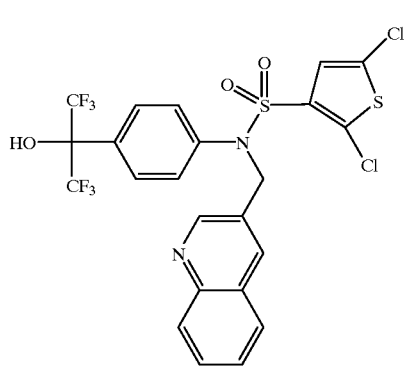

¹H-NMR (DMSO): δ 8.74 (s, 1H), 8.36 (d, J=8.4 Hz, 1H), 7.94 (d, J=8.04 Hz, 1H), 7.88 (d, J=8.4 Hz, 1H), 7.70 (m, 1H), 7.6 (m, 6H), 7.42 (s, 1H), 5.29(s, 2H). MS (ES–): 613 (M–H, 83). Anal. Calc. for C₂₃H₁₄Cl₂F₆N₂O₃S₂: C, 44.89; H, 2.29; N, 4.55; Cl, 11.52; S, 10.42. Found: C, 45.32; H, 2.33; N, 4.51; Cl, 11.31; S, 10.22.

16.11

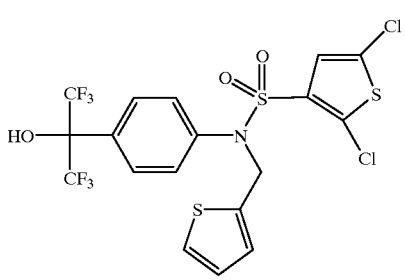

¹H-NMR (DMSO): δ 8.78 (s, 1H), 7.64 (d, J=8.8 Hz, 2H), 7.40(m, 4H), 6.9(m, 2H), 5.17 (s, 2H). MS (ES−): 568 (M−H, 20). Anal. Calc. for $C_{18}H_{11}Cl_2F_6NO_3S_3$: C, 37.90; H, 1.94; N, 2.46; Cl, 12.43; S, 16.87. Found: C, 37.63; H, 1.88; N, 2.45; Cl, 12.68; S, 16.77.

16.12

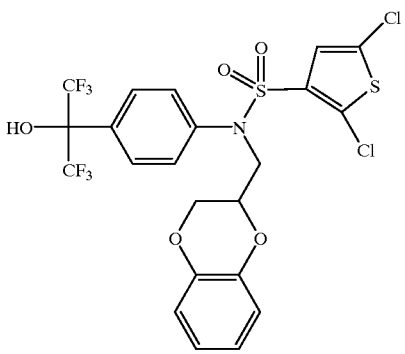

¹H-NMR (DMSO): δ 8.82 (s, 1H), 7.68 (d, J=8.44 Hz, 2H), 7.47(d, J=8.8 Hz, 2H), 7.34 (s, 1H), 6.8(m, 3H), 6.58(m, 1H), 4.25(m, 2H), 4.06(m, 3H), MS (ES−): 620 (M−H, 100). Anal. Calc. for $C_{22}H_{15}Cl_2F_6NO_5S_2$: C, 42.46; H, 2.43; N, 2.25; Cl, 11.39; S, 10.30. Found: C, 42.55; H, 2.34; N, 2.27; Cl, 11.46; S, 10.22.

16.13

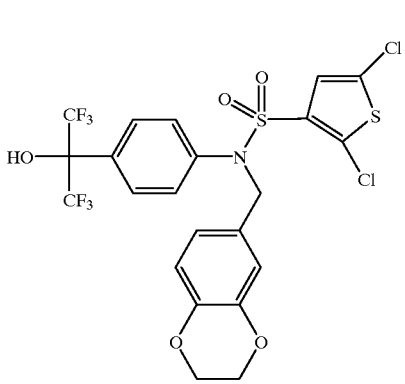

¹H-NMR (DMSO): δ 8.77 (s, 1H), 7.62 (d, J=8.44 Hz, 2H), 7.40 (m, 3H), 6.70(m, 3H), 4.85(s, 2H), 4.17(s, 4H). MS (ES−): 620 (M−H, 100). Anal. Calc. for $C_{22}H_{11}Cl_2F_6NO_5S_2$: C, 42.46; H, 2.43; N, 2.25; Cl, 11.39; S, 10.30. Found: C, 42.54; H, 2.47; N, 2.18; Cl, 11.35; S, 10.39.

16.14

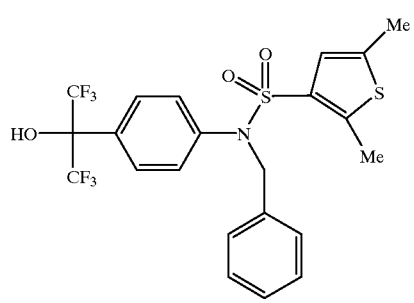

¹H-NMR (DMSO): δ 8.73 (s, 1H), 7.58 (d, J=8.8 Hz, 2H), 7.28(m, 7H), 6.97 (d, J=1.12 Hz, 1H), 4.86 (s, 2H), 2.41 (s, 3H), 1.93 (s, 3H). MS (ES+): 524 (M+H, 100). Anal. Calc. for $C_{22}H_{19}F_6NO_3S_2$: C, 50.47; H, 3.66; N, 2.68; S, 12.25. Found: C, 50.57; H, 3.58; N, 2.60; S, 12.35.

16.15

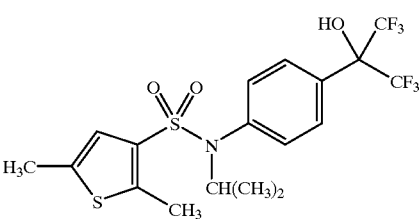

¹H-NMR (DMSO): δ 8.84 (s, 1H), 7.44 (d, J=8.44 Hz, 2H), 7.24(d, J=8.68 Hz, 2H), 6.90 (s, 1H), 4.41 (m, 1H), 2.39 (s, 3H), 2.20 (s, 3H), 1.02 (d, J=6.72 Hz, 6H), MS (ES+): 476 M+H, 100).). Anal. Calc. for $C_{18}H_{19}F_6NO_3S_2$: C, 45.47; H 4.03; N, 2.95; S, 13.49. Found: C, 45.66; H, 4.10; N, 2.90; S, 13.58.

16.16

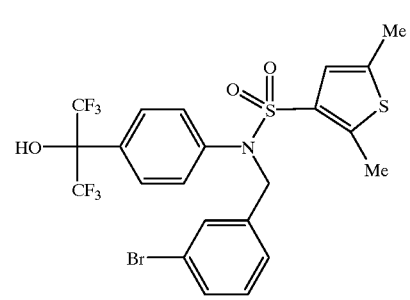

¹H-NMR (DMSO): δ 8.76 (s, 1H), 7.60 (d, J=8.52 Hz, 2H), 7.46(s, 1H), 7.40(m, 1H), 7.32(m, 3H), 7.24(t, 1H), 6.96 (s, 1H), 4.87 (s, 2H), 2.41 (s, 3H), 1.93 (s, 3H). MS (ES−): 600 (M−H, 60). Anal. Calc. for $C_{22}H_{18}BrF_6NO_3S_2$: C, 43.86; H, 3.01; N, 2.33; S, 10.65. Found: C, 43.83; H, 2.87; N, 2.36; S, 10.81.

16.17

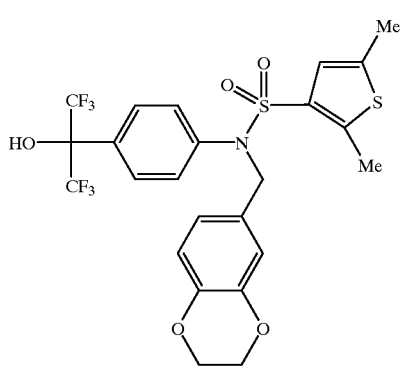

¹H-NMR (DMSO): δ 8.75 (s, 1H), 7.60 (d, J=8.45 Hz, 2H), 7.30 (d, J=8.88 Hz, 2H), 6.94(s, 1H), 6.73(m, 3H), 4.73(s, 2H), 4.16(s, 4H), 2.40 (s, 3H), 1.91 (s, 3H). MS (ES-): 580 (M-H, 80). Anal. Calc. for C₂₄H₂₁F₆NO₅S₂: C, 49.57; H, 3.64; N, 2.41; S, 11.03. Found: C, 49.39; H, 3.77; N, 2.48; S, 11.01.

16.18

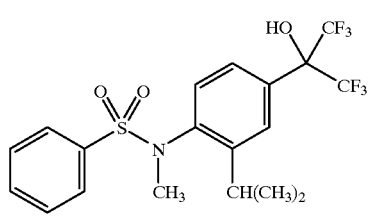

¹H-NMR (DMSO): δ 8.79 (s, 1H), 7.70 (m, 6H), 7.40 (m, 1H), 6.76 (d, J=8.50 Hz, 1H), 3.49 (m, 1H), 3.11 (s, 3H), 1.20 (m, 6H). MS (ES-): 454 (M-H, 100). Anal. Calc. for C₁₉H₁₉F6NO₃S: C, 50.11; H, 4.21; N, 3.08; S, 7.04. Found: C, 50.12; H, 4.18; N, 3.09; S, 7.12.

16.19

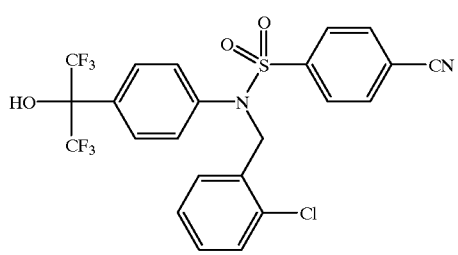

¹H-NMR (DMSO): δ 8.76 (s, 1H), 8.21 (m, 1H), 8.11 (s, 1H), 7.90 (d, J=8.08 Hz, 1H), 7.79 (m, 1H), 7.58 (m, 2H), 7.32 (m, 6H), 4.99 (s, 2H), MS (ES-): 547 (M-H, 100). Anal. Calc. for C₂₃H₁₅ClF₆N₂O₃S: C, 50.33; H, 2.75; N, 5.10; Cl, 6.46; S, 5.84. Found: C, 50.49; H, 2.80; N, 5.09; Cl, 6.54; S, 5.73.

16.20

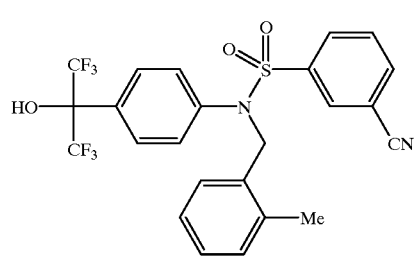

¹H-NMR (DMSO): δ 8.73 (s, 1H), 8.21 (d, J=8.60 Hz, 1H), 8.07 (s, 1H), 7.81 (m, 2H), 7.54 (d, J=8.44 Hz, 2H), 7.26 (d, J=8.80 Hz, 2H), 7.10 (m, 3H), 7.00 (m, 1H), 4.88 (s, 2H), 2.28 (s, 3H). MS ES-): 527 (M-H, 90). Anal. Calc. for C₂₄H₁₈F₆N₂O₃S: C, 54.55; H, 3.43; N, 5.30; S, 6.07. Found: C, 54.05; H, 3.46; N, 5.26; S, 5.97.

16.21

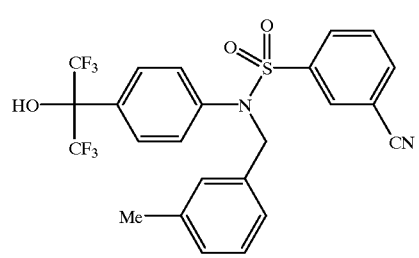

¹H-NMR (DMSO): δ 8.74 (s, 1H), 8.21 (m, 1H), 8.10 (s, 1H), 7.87 (m, 2H), 7.58 (d, J=8.48 Hz, 2H), 7.28 (d, J=8.84 Hz, 2H), 7.13 (m, 1H), 7.02 (m, 3H), 4.85 (s, 2H), 2.21 (s, 3H). MS (ES-): 527 (M-H, 100). Anal. Calc. for C₂₄H₁₈F₆N₂O₃S: C, 54.55; H, 3.43; N, 5.30; S, 6.07. Found: C, 54.59; H, 3.47; N, 5.24; S, 6.00.

16.22

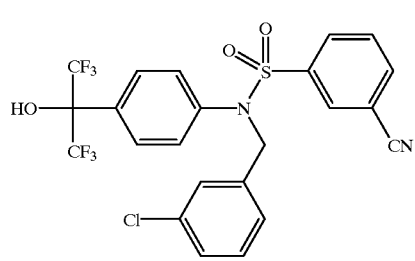

¹H-NMR (DMSO): δ 8.77 (s, 1H), 8.30 (m, 1H), 8.15 (s, 1H), 7.84 (m, 2H), 7.60 (d, J=8.44 Hz, 2H), 7.27 (m, 6H), 4.92 (s, 2H). MS (ES-): 547 (M-H, 100). Anal. Calc. for C₂₃H₁₅ClF₆N₂O₃S: C, 50.33; H, 2.75; N, 5.10; Cl, 6.46; S, 5.84. Found: C, 50.26; H, 2.77; N, 5.07; Cl, 6.50; S, 5.82.

16.23

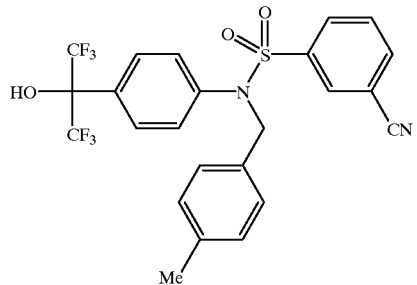

16.23

¹H-NMR (DMSO): δ 8.74 (s, 1H), 8.20 (d, J=7.32 Hz, 1H), 8.09 (s, 1H). 7.85 (m, 2H), 7.57 (d, J=8.12 Hz, 2H), 7.27 (d, J=8.40 Hz, 2H), 7.11 (m, 4H), 4.85 (s, 2H), 2.21 (s, 3H). MS (ES-): 527 M-H, 60). Anal. Calc. for $C_{24}H_{18}F_6N_2O_3S$: C, 54.55; H, 3.43; N, 5.30; S, 6.07. Found: C, 54.56; H, 3.39; N, 5.29; S, 5.98.

16.24

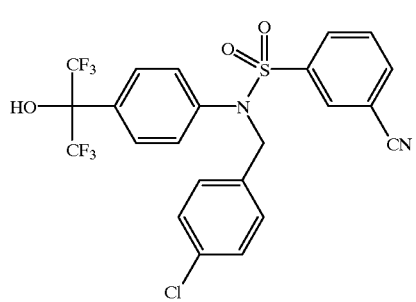

16.24

¹H-NMR (DMSO): δ 8.76 (s, 1H), 8.21 (m, 1H), 8.13 (d, J=1.60 Hz, 1H), 7.83 (m, 2H), 4.92 (s, 2H), 7.58 (d, J=8.44 Hz, 2H), 7.30 (m, 6H), 4.90 (s, 2H). MS (ES-): 547 (M-H, 100). Anal. Calc. for $C_{23}H_{15}ClF_6N_2O_3S$: C, 50.33; H, 2.75; N, 5.10; Cl, 6.46; S, 5.84. Found: C, 50.42; H, 2.75; N, 5.01; Cl, 6.53; S, 5.76.

16.25

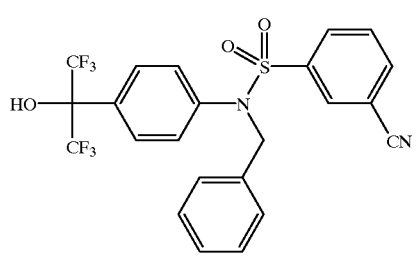

16.25

¹H-NMR (DMSO): δ 8.74 (s, 1H), 8.21 (m, 1H), 8.11 (d, J=1.48 Hz, 1H), 7.85 (m, 2H), 7.57 (d, J=8.44 Hz, 2H), 7.26 (m, 7H), 4.91 (s, 2H). MS (ES-): 513 (M-H, 100). Anal. Calc. for $C_{23}H_{16}F_6N_2O_3S$: C, 53.70; H, 3.13; N, 5.45; S, 6.23. Found: C, 53.65; H, 3.04; N, 5.33; S, 6.09.

16.26

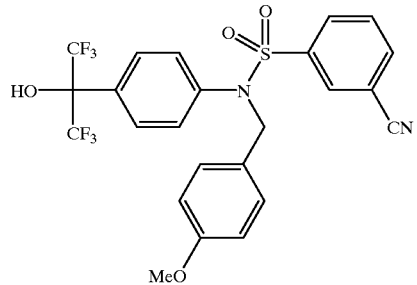

16.26

¹H-NMR (DMSO): δ 8.75 (s, 1H), 8.21 (m, 1H), 8.08 (s, 1H), 7.83 (m, 2H), 7.57 (d, J=8.44 Hz, 2H), 7.27 (m, 2H), 7.15 (m, 2H), 6.81 (m, 2H), 4.82 (s, 2H), 3.67 (s, 3H). MS (ES-): 543 (M-H, 54). Anal. Calc. for $C_{24}H_{18}F_6N_2O_4S$: C, 52.94; H, 3.33; N, 5.15; S, 5.89. Found: C, 52.89; H, 3.37; N, 5.12; S, 5.97.

16.27

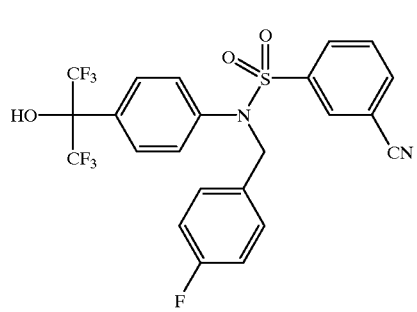

16.27

¹H-NMR (DMSO): δ 8.76 (s, 1H), 8.23 (m, 1H), 8.12 (d, J=1.76 Hz, 1H), 7.86 (m, 2H), 7.58 (d, J=8.40 Hz, 2H), 7.28 (m, 4H), 7.10 (m, 2H), 4.89 (s, 2H). MS (ES-): 531 (M-H, 100). Anal. Calc. for $C_{23}H_{15}F_7N_2O_3S$: C, 51.88; H, 2.84; N, 5.26; S, 6.02. Found: C, 51.91; H, 2.83; N, 5.25; S, 6.09.

16.28

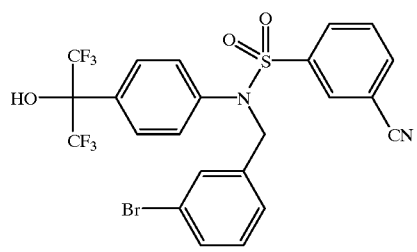

16.28

¹H-NMR (DMSO): δ 8.76 (s, 1H), 8.23 (m, 1H), 8.14 (d, J=1.72 Hz, 1H), 7.80 (m, 2H), 7.60 (d, J=8.32 Hz, 2H), 7.41 (m, 2H), 7.30 (m, 4H), 4.91 (s, 2H). MS (ES-): 593 (M-H, 100). Anal. Calc. for $C_{23}H_{15}BrF_6N_2O_3S$: C, 46.56; H, 2.55; N, 4.72; S, 5.40. Found: C, 46.71; H, 2.56; N, 4.67; S, 5.22.

16.29

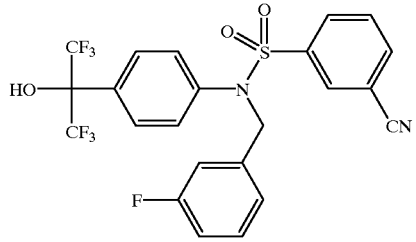

¹H-NMR (DMSO): δ 8.76 (s, 1H), 8.23 (m, 1H), 8.14 (d, J=1.28 Hz, 1H), 7.87 (m, 2H), 7.59 (d, J=8.40 Hz, 2H), 7.31 (m, 3H), 7.10 (m, 3H), 4.93 (s, 2H). MS (ES−): 531 (M−H, 100). Anal. Calc. for $C_{23}H_{15}F_7N_2O_3S$: C, 51.88; H, 2.84; N, 5.26; S, 6.02. Found: C, 51.89; H, 2.88; N, 5.23; S, 5.89.

16.30

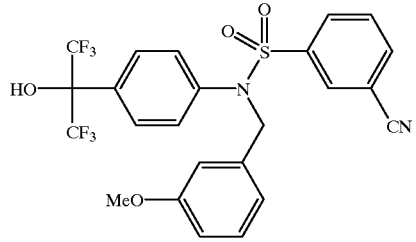

¹H-NMR (DMSO): δ 8.75 (s, 1H), 8.22 (m, 1H), 8.12 (s, 1H), 7.89 (d, J=8.08 Hz, 1H), 7.80 (m, 1H), 7.58 (d, J=8.40 Hz, 2H), 7.31 (m, 2H), 7.18 (m, 1H), 6.82 (d, J=7.68 Hz, 1H), 6.76 (m, 2H), 4.88 (s, 2H), 3.66 (s, 3H). MS (ES−): 543 M−H, 54). Anal. Calc. for $C_{24}H_{18}F_6N_2O_4S$: C, 52.94; H, 3.33; N, 5.15; S, 5.89. Found: C, 53.15; H, 3.50; N, 5.15; S, 5.80.

16.31

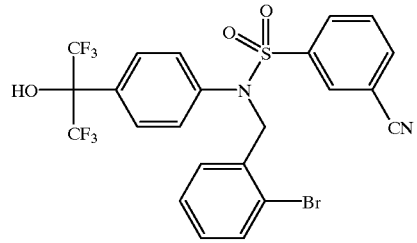

¹H-NMR (DMSO): δ 8.76 (s, 1H), 8.23 (m, 1H), 8.09 (d, J=1.24 Hz, 1H), 7.90 (d, J=8.16 Hz, 1H), 7.80 (m, 1H), 7.57 (m, 3H), 7.46 (d, J=7.60 Hz, 1H), 7.30 (m, 3H), 7.17 (m, 1H), 4.97 (s, 2H). MS (ES−): 593 (M−H, 30). Anal. Calc. for $C_{23}H_{15}BrF_6N_2O_3S$: C, 46.56; H, 2.55; N, 4.72; S, 5.40. Found: C, 46.63; H, 2.57; N, 4.73; S, 5.36.

16.32

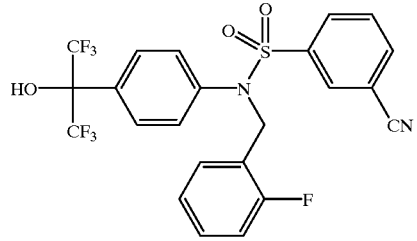

¹H-NMR (DMSO): δ 8.76 (s, 1H), 8.21 (m, 1H), 8.11 (s, 1H), 7.85 (m, 2H), 7.59 (m, 2H), 7.30 (m, 4H), 7.10 (m, 2H), 4.95 (s, 2H). MS (ES−): 531 (M−H, 100). Anal. Calc. for $C_{23}H_{15}F_7N_2O_3S$: C, 51.88; H, 2.84; N, 5.26; S, 6.02. Found: C, 51.83; H, 2.78; N, 5.16; S, 6.01.

16.33

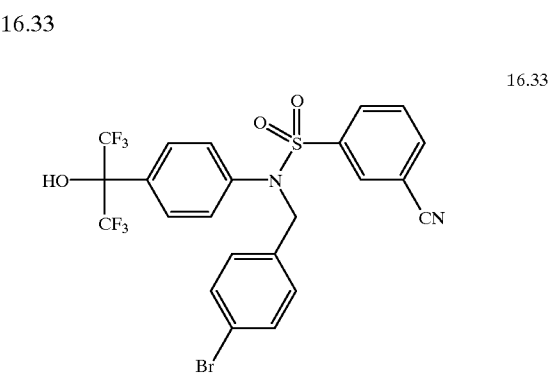

¹H-NMR (DMSO): δ 8.76 (s, 1H), 8.23 (m, 1H), 8.12 (d, J=1.40 Hz, 1H), 7.80 (m, 2H), 7.58 (d, J=8.72 Hz, 2H), 7.47 (m, 2H), 7.30 (d, J=8.88 Hz, 2H), 7.22 (d, J=8.52 Hz, 2H), 4.89 (s, 2H). MS (ES−): 593 (M−H, 30). Anal. Calc. for $C_{23}H_{15}BrF_6N_2O_3S$: C, 46.56; H, 2.55; N, 4.72; S, 5.40. Found: C, 46.73; H, 2.51; N, 4.53; S, 5.31.

16.34

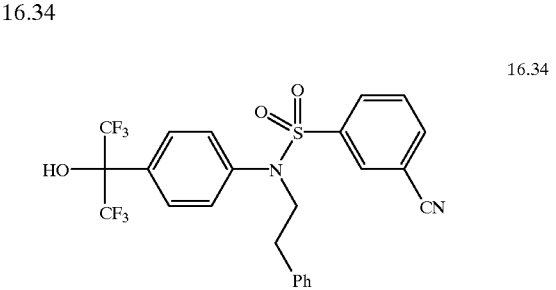

¹H-NMR (DMSO): δ 8.82 (s, 1H), 8.15 (dd, J=1.64, 7.04 Hz, 1H), 7.95 (s, 1H), 7.76 (m, 2H), 7.66 (d, J=8.40 Hz, 2H), 7.27 (m, 5H), 7.11 (d, J=6.88 Hz, 2H), 3.92 (t, J=7.64 Hz, 2H), 2.67 (t, J=7.32 Hz, 2H). MS (ES−): 527 (M−H, 54). Anal. Calc. for $C_{24}H_{18}F_6N_2O_3S$: C, 54.55; H, 3.43; N, 5.30; S, 6.07. Found: C, 54.64; H, 3.37; N, 5.25; S, 6.10.

16.35

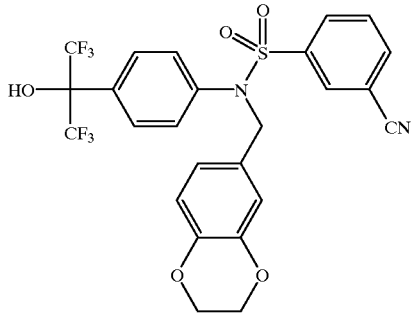

16.35

¹H-NMR (DMSO): δ 8.76 (s, 1H), 8.20 (d, J=6.44 Hz, 1H), 8.08 (s, 1H), 7.82 (m, 2H), 7.59 (d, J=8.36 Hz, 2H), 7.29 (m, 2H), 6.71 (m, 3H), 4.78 (s, 2H), 4.17 (s, 4H). MS (ES-): 571 (M-H, 100). Anal. Calc. for $C_{25}H_{18}F_6N_2O_5S$: C, 52.45; H, 3.17; N, 4.89; S, 5.60. Found: C, 52.34; H, 3.13; N, 4.80; S, 5.46.

16.36

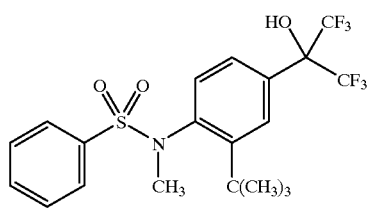

16.36

¹H-NMR (DMSO): δ 8.81 (s, 1H), 7.88 (s, 1H), 7.75 (m, 5H), 7.39 (m, 1H), 6.61 (m, 1H), 3.06 (s, 3H), 1.49 (s, 9H). MS (ES-): 468 (M-H, 100). Anal. Calc. for $C_{20}H_{21}F_6NO_3S$: C, 51.57; H, 4.51; N, 2.98; S, 6.83. Found: C, 51.14; H, 4.55; N, 2.96; S, 6.77.

16.37

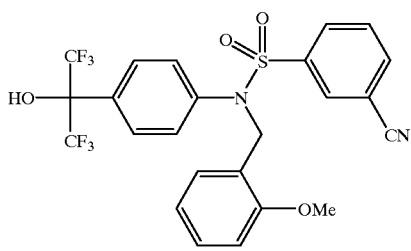

16.37

¹H-NMR (DMSO): δ 9.75 (s, 1H), 8.19 (m, 1H), 8.098 (d, J=1.64 Hz, 1H), 7.91 (m,1H), 7.80 (t, J=7.88 Hz, 1H), 7.58 (d, J=8.52 Hz, 2H), 7.25 (m, 4H), 6.86 (m, 2H), 4.84 (s, 2H), 3.55 (s, 3H). MS (ES-): 453 (M-H, 92). Anal. Calc. for $C_{24}H_{18}F_6N_2O_4S$: C, 52.94; H, 3.33; N, 5.15; S, 5.89. Found: C, 53.00; H, 3.21; N, 5.13; S, 5.91.

16.38

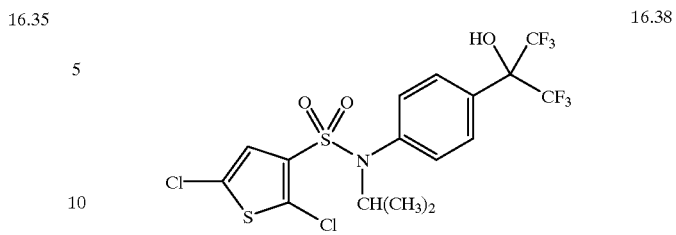

16.38

¹H NMR (CDCl₃): δ 7.74 (d, J=8.7 Hz, 2H), 7.22 (d, J=8.7 Hz, 2H), 6.93 (s, 1H), 4.12 (h, J=6.7 Hz, 1H), 3.55 (s, 1H), 1.15 (d, J=6.7 Hz, 6H). MS (EI) m/z 515 (M+). Anal. Calcd. for $C_{16}H_{13}Cl_2F_6NO_3S_2$: C, 37.22; H, 2.54; N, 2.71; S, 12.42. Found: C, 37.33; H, 2.47; N, 2.65; S, 12.48.

Example 17

This example illustrates the preparation of compound 17.1

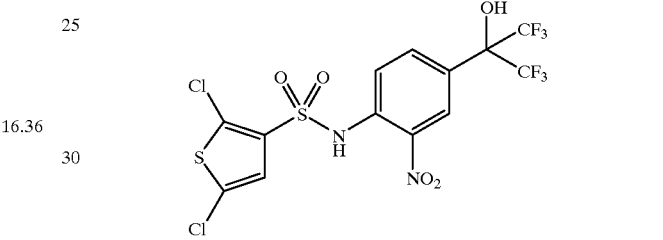

17.1

Nitric acid (90%, 0.2 mL) was added to compound 14.11 (273 mg, 0.5 mmol) in acetic acid (2 mL) at 0° C. The mixture was stirred at room temperature for 18 hour, at 60° C. for 6 hours, and at 100° C. for 3 hours. The mixture was poured into ice and extracted with EtOAc. The organic layer was washed with sodium bicarbonate solution and 0.1 N HCl, dried, and concentrated. The residue was purified by silica column chromatography (eluted with 1:5 EtOAc/Hexane) to give 210 mg of product.

¹H NMR (CDCl₃): δ 10.35 (s, 1H), 8.63 (s, 3H), 7.93 (d, J=9 Hz, 1H), 7.86 (d, J=9 Hz, 1H), 7.23 (s, 1H), 3.90 (s, 1H). MS (ES) m/z 516.9 ([M−H]⁻). Anal. Calcd. for $C_{13}H_6Cl_2F_6N_2O_5S_2 \cdot 1/3EtOAc$: C, 31.38; H, 1.59; N, 5.11; S, 11.69. Found: C, 31.53; H, 1.58; N, 5.09; S, 11.85.

Example 18

This example illustrates the preparation of compound 18.1.

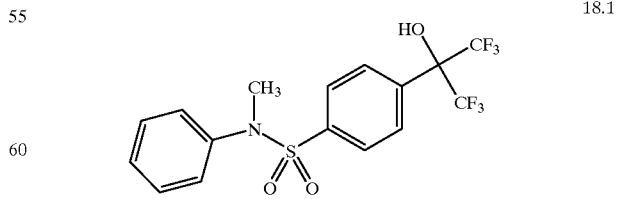

18.1

A mixture of N-methylaniline (1.08 mL, 10 mmol), pipsyl chloride (3.02 g, 10 mmol), and 2,6-lutidine (2.33 mL, 20 mmol) in acetone (30 mL) was stirred at room temperature for 20 hours. The lutidine•HCl salt was filtered. The filtrate was washed with hexane and water and dried to give 3.6 g of a white solid (N-methyl-N-phenyl-4-iodobenzenesulfonamide).

$^1$H NMR (CDCl$_3$): δ 7.80 (d, J=8.5 Hz, 2H), 7.23–7.35 (m, 5H), 7.09 (d, J=8.5 Hz, 2H), 3.18 (s, 3H). MS (EI) m/z 373 (M$^+$).

n-BuLi (1.6 M, 1.25 mL, 2 mmol) was added to the above product (373 mg, 1 mmol) in THF (10 mL) at −78° C. The mixture was stirred for 30 minutes, and this mixture was added dropwise to a solution of methyl trifluoroacetate (0.4 mL, 4 mmol) in THF (10 mL) at −78° C. The mixture was allowed to warm to room temperature slowly and stirred at room temperature for 1 hour. The mixture was treated with EtOAc, and it was washed with brine, dried, and concentrated. The residue was purified by silica column chromatography (eluted with 30% EtOAc/Hexane) to give 200 mg of product (N-methyl-N-phenyl-4-trifluoroacetylbenzenesulfonamide).

$^1$H NMR (CDCl$_3$): δ 8.14 (d, J=8.0 Hz, 2H), 7.72 (d, J=8.7 Hz, 2H), 7.32 (m, 3H), 7.09 (d, J=8.0 Hz, 2H), 3.24 (s, 3H). MS (ES) m/z 362.0 ([M+H$_3$O]$^+$)

Tetrabutylammonium fluoride (1.0 M in THF, 0.01 mL) was added to a solution of the above product (186 mg, 0.54 mmol) and trifluoromethyl trimethylsilane (0.5 M in THF, 1.62 mL, 0.81 mmol) in THF (7 mL) at 0° C. Then the mixture was stirred at room temperature overnight. EtoAc (50 mL) was added to the reaction mixture, and it was washed with brine, dried, and concentrated. The residue was purified by silica column chromatography (eluted with 30% EtOAc/Hexane) to give 90 mg of product (18.1).

$^1$H NMR (CDCl$_3$): δ 7.83 (d, J=8.4 Hz, 2H), 7.62 (d, J=7.0 Hz, 2H), 7.30 (m, 3H), 7.07 (d, J=8.4 Hz, 2H), 4.11 (bs, 1H), 3.20 (s, 3H). MS (ES) m/z 412.1 ([M−H]$^-$). Anal. Calcd. for C$_{16}$H$_{13}$F$_6$NO$_3$S: C, 46.49; H, 3.17; N, 3.39. Found: C, 46.71; H, 3.23; N, 3.36.

Similar procedures to the one described for the synthesis of compound 18.1 were followed to produce compounds 18.2 to 18.15.

18.2

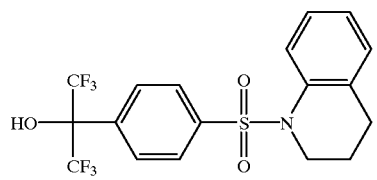

$^1$H-NMR (DMSO): δ 9.08 (s, 1H), 7.80 (m, 4H), 7.58 (m, 1H), 7.20 (m, 1H), 7.09 (m, 2H), 3.78 (t, J=5.96 Hz, 2H), 2.40 (m, 2H), 1.61 (m, 2H). MS (ES−): 438 (M−H, 42). Anal. Calc. for C$_{18}$H$_{15}$F$_6$NO$_3$S: C, 49.20; H, 3.43; N, 3.19; S, 7.30. Found: C, 49.42; H, 3.58; N, 5.15; S, 7.23.

18.3

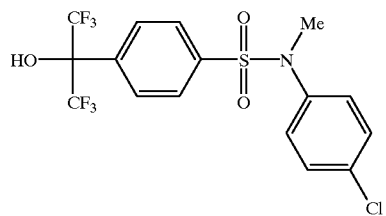

$^1$H-NMR (DMSO): δ 9.10 (s, 1H), 7.90 (d, J=8.52 Hz, 2H), 7.71 (m, 2H), 7.43 (m, 2H), 7.14 (m, 2H), 3.17 (s, 3H). MS (ES−): 446 (M−H, 100). Anal. Calc. for C$_{16}$H$_{12}$ClF$_6$NO$_3$S: C, 42.92; H, 2.70; N, 3.13; Cl, 7.92; S, 7.16. Found: C, 43.04; H, 2.69; N, 3.17; Cl, 8.01; S, 7.20.

18.4

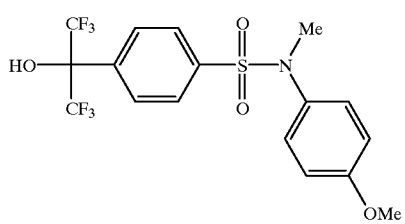

$^1$H-NMR (DMSO): δ 9.09 (s, 1H), 7.90 (d, J=8.44 Hz, 2H), 7.70 (m, 2H), 6.96 (m, 2H), 6.88 (m, 2H), 3.74 (s, 3H), 3.13 (s, 3H). MS (ES−): 442 (M−H, 62). Anal. Calc. for C$_{17}$H$_{15}$F$_6$NO$_4$S: C, 46.05; H, 3.41; N, 3.16; S, 7.23. Found: C, 46.15; H, 3.29; N, 3.17; S, 7.21.

18.5

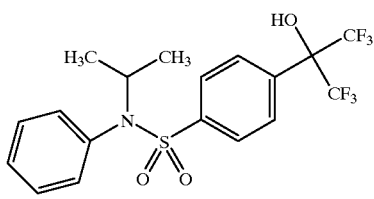

$^1$H-NMR (DMSO): δ 9.09 (s, 1H), 7.92 (s, 4H), 7.41 (m, 3H), 7.03 (m, 2H), 4.45 (m, 1H), 0.96 (d, J=6.76 Hz, 6H). MS (ES+): 442 (M+H, 100). Anal. Calc. for C$_{18}$H$_{17}$F$_6$NO$_3$S: C, 48.98; H, 3.88; N, 3.17; S, 7.26. Found: C, 49.07; H, 3.76; N, 3.16; S, 7.19.

18.6

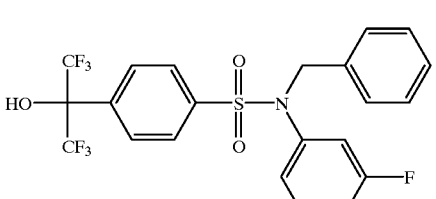

$^1$H-NMR (DMSO): δ 9.13 (s, 1H), 7.94 (d, J=8.44 Hz, 2H), 7.86 (d, J=8.72 Hz, 2H), 7.22 (m, 6H), 7.09 (m, 1H), 6.95 (m, 2H), 4.87 (s, 2H). MS (ES+): 508 (M+H, 75). Anal. Calc. for C₂₂H₁₆F₇NO₃S: C, 52.07; H, 3.18; N, 2.76; S, 6.32. Found: C, 52.14; H, 3.28; N, 2.77; S, 6.42.

18.7

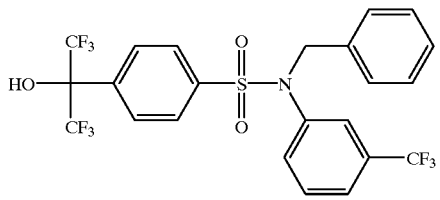

¹H-NMR (DMSO): δ 9.13 (s, 1H), 7.93 (d, J=8.40 Hz, 2H), 7.84 (m, 2H), 7.60 (d, J=8.00 Hz, 1H), 7.52 (t, J=8.08 Hz, 1H), 7.43 (d, J=8.36 Hz, 1H), 7.24 (m, 6H), 4.93 (s, 2H). MS (ES+): 558 (M+H, 35). Anal. Calc. for C₂₃H₁₆F₉NO₃S: C, 49.56; H, 2.89; N, 2.51; S, 5.75. Found: C, 49.74; H, 3.01; N, 2.55; S, 5.70.

18.8

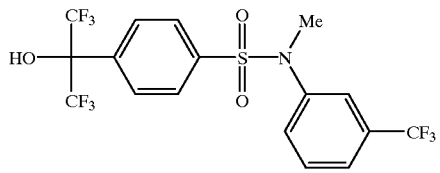

¹H-NMR (DMSO): δ 9.11 (s, 1H), 7.90 (d, J=8.44 Hz, 2H), 7.71 (m, 3H), 7.62 (m, 1H), 7.50 (m, 1H), 7.25 (3, 1H), 3.24 (s, 3H). MS (ES+): 482 (M+H, 100). Anal. Calc. for C₁₇H₁₂F₉NO₃S: C, 42.42; H, 2.51; N, 2.91; S, 6.66. Found: C, 42.69; H, 2.59; N, 3.01; S, 6.38.

18.9

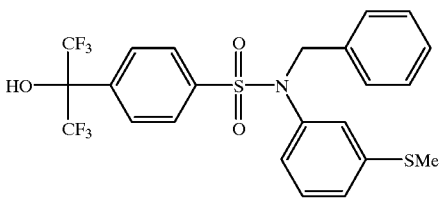

¹H-NMR (DMSO): δ 9.13 (s, 1H), 7.96 (m, 2H), 7.86 (m, 2H), 7.2 (m, 7H), 6.83 (m, 1H), 6.74 (m, 1H), 4.86 (s, 2H), 2.26 (s, 3H). MS (ES+). 536 (M+H, 100). Anal. Calc. for C₂₃H₁₉F₆NO₃S₂: C, 51.58; H, 3.58; N, 2.62; S, 11.98. Found: C, 52.30; H, 3.66; N, 2.71; S, 12.14.

18.10

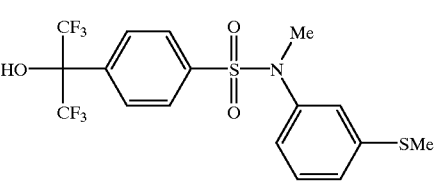

¹H-NMR (DMSO): δ 9.11 (s, 1H), 7.91 (d, J=8.32 Hz, 2H), 7.74 (m, 2H), 7.28 (m, 1H), 7.18 (d, J=7.12 Hz, 1H), 6.80 (d, J=7.76 Hz, 1H), 6.80 (d, J=1.48 Hz, 1H), 3.18 (s, 3H), 2.33 (s, 3H). MS (ES+): 460 (M+H, 87). Anal. Calc. for C₁₇H₁₅F₆NO₃S₂: C, 44.44; H, 3.29; N, 3.05; S, 13.96. Found: C, 45.24; H, 3.36; N, 3.10; S, 14.26.

18.11

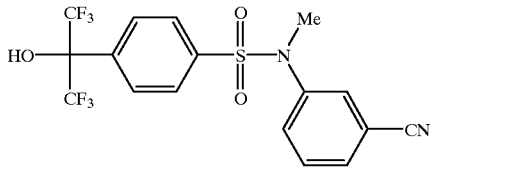

¹H-NMR (DMSO): δ 9.12 (s, 1H), 7.90 (d, J=8.44 Hz, 2H), 7.77 (d, J=7.28 Hz, 1H), 7.72 (d, J=8.56 Hz, 2H), 7.56 (m, 3H), 3.20 (s, 3H). MS (ES+): 439 (M+H, 60). Anal. Calc. for C₁₇H₁₂F₆N₂O₃S: C, 46.58; H, 2.76; N, 6.39; S, 7.32. Found: C, 46.58; H, 2.78; N, 6.32; S, 17.22.

18.12

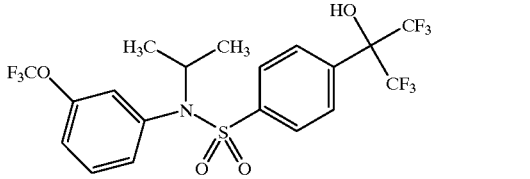

¹H-NMR (DMSO): δ 9.10 (s, 1H), 7.92 (s, 4H), 7.57 (m, 1H), 7.49 (m, 1H), 7.19 (m, 1H), 6.81 (s, 1H), 4.51 (m, 1H), 0.99 (d, J=6.80 Hz, 6H). MS (ES+): 526 (M+H, 80). Anal. Calc. for C₁₉H₁₆F₉NO₄S: C, 43.44; H, 3.07; N, 2.67; S, 6.10. Found: C, 44.52; H, 3.25; N, 2.75; S, 2.03.

18.13

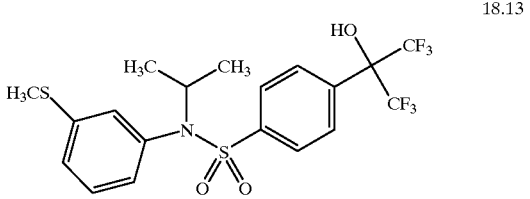

¹H-NMR (DMSO): δ 9.10 (s, 1H), 7.92 (s, 4H), 7.31 (m, 2H), 6.83 (d, J=7.60 Hz, 1H). 6.68 (s, 1H), 4.49 (m, 1H), 2.34 (s, 3H), 0.98 (d, J=6.68 Hz, 6H). MS (ES+): 488 (M+H, 100). Anal. Calc. for C₁₉H₁₉F₆NO₃S₂: C, 46.81; H, 3.93; N, 2.87; S, 13.16. Found: C, 47.17; H, 3.98; N, 2.89; S, 12.93.

18.14

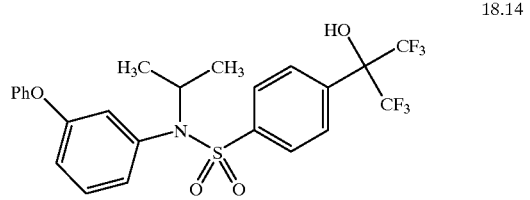

¹H-NMR (DMSO): δ 9.07 (s, 1H), 7.88 (s, 4H), 7.41 (m, 4H), 7.17 (m, 2H), 7.00 (m,2H), 6.83 (m, 1H), 6.51 (m, 1H), 4.43 (m, 1H), 0.93 (d, J=6.72 Hz, 6H). MS (ES+): 534 (M+H, 75). Anal. Calc. for C$_{24}$H$_{21}$F$_6$NO$_4$S: C, 54.03; H, 3.97; N, 2.63; S, 6.01. Found: C, 54.10; H, 3.93; N, 2.65; S, 6.05.

18.15

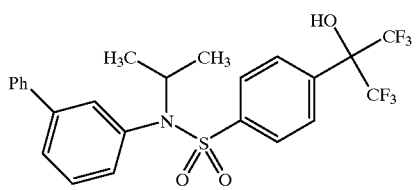

$^1$H-NMR (DMSO): δ 9.10 (s, 1H), 7.95 (s, 4H), 7.20 (m, 1H), 7.50 (m, 6H), 7.08 (m, 2H), 4.55 (m, 1H), 1.02(d, J=6.68 Hz, 6H). MS (ES+): 518 (M+H, 100). Anal. Calc. for C$_{24}$H$_{21}$F$_6$NO$_3$S: C, 55.70; H, 4.09; N, 2.71; S, 6.20. Found: C, 56.26; H, 4.27; N, 2.70; S, 6.02.

Additional examples prepared by procedures similar to those described bove:

18.16

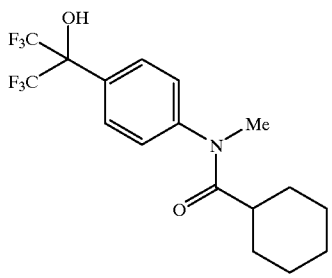

$^1$H-NMR (CDCl$_3$): δ 7.78 (d, J=8.3 Hz, 2H), 7.27 (d, J=8.3 Hz, 2H), 3.90 (bs,1 H), 3.26 (s, 3H), 2.20 (m, 1H), 1.40–1.70 (m, 8H), 1.15–1.35 (m, 2H). MS (ES-): 382 (M-H). Anal. Calcd. For C$_{17}$H$_{19}$F$_6$NO$_2$: C, 53.27; H, 5.00; N, 3.65. Found: C, 53.72; H, 5.21; N, 3.47.

18.17

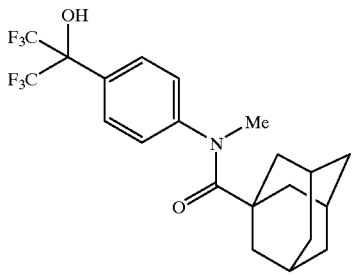

$^1$H-NMR (CDCl$_3$): δ 7.76 (d, J=8.4 Hz, 2H), 7.32 (s, J=8.4 Hz, 2H), 3.60 (s, 1H), 3.22 (s, 3H), 1.84 (s, 3H), 1.73 (s, 6H), 1.57 (d, J=12.4 Hz), 1.47 (d, J=12.4 Hz, 3H). MS (ES-): 434 (M-H). Anal. Calcd. For C$_{21}$H$_{23}$F$_6$NO$_2$: C, 57.93; H, 5.32; N, 3.22. Found: C, 58.07; H, 5.33; N, 3.18.

18.18

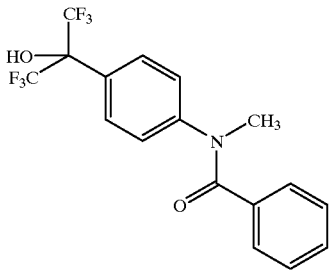

$^1$H-NMR (CD$_3$OD): δ 7.61 (d, J=8.4 Hz, 2H), 7.25 (m, 7H), 3.49 (s, H). MS (ES+): 378 (M+H), MS (ES-): 376 (M-H). Anal. Calcd. for C$_{17}$H$_{13}$F$_6$NO$_2$: C, 54.12; H, 3.47; N, 3.71. Found: C, 54.33; H, 3.41; N, 3.70.

18.19

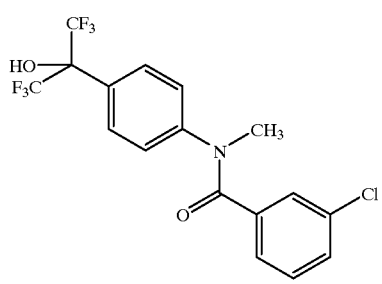

$^1$H-NMR (CD$_3$OD): δ 7.65 (d, J=8.4 Hz, 2H), 7.26 (d, J=8.7 Hz, 4H), 7.19 (s, 2H), 3.48 (s, 3H). MS (ES+): 412 (M+H), MS (ES-): 410 (M-H). Anal. Calcd. for C$_{17}$H$_{12}$ClF$_6$NO$_2$: C, 49.59; H, 2.94; N, 3.40. Found: C, 49.72; H, 2.96; N, 3.40.

18.20

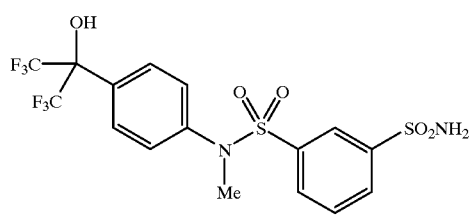

$^1$H-NMR (CDCl$_3$): δ 8.12 (d, J=9.1 Hz, 1H), 7.90 (s, 1H), 7.74 (d, J=7.0 Hz, 1H), 7.69 (d, J=6.8 Hz, 2H), 7.62 (dd, J=9.1, 7.0 Hz, 1H), 7.20 (d, J=6.8 Hz, 2H), 4.82)s, 2H), 3.80 (s, 1H), 3.22 (s, 3H). MS (ES-): 491 (M-H). Anal. Calcd. For C$_{16}$H$_{14}$F$_6$N2O$_5$S$_2$: C, 39.02; H, 2.87; N, 5.69; S, 13.02. Found: C, 39.52; H, 2.87; N, 5.44, S, 12.71.

18.21

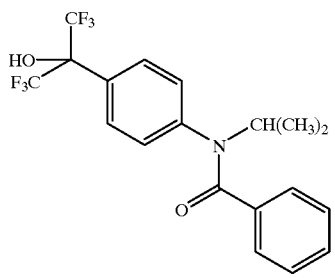

¹H-NMR (CDCl₃): δ 7.74 (d, J=7.9 Hz, 2H), 7.69 (d, J=8.4 Hz, 2H), 7.57 (t, J=7.6 Hz, 1H), 7.47 (t, J=7.6 Hz, 2H), 7.15 (d, J=8.5 Hz, 2H), 4.61 (m, 1H), 3.46 (s, 1H), 1.05(d, J=6.8 Hz, 6H). MS (ES+): 442 (M+H), MS (ES−): 440 (M−H). Anal. Calcd. for C₁₈H₁₇F₆NO₃S: C, 48.98; H, 3.88; N, 3.17; S, 7.26. Found: C, 49.08; H, 3.82; N, 3.09; S, 7.27.

18.22

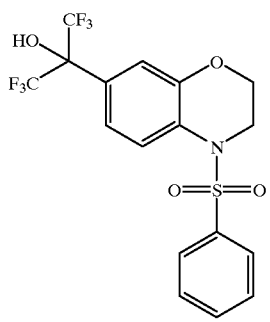

¹H-NMR (CD₃OD): δ 7.88 (d, J=8.9 Hz, 1H), 7.68 (d, J=8.2 Hz, 2H), 7.65 (t, J=7.6 Hz, 1H), 7.52 (t, J=7.8 Hz, 2H), 7.25 (d, J=8.6 Hz, 1H), 7.14 (s, 1H), 3.92 (t, J=4.6 Hz, 2H), 3.75 (t, J=4.6 Hz, 2H). MS (ES−): 440 (M−H). Anal. Calcd. for C₁₇H₁₃F₆NO₄S: C, 46.26; H, 2.97; N, 3.17; S, 7.27. Found: C, 46.39; H, 2.97; N, 3.18; S, 7.29.

18.23

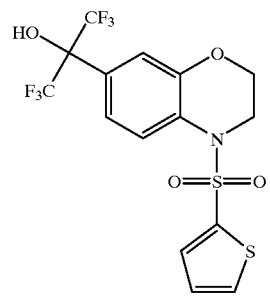

¹H-NMR (CDCl₃): δ 7.94 (d, J=9.0 Hz, 1H), 7.59 (d, J=5.0 Hz, 1H), 7.48 (d, J=5.1 Hz, 1H), 7.27 (d, J=9.5 Hz, 1H), 7.23 (s, 1H), 7.07 (t, J=5.0 Hz, 1H), 3.93 (t, J=5.0 Hz, 2H), 3.86 (t, J=4.9 Hz, 2H), 3.37 (s, 1H). MS (ES+): 448 (M+H), MS (ES−): 446 (M−H). Anal. Calcd. for C₁₅H₁₁F₆NO₄S₂: C, 40.27; H, 2.48; N, 3.13; S, 14.34. Found: C, 40.10; H, 2.51; N, 3.12; S, 14.32.

18.24

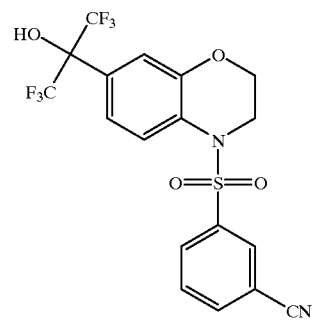

¹H-NMR (CDCl₃): δ 7.98 (s, 1H), 7.85 (m, 3H), 7.61 (t, J=7.9 Hz, 1H), 7.29 (d, J=8.8 Hz, 1H), 7.23 (s, 1H), 4.05 (s, 1H), 3.94 (t, J=3.6 Hz, 2H), 3.90 (t, J=3.6 Hz, 2H). MS (ES−): 465 (M−H). Anal. Calcd. for C₁₈H₁₂F₆N₂O₄S: C, 46.36; H, 2.59; N, 6.01; S, 6.88. Found: C, 46.76; H, 2.72; N, 5.76; S, 6.52.

18.25

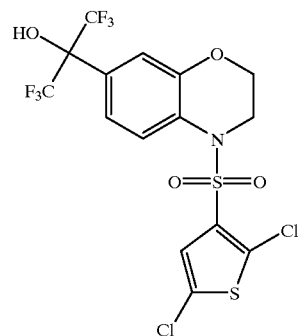

¹H-NMR (CDCl₃): δ 7.71 (d, J=8.8 Hz, 1H), 7.27 (s, 1H), 7.24 (d, J=8.8 Hz, 1H), 6.99 (s, 1H), 4.12(t, J=4.6 Hz, 2H), 3.99 (t, J=4.2 Hz, 2H) 3.33 (s, 1H). MS (ES−): 514 (M−H). Anal. Calcd. for C₁₅H₉Cl₂F₆NO₄S₂: C, 34.90; H, 1.76; N, 2.71; S, 12.42. Found: C, 35.00; H, 1.66; N, 2.71; S, 12.55.

18.26

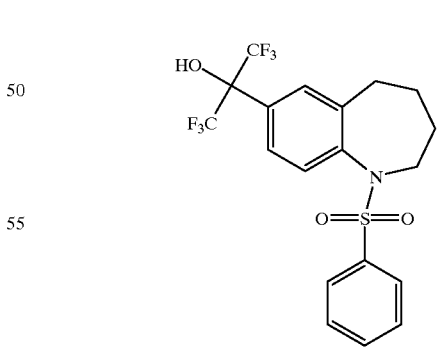

¹H-NMR (CDCl₃): δ 7.73 (d, J=7.9 Hz, 2H), 7.57 (t, J=7.9 Hz, 1H), 7.48 (m, 4H), 7.39 (d, J=8.8 Hz, 1H), 3.72 (bs, 2H), 3.44 (s, 1H), 2.42 (t, J=4.5 Hz, 2H), 1.80 (m, 2H), 1.57 (m, 2H). MS (ES+): 454 (M+H), MS (ES−): 452 (M−H). Anal. Calcd. for C₁₉H₁₇F₆NO₃S: C, 50.33; H, 3.78; N, 3.09; S, 7.07. Found: C, 50.06; H, 3.69; N, 3.06; S, 7.22.

18.27

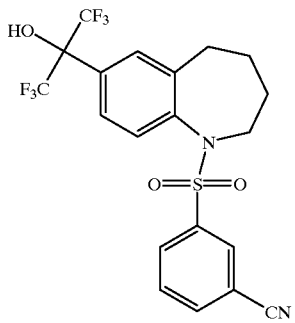

¹H-NMR (CDCl₃): δ 8.02 (s, 1H), 7.91 (d, J=8.0 Hz, 1H), 7.84 (d, J=7.7 Hz, 1H), 7.61 (t, J=7.9 Hz, 1H), 7.539 (d, J=8.5 Hz, 1H), 7.51 (s, 1H) 7.31 (d, J=8.2 Hz, 1H), 4.06 (s, 1H), 3.74 (bs, 2H), 2.42 (t, J=5.0 Hz, 2H), 1.81 (q, J=5.7 Hz, 2H), 1.60 (bs. 2H). MS (ES−): 477 (M−H). Anal. Calcd. for C₂₀H₁₆F₆N₂O₃S: C, 50.21; H, 3.37; N, 5.86; S, 6.70. Found: C, 51.28; H, 3.75; N, 5.50; S, 6.39.

18.28

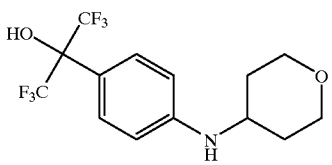

Reductive amination:

A mixture of 4-(hexafluoro-2-hydroxyisopropyl)aniline (1.0 g, 0.386 mol) and tetrahydro-4H-pyran-4-one (0.433 g, 0.433 mol, available from Aldrich Chemical Company) in methanol was stirred overnight. To this solution was added acetic acid (0.25 mL) followed by sodium cyanoborohydride (0.365 g, 0.006 mol). Stirring was continued for an additional 3 hr, at which time TLC analysis revealed completion of reaction. The reaction mixture was concentrated under vacuum. The residue was dissolved in ethyl acetate, washed with brine, dried, and concentrated. Purification of the crude product by flash chromatography on silica gel eluted with 4:1 to 2:1 hexane/EtOAc produced pure product (18.28) 1.06 g, 80.0%.

¹H-NMR (CDCl₃): δ 7.48 (d, J=8.0 Hz, 2H), 6.61 (d, J=8.0 Hz, 2H), 4.00 (m, 1H), 3.83 (s, 1H), 3.50 (t, J=6.5 Hz, 4H), 3.40 (s, 1H), 1.52 (m, 4H). MS (ES+): 344 (M+H).

18.29

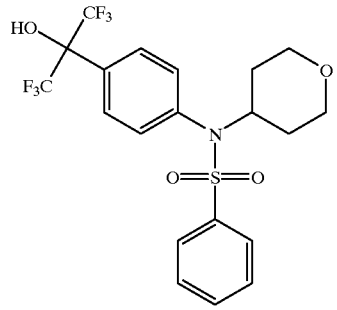

Starting from compound 18.28 and following the standard procedure for sulfonylation, compound 18.29 was obtained.

¹H-NMR (CDCl₃): δ 7.72 (d, J=7.7 Hz, 2H), 7.66 (d, J=8.1 Hz, 2H), 7.57 (t, J=7.3 Hz, 1H), 7.47 (t, J=7.7 Hz, 2H), 7.09 (d, J=8.4 Hz, 1H), 3.72 (m, 1H), 4.19 (s, 1H), 3.91 (dd, J=11.5, 4 Hz, 2H), 3.45 (t, J=11.8 Hz, 2H), 1.72 (d, J=12 Hz, 2H), 1.44 (q, J=12 Hz, 2H). MS (ES+): 484 (M+H), MS (ES−): 482 (M−H). Anal. Calcd. for C₂₀H₁₉F₆NO₄S: C, 49.69; H, 3.96; N, 2.90; S, 6.63. Found: C, 49.66; H, 3.84; N, 2.89; S, 6.52.

18.30

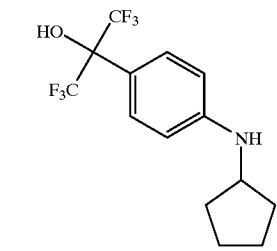

Substituting cyclopentanone for tetrahydro-4H-pyran-4-one, compound 18.30 was prepared by a procedure similar to the synthesis of compound 18.28.

¹H-NMR (CDCl₃): δ 7.45 (d, J=8.0 Hz, 2H), 6.60 (d, J=8.0 Hz, 2H), 3.88 (s, 1H), 3.80 (s, 1H), 2.05 (m, 4H), 1.65 (m, 4H). MS (ES+): 260 (M+H).

18.31

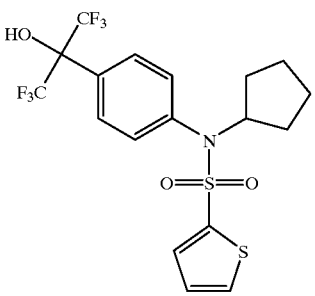

¹H-NMR (CDCl₃): δ 7.70 (d, J=8.5 Hz, 2H), 7.59 (d, J=4.9 Hz, 1H), 7.43 (d, J=5.0 Hz, 1H), 7.19(d, 8.4 Hz, 2H), 7.06 (t, J=4.0 Hz, 1H), 4.52 (m, 1H), 3.45 (s, 1H), 1.89(t, J=5.2 Hz, 2H), 1.48 (m, 4H), 1.32 (m, 2H). MS (ES−): 472 (M−H). Anal. Calcd. for C₁₈H₁₇F₆NO₃S₂: C, 45.66; H, 3.62; N, 2.96; S, 13.55. Found: C, 45.77; H, 3.69; N, 2.97; S, 13.69.

18.32

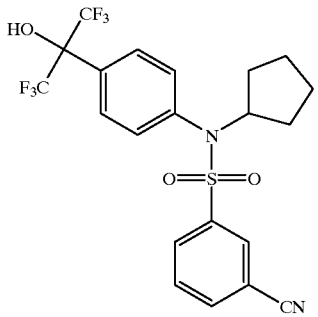

18.32

¹H-NMR (CDCl₃): δ 8.01 (s, 1H), 7.89 (d, J=8.0 Hz, 21H), 7.85 (d, J=7.8 Hz, 1H), 7.71 (d, J=8.4 Hz, 2H), 7.61(t, J=7.9 Hz, 1H), 7.10 (d, J=8.7 Hz, 2H), 4.53 (m, 1H), 3.53 (s, 1H), 1.86(m, 2H), 1.51 (m, 4H), 1.30 (m, 2H). MS (ES-): 491 (M-H). Anal. Calcd. for C₂₁H₁₈F₆N₂O₃S: C, 51.22; H, 3.68; N, 5.69; S, 6.51. Found: C, 51.29; H, 3.56; N, 5.63; S, 6.49.

18.33

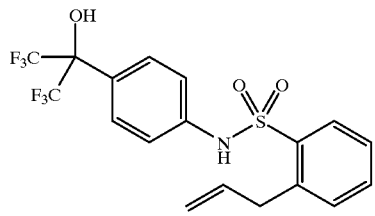

18.33

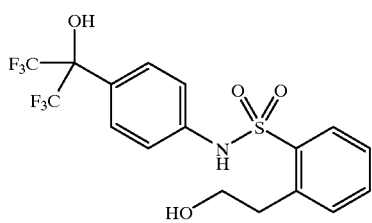

18.34

Compound 18.33 was prepared from the corresponding sulfonyl chloride following the standard sulfonylation procedure described above. Compound 18.33 (150 mg, 0.342 mmol) was treated under Lemieux-Johnson oxidative cleavage conditions (OsO₄, 0.0342 mmol; NaIO₄, 250 mg, 1.27 mmol; in 2:1 acetone/H₂O) to give the corresponding aldehyde. The aldehyde was then reduced with NaBH₄ in methanol at 0° C. to give compound 18.34, 50 mg, 30%.

¹H-NMR (CDCl₃): δ 7.82 (d, J 7.2 Hz, 1H), 7.80 (bs, 1H), 7.55 (d, J=8.4 Hz, 2H), 7.51 (t, J=7.2 Hz, 1H), 7.37 (d, J=7.6 Hz, 1H), 7.25 (t, J=7.6 Hz, 1H), 7.13 (d, J=8.4 Hz, 2H), 4.04 (t, J=6.1 Hz, 2H), 3.57 (s, 1H), 3.43 (t, J=6.1 Hz, 2H), 2.15 (bs, 1H). MS (ES-): 442 (M-H).

18.35

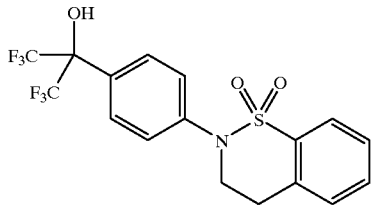

18.35

A sample of compound 18.34 (22 mg, 0.049 mmol) was dissolved in anhydrous THF (2 mL). To it was added triphenylphosphine (32.5 mg, 0.124 mmol) followed by diethyl azodicarboxylate (15.6 mL, 0.10 mmol) at 0° C. Stirring was continued for an additional 2 hrs. The reaction mixture was diluted with ethyl acetate, washed with aqueous NaHCO₃ solution, dried over MgSO₄, filtered and concentrated. Crude product was purified by flash chromatography on silica gel, eluted with 1:1 hexane/EtOAc to give compound 18.35, 18.2 mg, 86.2%.

¹H-NMR (CDCl₃): δ 7.89 (d, J=7.6 Hz, 1H), 7.69 (d, J=8.4 Hz, 2H), 7.532 (t, J=7.6 Hz, 1H), 7.45 (d, J=7.6 Hz, 1H), 7.37 (d, J=8.4 Hz, 2H), 7.26 (d, J=7.6 Hz, 1H), 7.37 (d, J=8.4 Hz, 2H), 7.26 (d, J=7.6 Hz, 1H), 4.27 (t, J=6.4 Hz, 2H), 3.58 (s, 1H), 3.19 (t, J=6.4 Hz, 2H). MS (ES-): 424 (M-H).

18.36

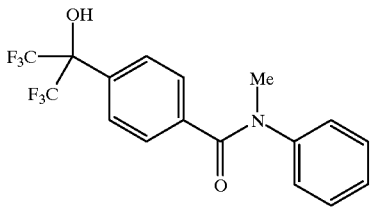

18.36

4-(Hexafluoro-2-hydroxyisopropyl)benzoic acid (100 mg, 0.35 mmol, available from Lancaster) was treated with oxalyl chloride (2.0M solution in dichloromethane, 0.35 mL, 0.70 mmol) in dichloromethane (2 mL) at ambient temperature for two hours. The reaction mixture was evaporated to dryness, redissolved in dichloromethane (2 mL), and was added to a stirred mixture of N-methylaniline (56 mg, 0.53 mmol) and diisopropylethylamine (0.12 mL, 0.70 mmol) in dichloromethane (2 mL). Upon completion of reaction, the mixture was diluted with dichloromethane, washed with 0.5 N HCl, brine, and NaHCO₃ solution. The organic phase was dried over MgSO₄, filtered and concentrated. The crude product was purified by flash chromatography on silica gel to give compound 18.36, 118 mg, 90.1%.

¹H-NMR (CDCl₃): δ 7.50 (d, J=8.0 Hz, 2H), 7.30 (d, J=7.0 Hz, 2H), 7.20 (t, J=7.0 Hz, 2H), 7.14 (t, J=7.0 Hz, 1H), 7.01 (d, J=8.0 Hz, 2H), 3.80 (s, 1H), 3.50 (s, 3H). MS (ES-): 376 (M-H).

Example 19

LXRα agonist activity can be characterized in a cell-based assay or a peptide-sensor assay. The same assays can be utilized to characterize LXRα antagonist activity, by evaluating the ability of a compound to block the effects of an LXRα agonist, such as 24,25-epoxycholesterol.

Briefly, for the cell-based assay, a DNA-binding domain of the nonreceptor transcription factor GAL4 was fused to the putative ligand-binding domain of LXRα. The resultant construct was introduced into 293 cells, together with UAS-containing luciferase reporter construct. The transfected cells were then treated with chemical libraries and luciferase activity was measured. Individual compounds were evaluated relative to a control (no addition of compound) and the $EC_{50}$ was determined as the concentration necessary to produce 50% of the maximal luciferase activity.

The peptide sensor LXR assay is an in vitro assay and was conducted as generally described in co-pending applications Ser. Nos. 08/975,614 (filed Nov. 21, 1997) and 09/163,713 (filed Sep. 30, 1998). Exemplary of the activity observed for the compounds provided herein was exhibited by compound 2 ($EC_{50}$ in each of the assays was less than 2 micromolar).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition for modulation of LXR function in a cell, said composition comprising a pharmaceutically acceptable excipient and a compound having the formula:

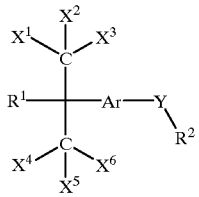

or a pharmaceutically acceptable salt thereof, wherein
Ar is an aryl group;
$R^1$ is a member selected from the group consisting of —OH, —$CO_2$H, —O—($C_1$–$C_7$)alkyl, —OC(O)—($C_1$–$C_7$)alkyl, —O—($C_1$–$C_7$)heteroalkyl, —OC(O)—($C_1$–$C_7$)heteroalkyl, —$NH_2$, —NH($C_1$–$C_7$)alkyl, —N(($C_1$–$C_7$)alkyl)$_2$ and —NH—S(O)$_2$—($C_1$–$C_5$)alkyl;
$R^2$ is a member selected from the group consisting of ($C_1$–$C_7$)alkyl, ($C_1$–$C_7$)heteroalkyl, aryl and aryl($C_1$–$C_7$)alkyl;
$X^1$, $X^2$, $X^3$, $X^4$, $X^5$ and $X^6$ are each independently a member selected from the group consisting of H, ($C_1$–$C_5$)alkyl, ($C_1$–$C_5$)heteroalkyl, F and Cl, with the proviso that no more than three of $X^1$ through $X^6$ are H, ($C_1$–$C_5$)alkyl or ($C_1$–$C_7$)heteroalkyl; and
Y is a divalent linking group selected from the group consisting of —N($R^{12}$)S(O)$_m$—, —N($R^{12}$)S(O)$_m$N($R^{13}$)—, —N($R^{12}$)C(O)—, —N($R^{12}$)C(O)N($R^{13}$)—, —N($R^{12}$)C(S)— and —N($R^{12}$)C(O)O—;
wherein $R^{12}$ and $R^{13}$ are each independently selected from the group consisting of H, ($C_1$–$C_7$)alkyl, ($C_1$–$C_7$)heteroalkyl, aryl and aryl($C_1$–$C_7$)alkyl, and optionally when Y is —N($R^{12}$)S(O)$_m$— or —N($R^{12}$)S(O)$_m$N($R^{13}$)—, $R^{12}$ forms a five- or six-membered ring fused to Ar or to $R^2$ through covalent attachment to Ar or to $R^2$, respectively; and the subscript m is an integer of from 1 to 2;
with the proviso that when $R^1$ is OH, and —Y—$R^2$ is —N($R^{12}$)S(O)$_m$—$R^2$ or —N($R^{12}$)C(O)N($R^{13}$)—$R^2$ and is attached to a position para to the quaternary carbon attached to Ar, and when $R^2$ is phenyl, benzyl or benzoyl, then i) at least one of $R^{12}$ or $R^{13}$ is other than hydrogen and contains an electron-withdrawing substituent, or ii) $R^2$ is substituted with a moiety other than amino, acetamido, di($C_1$–$C_7$)alkylamino, ($C_1$–$C_7$)alkylamino, halogen, hydroxy, nitro, or ($C_1$–$C_7$)alkyl, or iii) the benzene ring portion of $R^2$ is substituted with at least three independently selected groups in addition to the Y group or point of attachment to Y.

2. A composition in accordance with claim 1, wherein Ar represents a substituted or unsubstituted ring selected from the group consisting of benzene, naphthalene, pyridine, quinoline, isoquinoline, pyrrole, furan and thiophene.

3. A composition in accordance with claim 1, wherein Ar represents a benzene ring.

4. A composition in accordance with claim 1, wherein $R^1$ is a member selected from the group consisting of —OH, —$CO_2$H, —$NH_2$, —NH($C_1$–$C_7$)alkyl, —N(($C_1$–$C_7$)alkyl)$_2$ and —NH—S(O)$_2$$CH_3$.

5. A composition in accordance with claim 1, wherein $R^2$ is aryl.

6. A composition in accordance with claim 1, wherein $R^2$ is phenyl, said phenyl group being substituted with at least one substituent at the ortho or meta position relative to the point of attachment to Y.

7. A composition in accordance with claim 1, wherein no more than one of $X^1$ through $X^6$ is hydrogen or ($C_1$–$C_5$) alkyl.

8. A composition in accordance with claim 1, selected from the group consisting of

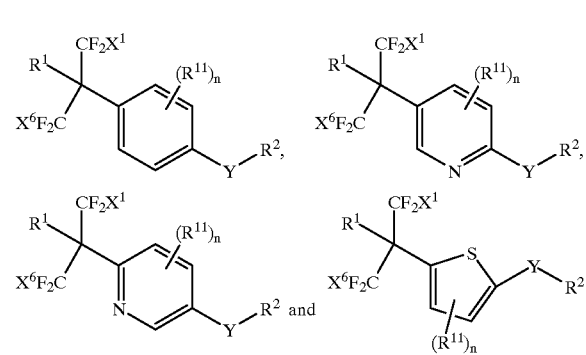

wherein the subscript n represents an integer of from 0 to 4; and
each $R^{11}$ is independently selected from the group consisting of —OH, —$NH_2$, lower alkyl, lower alkoxy, —NR'R", —SR', —halogen, —SiR'R"R'", —OC(O)R', —$CO_2$R', —CONR'R", —OC(O)NR'R", —NR"C(O)R', —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$.

9. A composition in accordance with claim 1, said compound having a formula selected from the group consisting of

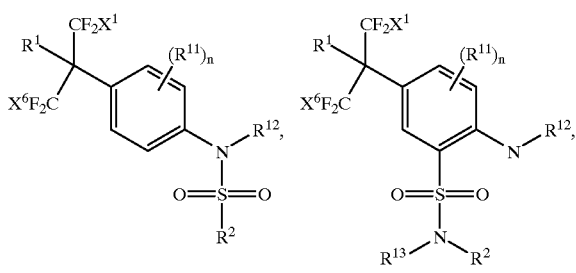

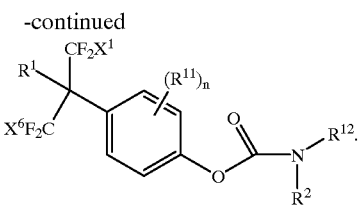

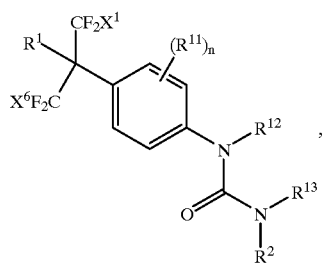

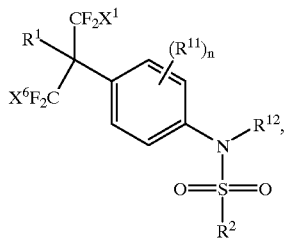

10. A composition in accordance with claim 9, said compound having a formula selected from the group consisting of

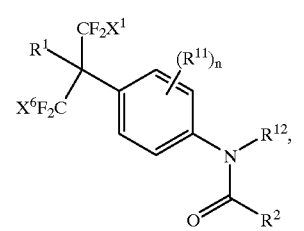

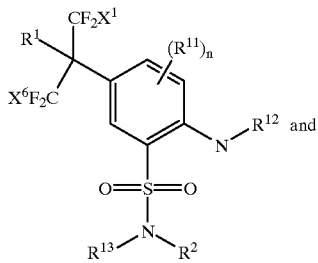

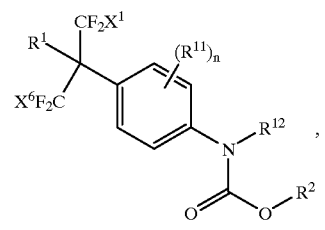

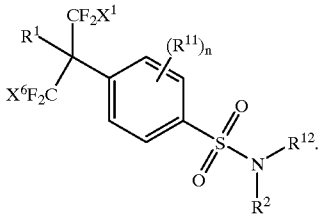

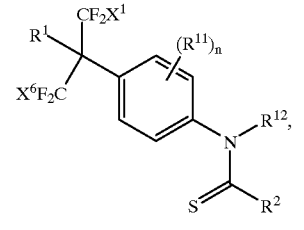

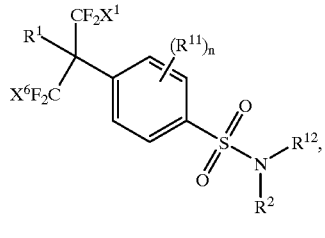

11. A composition in accordance with claim 1, wherein $X^1$, $X^2$, $X^3$, $X^4$, $X^5$ and $X^6$ are each F.

12. A composition in accordance with claim 1, wherein $X^1$, $X^2$, $X^3$, $X^4$, $X^5$ and $X^6$ are each F, $R^1$ is a member selected from the group consisting of —OH, —NH$_2$, —CO$_2$H, —O—(C$_1$-C$_7$)alkyl, and —OC(O)—(C$_1$-C$_7$) alkyl, Y is a member selected from the group consisting of —N(R$^{12}$)S(O)$_m$—, —N(R$^{12}$)C(O)— and —N(R$^{12}$)C(O)N (R$^{13}$)—, and $R^2$ is aryl.

13. A composition in accordance with claim 10, said compound having a formula selected from the group consisting of:

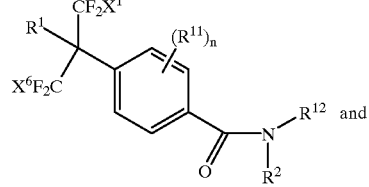

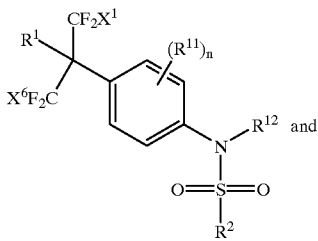

-continued

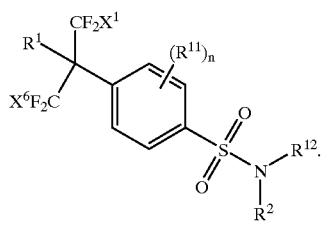

wherein R¹ is a member selected from the group consisting of —OH and —NH$_2$; X¹ and X$^6$ are each independently hydrogen or fluorine, R$^{12}$ is fluoro(C$_1$–C$_4$)alkyl; and R² is aryl.

14. A composition in accordance with claim 10, said compound having a formula selected from the group consisting of:

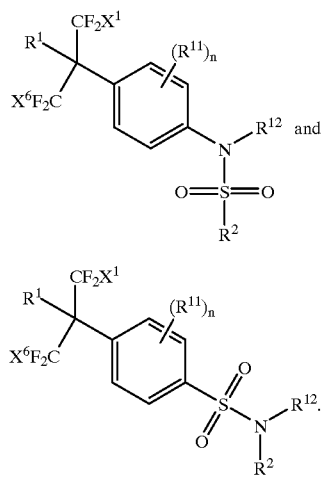

wherein R¹ is a member selected from the group consisting of —OH and —NH$_2$; X¹ and X$^6$ are each independently hydrogen or fluorine, R$^{12}$ is H, (C$_1$–C$_4$)alkyl or (C$_2$–C$_4$)heteroalkyl; and R² is substituted or unsubstituted thienyl.

15. A composition in accordance with claim 10, said compound having a formula selected from the group consisting of:

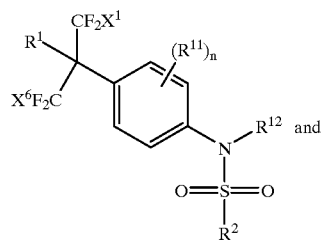

-continued

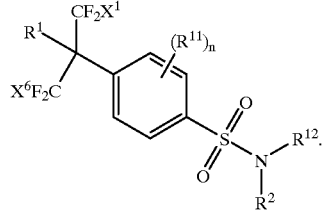

wherein R¹ is a member selected from the group consisting of —OH and —NH$_2$; X¹ and X$^6$ are each independently H or F; R$^{12}$ is (C$_1$–C$_4$)alkyl; and R² is phenyl substituted with at least one member selected from the group consisting of halogen —CN, —CF$_3$, —O—(C$_1$–C$_4$)alkyl, —C(O)—(C$_1$–C$_4$)alkyl, —C(O)—O (C$_1$–C$_4$)alkyl, —C(O)—NH(C$_1$–C$_4$)alkyl and —C(O) N((C$_1$–C$_4$)alkyl)$_2$.

16. A composition in accordance with claim 15, wherein R¹ is —OH; X¹ and X$^6$ are each fluorine; and R² is phenyl substituted with at least one member selected from the group consisting of —CN, —CF$_3$ and —O—(C$_1$–C$_4$)alkyl.

17. A composition in accordance with claim 1, wherein said compound is selected from the group consisting of:

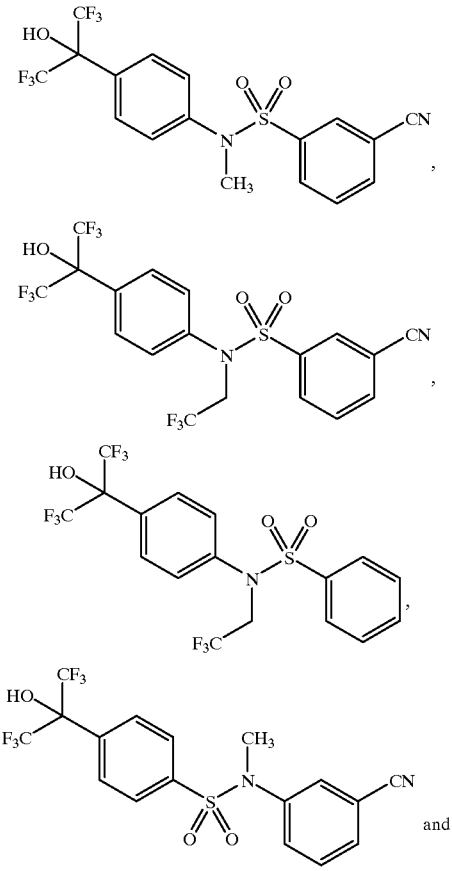

-continued

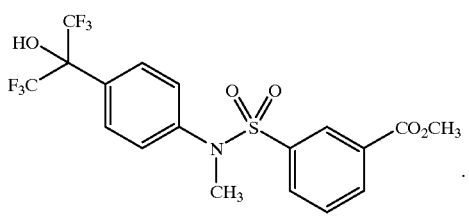

18. A composition in accordance with claim 1, wherein said compound is selected from the group consisting of:

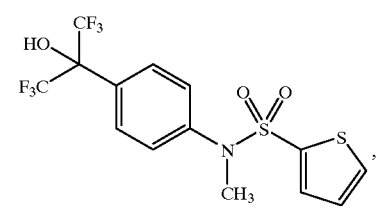

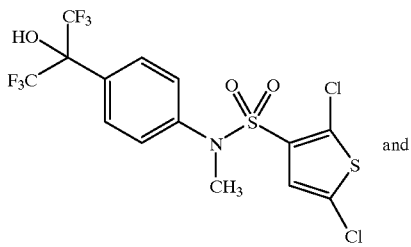

19. A composition in accordance with claim 1, wherein said compound is selected from the group consisting of:

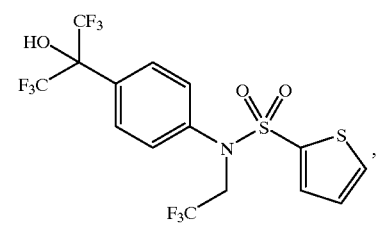

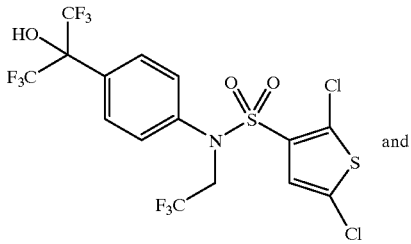

-continued

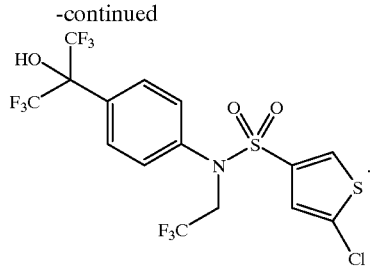

20. A compound having the formula:

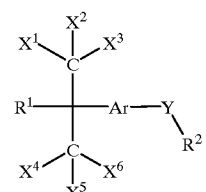

or a pharmaceutically acceptable salt thereof, wherein
Ar is an aryl group;
$R^1$ is a member selected from the group consisting of —OH, —$CO_2$H, —O—($C_1$-$C_7$)alkyl, —OC(O)—($C_1$-$C_7$)alkyl, —O—($C_1$-$C_7$)heteroalkyl, —OC(O)—($C_1$-$C_7$)heteroalkyl, —$NH_2$, —NH($C_1$-$C_7$)alkyl, —N(($C_1$-$C_7$)alkyl)$_2$ and —NH—S(O)$_2$—($C_1$-$C_5$)alkyl;
$R^2$ is a member selected from the group consisting of ($C_1$-$C_7$)alkyl, ($C_1$-$C_7$)heteroalkyl, aryl and aryl($C_1$-$C_7$)alkyl;
$X^1$, $X^2$, $X^3$, $X^4$, $X^5$ and $X^6$ are each independently a member selected from the group consisting of H, ($C_1$-$C_5$)alkyl, ($C_1$-$C_5$)heteroalkyl, F and Cl, with the proviso that no more than three of $X^1$ through $X^6$ are H, ($C_1$-$C_5$)alkyl or ($C_1$-$C_5$)heteroalkyl; and
Y is a divalent linking group selected from the group consisting of —N($R^{12}$)S(O)$_m$—, N($R^{12}$)S(O)$_m$N($R^{13}$)—, —N($R^{12}$)C(O)—, —N($R^{12}$)C(O)N($R^{13}$)—, —N($R^{12}$)C(S)— and —N($R^{12}$)C(O)O—;
wherein $R^{12}$ and $R^{13}$ are each independently selected from the group consisting of H, ($C_1$-$C_7$)alkyl, ($C_1$-$C_7$)heteroalkyl, aryl and aryl($C_1$-$C_7$)alkyl, and optionally when Y is —N($R^{12}$)S(O)$_m$— or N($R^{12}$)S(O)$_m$N($R^{13}$)—, $R^{12}$ forms a five- or six-membered ring fused to Ar or to $R^2$ through covalent attachment to Ar or to $R^2$, respectively; and the subscript m is an integer of from 1 to 2;
with the proviso that when $R^1$ is OH, and —Y—$R^2$ is —N($R^{12}$)S(O)$_m$$R^2$ or —N($R^{12}$)C(O)N($R^{13}$)—$R^2$ and is attached to a position para to the quaternary carbon attached to Ar, and when $R^2$ is phenyl, benzyl or benzoyl, then i) at least one of $R^{12}$ or $R^{13}$ is other than hydrogen and contains an electron-withdrawing substituent, or ii) $R^2$ is substituted with a moiety other than amino, acetamido, di($C_1$-$C_7$)alkylamino, ($C_1$-$C_7$)alkylamino, halogen, hydroxy, nitro, or ($C_1$-$C_7$)alkyl, or iii) the benzene ring portion of $R^2$ is trisubstituted in addition to the attached Y group.

21. A compound in accordance with claim 20, wherein Ar represents a substituted or unsubstituted ring selected from the group consisting of benzene, naphthalene, pyridine, quinoline, isoquinoline, pyrrole, furan and thiophene.

22. A compound in accordance with claim 20, wherein Ar represents a benzene ring.

23. A compound in accordance with claim 20, wherein $R^1$ is a member selected from the group consisting of —OH, —$CO_2H$, —$NH_2$, —NH($C_1$–$C_7$)alkyl, —N(($C_1$–$C_7$)alkyl)$_2$ and —NH—S(O)$_2$CH$_3$.

24. A compound in accordance with claim 20, wherein $R^2$ is aryl.

25. A compound in accordance with claim 20, wherein $R^2$ is phenyl, said phenyl group being substituted with at least one substituent at the ortho or meta position relative to the point of attachment to Y.

26. A compound in accordance with claim 20, wherein no more than one of $X^1$ through $X^6$ is hydrogen or ($C_1$–$C_5$) alkyl.

27. A compound in accordance with claim 20, selected from the group consisting of

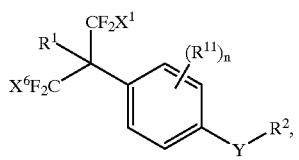

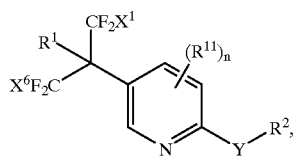

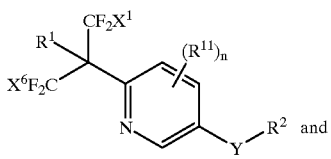 and

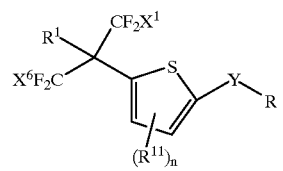

wherein the subscript n represents an integer of from 0 to 4; and each $R^{11}$ is independently selected from the group consisting of —OH, —$NH_2$, lower alkyl, lower alkoxy, —NR'R", —SR', -halogen, —SiR'R"R'", —OC(O)R', —$CO_2$R', —CONR'R", —OC(O)NR'R", —NR"C(O)R', —NR"C(O)NR'R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$.

wherein R', R" and R'" are each independently selected from the group consisting of ($C_1$–$C_5$)alkyl and ($C_1$–$C_5$) haloalkyl.

28. A compound in accordance with claim 27, said compound having a formula selected from the group consisting of:

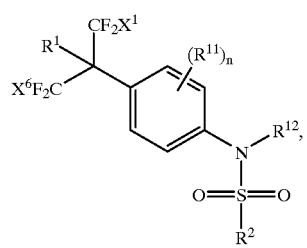

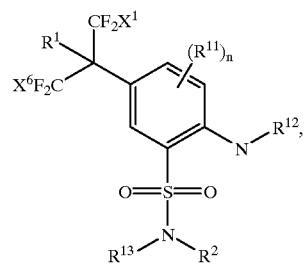

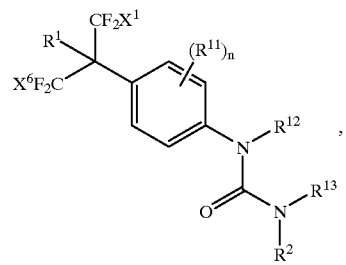

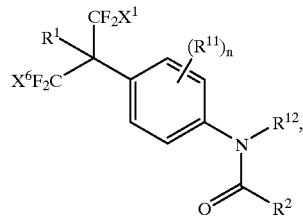

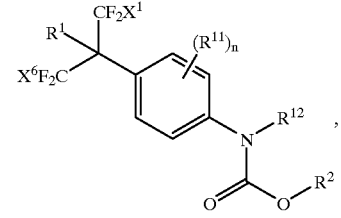

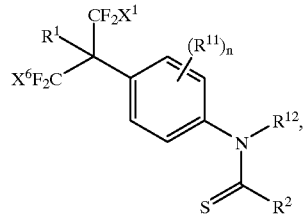

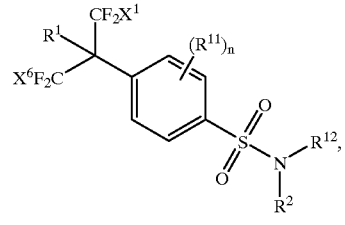

-continued

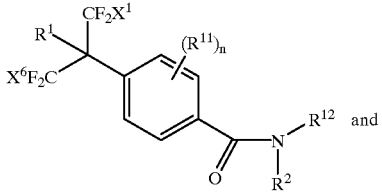

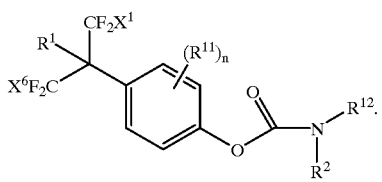

29. A compound in accordance with claim 28, said compound having a formula selected from the group consisting of

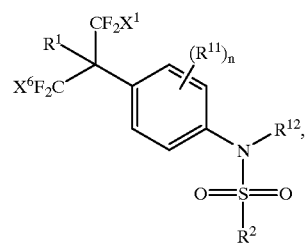

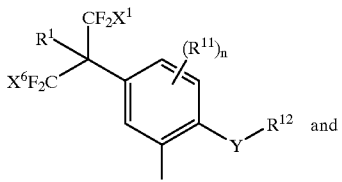

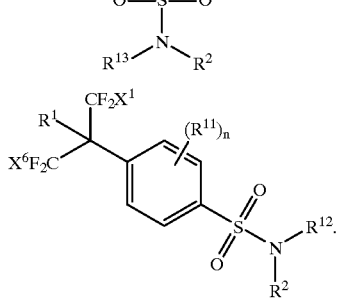

30. A compound in accordance with claim 20, wherein $X^1$, $X^2$, $X^3$, $X^4$, $X^5$ and $X^6$ are each F.

31. A compound in accordance with claim 20, wherein $X^1$, $X^2$, $X^3$, $X^4$, $X^5$ and $X^6$ are each F; $R^1$ is a member selected from the group consisting of —OH, —CO$_2$H, —NH$_2$, —O—(C$_1$–C$_7$)alkyl, and —OC(O)—(C$_1$–C$_7$)alkyl; Y is a member selected from the group consisting of —N(R$^{12}$)S(O)$_m$—, —N(R$^{12}$)C(O)— and —N(R$^{12}$)C(O)N(R$^{13}$)—; and $R^2$ is aryl.

32. A compound in accordance with claim 29, said compound having the formula:

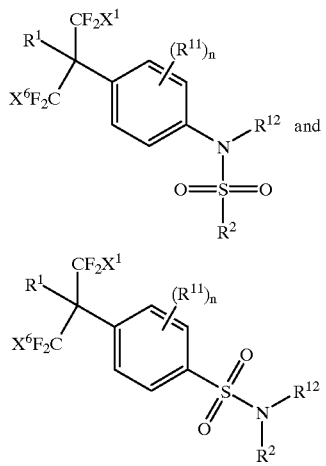

wherein $R^1$ is a member selected from the group consisting of —OH and —NH$_2$; $X^1$ and $X^6$ are each independently hydrogen or fluorine, $R^{12}$ is fluoro(C$_1$–C$_4$)alkyl; and $R^2$ is aryl.

33. A compound in accordance with claim 29, said compound having the formiula:

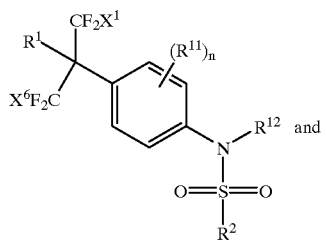

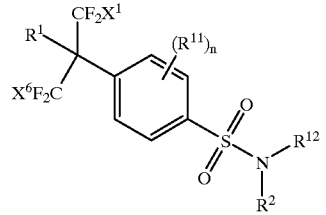

wherein $R^1$ is a member selected from the group consisting of —OH and —NH$_2$; $X^1$ and $X^6$ are each independently H or F; $R^{12}$ is H, (C$_1$–C$_4$)alkyl or (C$_2$–C$_4$) heteroalkyl; and $R^2$ is substituted or unsubstituted thienyl.

34. A compound in accordance with claim 29, said compound having the formula:

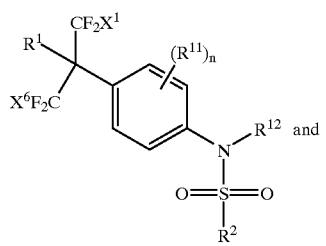

-continued

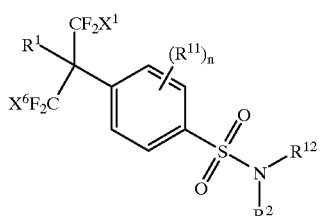

wherein $R^1$ is a member selected from the group consisting of —OH and —$NH_2$; $X^1$ and $X^6$ are each independently hydrogen or fluorine, $R^{12}$ is ($C_1$–$C_4$)alkyl; and $R^2$ is phenyl substituted with at least one member selected from the group consisting of halogen, —CN, —$CF_3$, —O—($C_1$–$C_4$)alkyl, —C(O)—($C_1$–$C_4$)alkyl, —C(O)—O($C_1$–$C_4$)alkyl, —C(O)—NH($C_1$–$C_4$)alkyl and —C(O)N(($C_1$–$C_4$)alkyl)$_2$.

35. A compound in accordance with claim 34, wherein $R^1$ is —OH; $X^1$ and $X^6$ are each fluorine; and $R^2$ is phenyl substituted with at least one member selected from the group consisting of —CN, —$CF_3$ and —O—($C_1$–$C_4$)alkyl.

36. A compound in accordance with claim 20, wherein said compound is selected from the group consisting of:

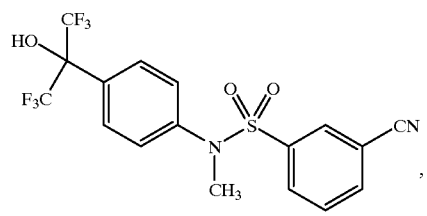

,

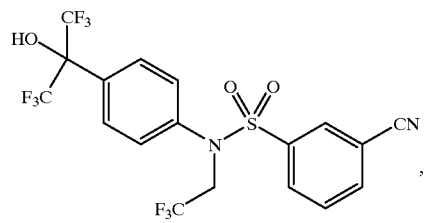

,

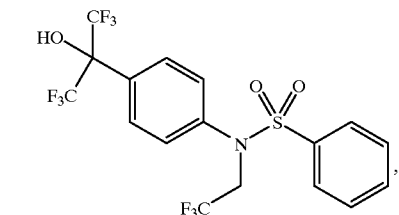

,

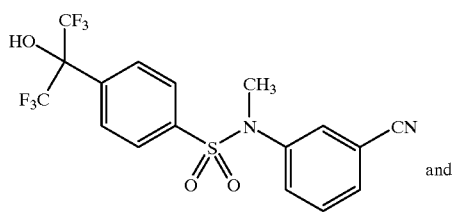

and

37. A compound in accordance with claim 20, wherein said compound is selected from the group consisting of:

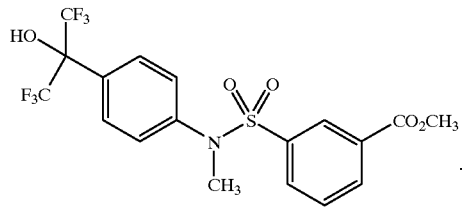

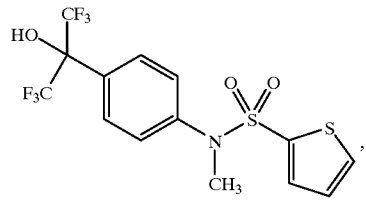

,

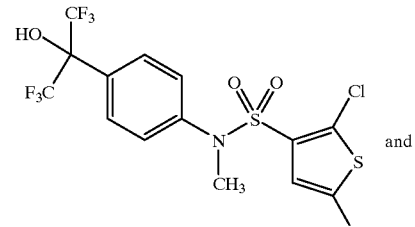

and

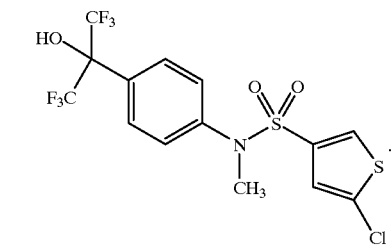

.

38. A compound in accordance with claim 20, wherein said compound is selected from the group consisting of:

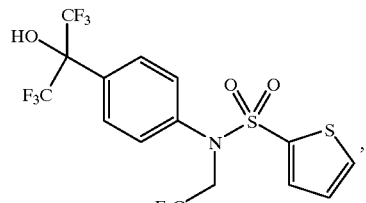

,

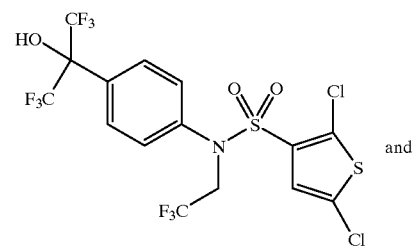

and

-continued

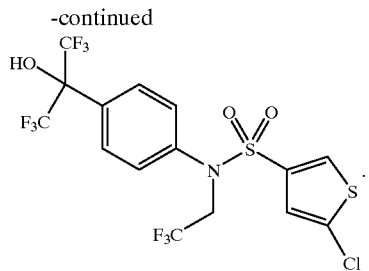

39. A method of modulating LXR function in a cell, tissue or animal, said method comprising contacting said cell, tissue or animal with a pharmaceutical composition comprising an LXR-modulating amount of a compound of the formula:

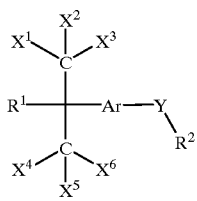

or a pharmaceutically acceptable salt thereof, wherein
Ar is an aryl group;
$R^1$ is a member selected from the group consisting of —OH, —$CO_2$H, —O—($C_1$–$C_7$)alkyl, —OC(O)—($C_1$–$C_7$)alkyl, —O—($C_1$–$C_7$)heteroalkyl, —OC(O)—($C_1$–$C_7$)heteroalkyl, —$NH_2$, —NH($C_1$–$C_7$)alkyl, —N(($C_1$–$C_7$)alkyl)$_2$ and —NH—S(O)$_2$—($C_1$–$C_5$)alkyl;
$R^2$ is a member selected from the group consisting of ($C_1$–$C_7$)alkyl, ($C_1$–$C_7$)heteroalkyl, aryl and aryl($C_1$–$C_7$)alkyl;
$X^1$, $X^2$, $X^3$, $X^4$, $X^5$ and $X^6$ are each independently a member selected from the group consisting of H, ($C_1$–$C_5$)alkyl, ($C_1$–$C_5$)heteroalkyl, F and Cl, with the proviso that no more than three of $X^1$ through $X^6$ are H, ($C_1$–$C_5$)alkyl or ($C_1$–$C_5$)heteroalkyl; and
Y is a member selected from the group consisting of —N($R^{12}$)S(O)$_m$—, —N($R^{12}$)S(O)$_m$N($R^{13}$)—, —N($R^{12}$)C(O)—, —N($R^{12}$)C(O)N($R^{13}$)—, —N($R^{12}$)C(S)— and —N($R^{12}$)C(O)O—;
wherein $R^{12}$ and $R^{13}$ are each independently selected from the group consisting of H, ($C_1$–$C_7$)alkyl, ($C_1$–$C_7$)heteroalkyl, aryl and aryl($C_1$–$C_7$)alkyl, and optionally when Y is —N($R^{12}$)S(O)$_m$— or —N($R^{12}$)S(O)$_m$N($R^{13}$)—, $R^{12}$ forms a five- or six-membered ring fused to Ar or to $R^2$ through covalent attachment to Ar or to $R^2$, respectively; and the subscript m is an integer of from 1 to 2.

40. A method in accordance with claim 39, wherein said LXR function is associated with a disease or condition selected from the group consisting of lipid disorders and other metabolic disorders.

41. A method in accordance with claim 40, wherein said disease or condition is selected from the group consisting of atherosclerosis, elevated LDL plasma levels, low HDL plasma levels, hypertriglyceridemia, hypertension and hypercholesterolemia.

42. A method in accordance with claim 40, wherein said disease or condition is selected from the group consisting of obesity, diabetes, vitamin deficiency, osteoporosis, and multidrug resistance to chemotherapeutic drugs.

43. A method in accordance with claim 39, wherein said compound is administered in combination with a second lipid-lowering or cholesterol-lowering agent.

44. A composition of claim 1, further comprising a second lipid-lowering or cholesterol-lowering agent.

45. A composition in accordance with claim 1, wherein said compound has the formula:

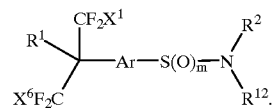

46. A composition in accordance with claim 1, wherein said compound has the formula:

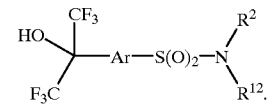

47. A composition in accordance with claim 1, wherein said compound has the formula:

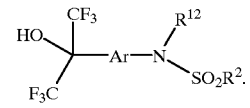

* * * * *